US007396933B2

(12) United States Patent
Choi et al.

(10) Patent No.: US 7,396,933 B2
(45) Date of Patent: *Jul. 8, 2008

(54) QUINOLINONE-CARBOXAMIDE COMPOUNDS

(75) Inventors: Seok-Ki Choi, Palo Alto, CA (US); Paul Fatheree, San Francisco, CA (US); Roland Gendron, San Francisco, CA (US); Adam A Goldblum, San Francisco, CA (US); Lan Jiang, Foster City, CA (US); Daniel D Long, San Francisco, CA (US); Daniel Marquess, Half Moon Bay, CA (US)

(73) Assignee: Theravance, Inc., South San Francisco, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 11/267,720

(22) Filed: Nov. 4, 2005

(65) Prior Publication Data

US 2006/0100426 A1    May 11, 2006

Related U.S. Application Data

(60) Provisional application No. 60/625,233, filed on Nov. 5, 2004.

(51) Int. Cl.
*C07D 215/00* (2006.01)
(52) U.S. Cl. .................................................. 546/156
(58) Field of Classification Search ............... 546/156, 546/123
See application file for complete search history.

(56) References Cited

U.S. PATENT DOCUMENTS

| | | | |
|---|---|---|---|
| 4,321,378 A | 3/1982 | Dostert et al. | |
| 4,772,706 A * | 9/1988 | Wemple et al. | ............. 544/349 |
| 4,845,092 A | 7/1989 | Sanger et al. | |
| 4,853,394 A | 8/1989 | King et al. | |
| 4,937,247 A | 6/1990 | King | |
| 5,017,573 A | 5/1991 | Kon et al. | |
| 5,037,844 A | 8/1991 | Hamminga et al. | |
| 5,047,410 A | 9/1991 | Donetti et al. | |
| 5,096,901 A * | 3/1992 | Ward et al. | ............. 514/213.01 |
| 5,223,511 A | 6/1993 | Turconi et al. | |
| 5,248,684 A | 9/1993 | Suzuki et al. | |
| 5,272,154 A | 12/1993 | Dixon et al. | |
| 5,298,510 A | 3/1994 | Tyers | |
| 5,319,085 A | 6/1994 | Suzuki et al. | |
| 5,552,398 A | 9/1996 | King et al. | |
| 5,561,149 A | 10/1996 | Azria et al. | |
| 5,571,820 A | 11/1996 | Ohuchi et al. | |
| 5,654,320 A | 8/1997 | Catlow et al. | |
| 5,684,003 A | 11/1997 | Kikuchi et al. | |
| 5,696,129 A | 12/1997 | King et al. | |
| 5,733,917 A | 3/1998 | Ohuchi et al. | |
| 5,741,801 A | 4/1998 | King et al. | |
| 5,753,673 A | 5/1998 | Ohuchi et al. | |
| 5,773,436 A | 6/1998 | Muller et al. | |
| 5,864,039 A | 1/1999 | Kawakita et al. | |
| 5,914,405 A | 6/1999 | Wilson | |
| 5,945,434 A | 8/1999 | Suzuki et al. | |
| 6,002,009 A | 12/1999 | Cereda et al. | |
| 6,117,882 A | 9/2000 | Schaus et al. | |
| 6,172,062 B1 | 1/2001 | Clark et al. | |
| 6,197,769 B1 | 3/2001 | Alisi et al. | |
| 6,281,218 B1 | 8/2001 | Cereda et al. | |
| 6,294,555 B1 | 9/2001 | Kato et al. | |
| 6,452,013 B1 | 9/2002 | Bosmans et al. | |
| 6,544,997 B1 | 4/2003 | Bosmans et al. | |
| 6,624,162 B2 | 9/2003 | Uchida et al. | |
| 6,696,468 B2 | 2/2004 | Kato et al. | |
| 6,979,690 B2 | 12/2005 | Gymer et al. | |
| 2002/0173505 A1 | 11/2002 | Skogvall | |
| 2004/0122043 A1 | 6/2004 | Iguchi et al. | |
| 2004/0127514 A1 | 7/2004 | Katsu et al. | |
| 2004/0266814 A1 | 12/2004 | Noguchi et al. | |
| 2005/0197335 A1 | 9/2005 | Marquess et al. | |
| 2005/0228014 A1 | 10/2005 | Marquess et al. | |
| 2005/0277671 A1 | 12/2005 | Ando et al. | |
| 2005/0277672 A1 | 12/2005 | Ando et al. | |
| 2005/0277673 A1 | 12/2005 | Ando et al. | |
| 2006/0100236 A1 | 5/2006 | Choi et al. | |
| 2006/0229332 A1 | 10/2006 | Fatheree et al. | |

FOREIGN PATENT DOCUMENTS

| | | | |
|---|---|---|---|
| EP | 0 309 423 A2 | 3/1989 | |
| EP | 0 623 621 A1 | 11/1994 | |

(Continued)

OTHER PUBLICATIONS

Suzuki et al. Chem.Pharm.Bull. 2000, 48, 2003-2008.*

(Continued)

*Primary Examiner*—D. Margaret Seaman
*Assistant Examiner*—Nizal S. Chandrakumar
(74) *Attorney, Agent, or Firm*—Jeffrey A. Hagenah; Roberta P. Saxon

(57) ABSTRACT

The invention provides novel quinolinone-carboxamide 5-$HT_4$ receptor agonist compounds. The invention also provides pharmaceutical compositions comprising such compounds, methods of using such compounds to treat diseases associated with 5-$HT_4$ receptor activity, and processes and intermediates useful for preparing such compounds.

13 Claims, No Drawings

FOREIGN PATENT DOCUMENTS

| | | |
|---|---|---|
| EP | 05824243.9 | 7/2007 |
| ES | 2 154 605 A1 | 4/2001 |
| IT | 01298271 B1 | 12/1999 |
| JP | 04005289 A2 | 1/1992 |
| JP | 08231544 A2 | 9/1996 |
| WO | WO 93/03725 A1 | 3/1993 |
| WO | WO 97/35860 A1 | 10/1997 |
| WO | WO 99/20633 A1 | 4/1999 |
| WO | WO 00/63215 A2 | 10/2000 |
| WO | WO 01/25236 A2 | 4/2001 |
| WO | WO 02/36113 A1 | 5/2002 |
| WO | WO 2004/026868 A1 | 4/2004 |
| WO | WO 2005/000837 A1 | 1/2005 |
| WO | WO 2005/000838 A1 | 1/2005 |
| WO | WO 2005/021539 A1 | 3/2005 |
| WO | WO 2005/049608 A1 | 6/2005 |
| WO | WO 2005/073222 A1 | 8/2005 |
| WO | WO 2005/092882 A1 | 10/2005 |

OTHER PUBLICATIONS

Allegretti et al., "One-pot, new stereoselective synthesis of *endo*-tropanamine", Tetrahedron Letters 42, pp. 4257-4259 (2001).

Baxter et al., "Benzimidazolone derivatives act as 5-HT$_4$ receptor ligands in rat oesophagus", European Journal of Pharmacology, 212, pp. 225-229 (1992).

Berdini et al., "A modified palladium catalysed reductive amination procedure", Tetrahedron 58, pp. 5669-5674 (2002).

Bermudez et al., "5-Hydroxytryptamine (5-HT$_3$) Receptor Antagonists. 1. Indazole and Indolizine-3-carboxylic Acid Derivatives", J. Med. Chem., 33, pp. 1924-1929 (1990).

Blum et al., "Design and Synthesis of Novel Ligands for the 5-HT$_3$ and the 5-HT$_4$ Receptor", Bioorganic & Medicinal Chemistry Letters, vol. 2, No. 5, pp. 461-466 (1992).

Curtet et al., "New Arylpiperazine Derivatives as Antagonists of the Human Cloned 5-HT$_4$ Receptor Isoforms", J. Med. Chem., 43, pp. 3761-3769 (2000).

Dumuis et al., "Characterization of a novel 5-HT$_4$ receptor antagonist of the azabicycloalkyl benzimidazolone class: DAU 6285", Naunyn-Schmiedeberg's Arch Pharmacol, 345, pp. 264-269 (1992).

Dumuis et al., "Azabicycloalkyl benzimidazolone derivatives as a novel class of potent agonists at the 5-HT$_4$ receptor positively coupled to adenylate cyclase in brain", Naunyn-Schmiedeberg's Arch Pharmacol, 343, pp. 245-251 (1991).

Fake et al., "BRL 43694: A Potent and Novel 5-HT$_3$ Receptor Antagonist", Br. J. Pharmacol., 91, 335P (1987).

Kaumann et al., "Indazole as an Indole Bioisostere:5-HT$_4$ Receptor Antagonism.", Bioorganic & Medicinal Chemistry Letters, vol. 2, No. 5, pp. 419-420 (1992).

Langlois et al., "5-HT$_4$ Receptor Ligands: Applications and New Prospects", J Med Chem, vol. 46, No. 3, pp. 319-344 (2003).

Lopez-Rodriguez et al., "3-D-QSAR/CoMFA and Recognition Models of Benzimidazole Derivatives at the 5-HT$_4$ Receptor", Bioorganic & Medicinal Chemistry Letters, 11, pp. 2807-2811 (2001).

Lopez-Rodriguez et al., "Benzimidazole Derivates. Part 1: Synthesis and Structure-Activity Relationships of New Benzimidazole-4-carboxamides and Carboxylates as Potent and Selective 5-HT$_4$ Receptor Antagonists", Bioorganic & Medicinal Chemistry, 7, pp. 2271-2281 (1999).

Lopez-Rodriguez et al., "Benzimidazole Derivatives. 3. 3D-QSAR/CoMFA Model and Computational Simulation for the Recognition of 5-HT$_4$ Receptor Antagonists", J. Med. Chem., 45, pp. 4806-4815 (2002).

Lopez-Rodriguez et al., "Benzimidazone derivatives 4. The recognition of the voluminous substituent attached to the basic amino group of 5-HT$_4$ receptor antagonists", Journal of Computer-Aided Molecular Design, 17, pp. 515-524 (2003).

Lopez-Rodriguez et al., "Design and Synthesis of New Benzimidazole-Arylpiperazine Derivatives Acting as Mixed 5-HT$_{1A}$/5-HT$_3$ Ligands", Bioorganic & Medicinal Chemistry Letters, 13, pp. 3177-3180 (2003).

Lopez-Rodriguez et al., "Study of the bioactive conformation of novel 5-HT$_4$ receptor ligands: influence of an intramolecular hydrogen bond", Tetrahedron, 57, pp. 6745-6749 (2001).

Schaus et al., "Synthesis and Structure-Activity Relationships of Potent and Orally Active 5-HT$_4$ Receptor Antagonists: Indazole and Benzimidazolone Derivatives", J. Med. Chem., 41, pp. 1943-1955 (1998).

Suzuki et al., "Synthesis and Evaluation of Novel 2-Oxo-1,2-dihydro-3-quinolinecarboxamide Derivatives as Potent and Selective Serotonin 5-HT$_4$ Receptor Agonists", Chem. Pharm. Bull., 49(1), pp. 29-39 (2001).

Suzuki et al., "A Practical Procedure for Preparation of *N*-(*endo*-8-3-hydroxy)propyl-8-azabicyclo[3.2.1]oct-3-yl)-1-isopropyl-2-oxo-1,2-dihydro-3-quinoline-carboxamide (TS-951)", Heterocycles, vol. 53, No. 11, pp. 2471-2485 (2000).

Suzuki et al., "Synthesis and Evaluation of Novel 2-Oxo-1,2-dihydro-3-quinolinecarboxamide Derivatives as Serotonin 5-HT$_4$ Receptor Agonists", Chem. Pharm. Bull., 48(12), pp. 2003-2008 (2000).

Tapia et al., "2,3-Dihydro-2-oxo-1*H*-benzimidazole-1-carboxamides with Selective Affinity for the 5-HT$_4$ Receptor: Synthesis and Structure-Affinity and Structure-Activity Relationships of a New Series of Partial Agonist and Antagonist Derivatives", J. Med. Chem., 42, pp. 2870-2880 (1999).

Turconi et al., "Azabicycloalkyl benzimidazolones: Interaction with serotonergic 5-HT$_3$ and 5-HT$_4$ receptors and potential therapeutic implications", Drugs of the Future, 16(11), pp. 1011-1026 (1991).

Turconi et al., "Synthesis of a New Class of 2,3-Dihydro-2-oxo-1*H*-benzimidazole-1-carobxylic Acid Derivatives as Highly Potent 5-HT$_3$ Receptor Antagonists", J. Med. Chem., 33, pp. 2101-2108 (1990).

Abstract of JP 04089489 A2, "Preparation of azabicyclo compound quaternary ammonium salts as 5-HT3 receptor antagonists", published Mar. 23, 1992, Chemical Abstracts Accession No. CAN 117:19164.

Abstract of JP 07324087 A2, "Preparation of 2-oxo-1,2-dihydro-4-quinolinecarboxylic acid derivatives as serotonin receptor stimulants", published Dec. 12, 1995, Chemical Abstracts Accession No. CAN 124:260866.

Abstract of JP 08034783 A2, "Preparation of N-(8-azabicyclo[3.2.1]oct-3-yl)-2-oxo,1,2-dihydro-3-quinolinecarboxamide and (8-azabicyclo[3.2.1]oct-3-yl)-2-oxo,1,2-dihydro-3-quinolinecarboxylate derivatives as stimulants of serotonin (5-HT4) receptor", published Feb. 6, 1996, Chemical Abstracts Accession No. CAN 124:343137.

Abstract of JP 08034785 A2, "Preparation of N-(8-azoniabicyclo[3.2.1]oct-3-yl)-2-oxo,1,2-dihydro-3-quinolinecarboxamide and (8-azoniabicyclo[3.2.1]oct-3-yl)-2-oxo,1,2,-dihydro-3-quinolinecarboxylate derivatives as stimulants of serotonin 4 (5-HT4) receptor", published Feb. 6, 1996, Chemical Abstracts Accession No. CAN 124:343138.

Abstract of JP 09194374 A2, "Digestive tract disease-treating agents", published Jul. 29, 1997, Chemical Abstracts Accession No. CAN 127:210377.

Abstract of JP 09241241 A2, "Preparation of N-(1-substituted-4-piperidyl)benzamides having serotonin receptor agonist activity", published Sep. 16, 1997, Chemical Abstracts Accession No. CAN 127:293254.

Abstract of JP 11001472 A2, "Preparation of 4-amino-5-halo-2-alkoxy-N-(4-piperidinylalkyl or 4-piperidinyl carbonyl)benzamides for improving digestive tract function", published Jan. 6, 1999, Chemical Abstracts Accession No. CAN 130:139257.

Abstract of JP 2001122784 A2, "Pharmaceuticals containing 1-[(1-substituted 4-piperidinyl)methyl]-4-piperidines as serotonin 4 receptor agonists", published May 8, 2001, Chemical Abstracts Accession No. CAN 134:348274.

Abstract of JP 2004277318 A2, "1-(1-Substitued-4-piperidinylmethyl)piperidine derivatives as 5-HT4 receptor agonists, pharmaceutical compositions containing them, and their use", published Oct. 7, 2004, Chemical Abstracts Accession No. CAN 141:307555.

Abstract of JP 2004277319 A2, "1-(4-piperidinylmethyl)piperidinylamide derivatives as 5-HT4 receptor agonists, pharmaceutical compositions containing them, and their use", published Oct 7, 2004, Chemical Abstracts Accession No. CAN 141:307556.

Abstract of JP 2004277320 A2, "1,4-disubstituted piperidine derivatives as 5-HT4 receptor agonists, pharmaceutical compositions containing them, and their use", published Oct. 7, 2004, Chemical Abstracts Accession No. CAN 141:307557.

Harada et al., "Novel N-[1-(1-Substituted 4-Piperidinylmethyl)-4-piperidinyl]benzamides as Potent Colonic Prokinetic Agents", BioOrganic & Medicinal Chemistry Letters 12, pp. 967-970 (2002).

U.S. Appl. No. 11/547,790, filed Apr. 6, 2007, Marquess et al.

U.S. Appl. No. 11/824,450, filed Apr. 29, 2007, Marquess et al.

* cited by examiner

QUINOLINONE-CARBOXAMIDE COMPOUNDS

CROSS-REFERENCE TO RELATED APPLICATIONS

This application claims the benefit of U.S. Provisional Application No. 60/625,233, filed on Nov. 5, 2004, the disclosure of which is incorporated herein by reference in its entirety.

BACKGROUND OF THE INVENTION

1. Field of the Invention

The invention is directed to quinolinone-carboxamide compounds which are useful as $5\text{-HT}_4$ receptor agonists. The invention is also directed to pharmaceutical compositions comprising such compounds, methods of using such compounds for treating medical conditions mediated by $5\text{-HT}_4$ receptor activity, and processes and intermediates useful for preparing such compounds.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of $5\text{-HT}_4$ receptors and identification of pharmaceutical agents that interact with them has been the focus of significant recent activity. (See, for example, the review by Langlois and Fischmeister, *J. Med. Chem.* 2003, 46, 319-344.) $5\text{-HT}_4$ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some $5\text{-HT}_4$ receptor agonist compounds may be used in the treatment of central nervous system disorders including cognitive disorders, behavioral disorders, mood disorders, and disorders of control of autonomic function.

Despite the broad utility of pharmaceutical agents modulating $5\text{-HT}_4$ receptor activity, few $5\text{-HT}_4$ receptor agonist compounds are in clinical use at present. Accordingly, there is a need for new $5\text{-HT}_4$ receptor agonists that achieve their desired effects with minimal side effects. Preferred agents may possess, among other properties, improved selectivity, potency, pharmacokinetic properties, and/or duration of action.

SUMMARY OF THE INVENTION

The invention provides novel compounds that possess $5\text{-HT}_4$ receptor agonist activity. Among other properties, compounds of the invention have been found to be potent and selective $5\text{-HT}_4$ receptor agonists.

Accordingly, the invention provides a compound of formula (I):

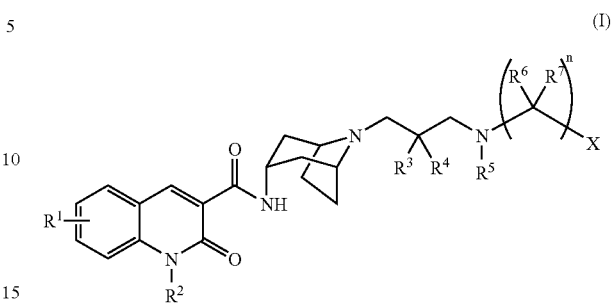

wherein:
$R^1$ is hydrogen, halo, hydroxy, $C_{1-4}$alkyl, or $C_{1-4}$alkoxy;
$R^2$ is $C_{3-4}$alkyl or $C_{3-6}$cycloalkyl;
$R^3$ is hydroxy, $C_{1-3}$alkoxy, hydroxy-substituted $C_{1-4}$alkyl, or —OC(O)NR$^a$R$^b$;
$R^4$ is hydrogen or $C_{1-4}$alkyl;
X is selected from —N(R$^8$)C(O)R$^9$, —N(R$^8$)S(O)$_2$R$^{10}$, —S(R$^{11}$)O$_2$, —N(R$^8$)C(O)OR$^{12}$, —N(R$^8$)C(O)NR$^{13}$R$^{14}$, —N(R$^8$)SO$_2$NR$^{13}$R$^{14}$—C(O)NR$^{13}$R$^{14}$, —OC(O)NR$^{13}$R$^{14}$, —C(O)OR$^{12}$, —OR$^{15}$, —NR$^8$R$^{16}$ cyano, —SR$^{15}$, CF$_3$, pyridinyl, pyrrolyl, thiomorpholinyl, thiazolidinyl, 1,1-dioxoisothiazolidinyl, imidazolyl, indolyl, tetrahydrofuranyl, pyrrolidinyl and piperidinyl, wherein pyrrolidinyl is optionally substituted with oxo and piperidinyl is optionally substituted with 1 to 3 halo;
$R^5$ is hydrogen or $C_{1-4}$alkyl, wherein $C_{1-4}$alkyl is optionally substituted with hydroxy, $C_{1-3}$alkoxy, or cyano;
$R^6$ and $R^7$ are independently selected from hydrogen, hydroxy, halo, and $C_{1-4}$alkyl, wherein $C_{1-4}$alkyl is optionally substituted with hydroxy or $C_{1-3}$alkoxy;
$R^8$ is hydrogen or $C_{1-4}$alkyl;
or $R^5$ and $R^8$, $R^5$ and $R^6$, or $R^6$ and $R^8$ taken together form $C_{2-5}$alkylenyl, wherein $C_{2-5}$alkylenyl is optionally substituted with hydroxy, halo, hydroxy-substituted $C_{1-3}$alkyl, or $C_{1-3}$alkoxy;
or $R^3$ and $R^5$ taken together form —OCH$_2$CH$_2$—;
or $R^5$ and $R^6$ taken together form —(CH$_2$)$_q$-Q-(CH$_2$)$_q$, wherein Q is oxygen or sulfur and q is independently 0, 1, or 2;
$R^9$ is hydrogen, furanyl, or $C_{1-4}$alkyl, wherein $C_{1-4}$alkyl is optionally substituted with hydroxy or with from 1 to 3 halo;
$R^{10}$ is hydrogen or $C_{1-4}$alkyl, wherein $C_{1-4}$alkyl is optionally substituted with —SO$_2$R$^c$, $C_{3-6}$cycloalkyl or with from 1 to 3 halo;
or $R^8$ and $R^{10}$ taken together form $C_3$alkylenyl;
$R^{11}$ is hydrogen, $C_{1-4}$alkyl, or —NR$^b$R$^c$;
or $R^5$ and $R^{11}$ or $R^6$ and $R^{11}$ taken together form $C_{2-5}$alkylenyl;
$R^{12}$R$^{13}$, and r are independently hydrogen or $C_{1-4}$alkyl;
$R^{15}$ is hydrogen or $C_{1-4}$alkyl, wherein $C_{1-4}$alkyl is optionally substituted with hydroxy;
or $R^5$ and $R^{15}$ taken together form $C_{1-4}$alkylenyl;
$R^{16}$ is CH$_2$)$_r$—R$^{17}$, wherein r is 0, 1, 2, or 3;
$R^{17}$ is selected from hydrogen, hydroxy, $C_{1-3}$alkyl, $C_{1-3}$alkoxy, —C(O)NR$^a$R$^b$, —C(O)-morpholinyl, pyridinyl, pyrrolyl, morpholinyl, and tetrahydrofuranyl, wherein $C_{1-3}$alkoxy is optionally substituted with hydroxy;

$R^a$, $R^b$, and $R^c$ are independently hydrogen or $C_{1-3}$alkyl; and n is 1, 2, 3, or 4;

provided that when n is 1, X forms a carbon-carbon bond with the carbon atom bearing the substituents $R^6$ and $R^7$;

or a pharmaceutically-acceptable salt or solvate or sterioisomer thereof.

The invention also provides a pharmaceutical composition comprising a therapeutically effective amount of a compound of the invention and a pharmaceutically-acceptable carrier.

The invention also provides a method of treating a disease or condition associated with 5-HT$_4$ receptor activity, e.g. a disorder of reduced motility of the gastrointestinal tract, the method comprising administering to the mammal, a therapeutically effective amount of a pharmaceutical composition comprising a pharmaceutically-acceptable carrier and a compound of the invention.

Further, the invention provides a method of treating a disease or condition associated with 5-HT$_4$ receptor activity in a mammal, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new 5-HT$_4$ receptor agonists, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with 5-HT$_4$ receptor activity, e.g. a disorder of reduced motility of the gastrointestinal tract, in a mammal.

DETAILED DESCRIPTION OF THE INVENTION

The invention provides novel quinolinone-carboxamide 5-HT$_4$ receptor agonists of formula (I), or pharmaceutically-acceptable salts or solvates or stereoisomers thereof. The following substituents and values are intended to provide representative examples of various aspects of this invention. These representative values are intended to further define such aspects and are not intended to exclude other values or limit the scope of the invention.

In a specific aspect of the invention, $R^1$ is hydrogen, halo, or $C_{1-4}$alkyl.

In another specific aspect, $R^1$ is hydrogen, halo, or $C_{1-3}$alkyl.

In other specific aspects, $R^1$ is hydrogen, fluoro, chloro, bromo, or methyl; or $R^1$ is hydrogen.

In a specific aspect, $R^2$ is $C_{3-4}$alkyl.

Representative $R^2$ groups include n-propyl, isopropyl, n-butyl, sec-butyl, and tert-butyl.

In another specific aspect, $R^2$ is isopropyl.

In a specific aspect, $R^3$ is hydroxy, $C_{1-3}$alkoxy, hydroxy-substituted $C_{1-2}$alkyl or —OC(O)NR$^a$R$^b$. Representative $R^3$ groups include, but are not limited to, hydroxy, methoxy, hydroxymethyl, 2-hydroxyethyl, and —OC(O)NR$^a$R$^b$, wherein $R^a$ and $R^b$ are independently hydrogen or methyl.

In other specific aspects, $R^3$ is hydroxy, methoxy, hydroxymethyl, —OC(O)NHCH$_3$, or —OC(O)N(CH$_3$)$_2$; $R^3$ is hydroxy or —OC(O)NHCH$_3$; or $R^3$ is hydroxy.

In specific aspects, $R^4$ is hydrogen or methyl; or $R^4$ is hydrogen.

In a specific aspect, $R^5$ is hydrogen or $C_{1-4}$alkyl, wherein $C_{1-4}$alkyl is optionally substituted with hydroxy, $C_{1-3}$alkoxy, or cyano.

In another specific aspect, $R^5$ is hydrogen, $C_{1-3}$alkyl, or $C_{1-3}$alkyl substituted at the terminal position with hydroxy, $C_{1-3}$alkoxy, or cyano. Representative $R^5$ groups include, but are not limited to, hydrogen, methyl, ethyl, 2-hydroxyethyl, 2-methoxyethyl, cyanomethyl, and 2-cyanoethyl.

In another specific aspect, $R^5$ is hydrogen, $C_{1-3}$alkyl, or $C_{1-3}$alkyl substituted at the terminal position with hydroxy.

In a specific aspect, $R^6$ and $R^7$ are independently selected from hydrogen, hydroxy, halo, and $C_{1-4}$alkyl, wherein $C_{1-4}$alkyl is optionally substituted with hydroxy or $C_{1-3}$alkoxy.

In another specific aspect, $R^6$ and $R^7$ are independently hydrogen, hydroxy, halo, $C_{1-2}$alkyl, or hydroxy-substituted $C_{1-2}$alkyl. Representative $R^6$ and $R^7$ groups include, but are not limited to, hydrogen, hydroxy, fluoro, chloro, hydroxyethyl, and hydroxymethyl.

In another specific aspect, $R^6$ and $R^7$ are each hydrogen.

In a specific aspect, $R^3$ and $R^5$ taken together form —OCH$_2$CH$_2$—.

In a specific aspect, n is 2 or 3 and $R^5$ and $R^6$ taken together form —CH$_2$CH$_2$O— or —CH$_2$CH$_2$OCH$_2$—.

In other specific aspects, n is 2 and $R^5$ and $R^6$ taken together form $C_{2-3}$alkylenyl or $C_2$alkylenyl.

In a specific aspect, X is selected from —N(R$^8$)C(O)R$^9$, —N(R$^8$)S(O)$_2$R$^{10}$, —S(R$^{11}$)O$_2$, —N(R$^8$)C(O)OR$^{12}$, —N(R$^8$)C(O)NR$^{13}$R$^{14}$, —N(R$^8$)SO$_2$NR$^{13}$R$^{14}$, —C(O)NR$^{13}$R$^{14}$, —OC(O)NR$^{13}$R$^{14}$, —C(O)OR$^{12}$, —OR$^{15}$, and cyano.

In another specific aspect, X is selected from —N(R$^8$)C(O)R$^9$; —N(R$^8$)S(O)$_2$R$^{10}$, —S(R$^{11}$)O$_2$, —N(R$^8$)C(O)NR$^{13}$R$^{14}$, —C(O)NR$^{13}$R$^{14}$, —OC(O)NR$^{13}$R$^{14}$, —OR$^{15}$, and cyano.

In yet another specific aspect, X is selected from —N(R$^8$)C(O)R$^9$, —N(R$^8$)S(O)$_2$R$^{10}$, —S(R$^{11}$)O$_2$, and —N(R$^8$)C(O)NR$^{13}$R$^{14}$. In still another specific aspect, X is —N(R$^8$)S(O)$_2$R$^{10}$.

In specific aspects, $R^8$ is hydrogen or $C_{1-4}$alkyl; $R^8$ is hydrogen or $C_{1-3}$alkyl; or $R^8$ is hydrogen or methyl.

In a specific aspect, n is 2 and $R^5$ and $R^8$ taken together form $C_2$alkylenyl.

In another specific aspect, n is 2 and $R^5$ and $R^8$ taken together form $C_3$alkylenyl.

In a specific aspect, n is 2 and $R^6$ and $R^8$ taken together form $C_{2-3}$alkylenyl.

In a specific aspect, $R^9$ is hydrogen, furanyl, or $C_{1-3}$alkyl, wherein $C_{1-3}$alkyl is optionally substituted with hydroxy. Representative $R^9$ groups include, but are not limited to, hydrogen, furanyl, methyl, ethyl, propyl, isopropyl, and 1-hydroxyethyl.

In other specific aspects, $R^9$ is hydrogen or $C_{1-3}$alkyl; or $R^9$ is hydrogen or methyl.

In a specific aspect, $R^{10}$ is hydrogen or $C_{1-4}$alkyl, wherein $C_{1-4}$alkyl is optionally substituted with —SO$_2$R$^c$, $C_{3-6}$cycloalkyl or with from 1 to 3 halo.

In another specific aspect, $R^{10}$ is hydrogen or $C_{1-3}$alkyl, wherein $C_{1-3}$alkyl is optionally substituted with —SO$_2$R$^c$ wherein $R^c$ is $C_{1-3}$alkyl. Representative $R^{10}$ groups include, but are not limited to, hydrogen, methyl, ethyl, propyl, isopropyl, and methanesulfonylmethyl.

In other specific aspects, $R^{10}$ is hydrogen, $C_{1-3}$alkyl, or methanesulfonylmethyl; or $R^{10}$ is methyl, isopropyl, or methanesulfonylmethyl; or $R^{10}$ is methyl.

In specific aspects, $R^{11}$ is hydrogen, $C_{1-4}$alkyl, or —$NR^bR^c$; $R^{11}$ is hydrogen or $C_{1-3}$alkyl; or $R^{11}$ is methyl.

In another specific aspect, n is 2 and $R^5$ and $R^{11}$ taken together form $C_2$alkylenyl.

In yet another specific aspect, n is 2 or 3 and $R^6$ and $R^{11}$ taken together form $C_2$alkylenyl.

In specific aspects, $R^{12}$, $R^{13}$, and $R^{14}$ are independently hydrogen or $C_{1-3}$alkyl, or $R^{12}$, $R^{13}$, and $R^{14}$ are independently hydrogen or methyl.

In a specific aspect, $R^{15}$ is hydrogen or $C_{1-4}$alkyl, wherein $C_{1-4}$alkyl is optionally substituted with hydroxy.

In other specific aspects, $R^{15}$ is hydrogen, $C_{1-3}$alkyl, or $C_{1-3}$alkyl substituted at the terminal position with hydroxy; or $R^{15}$ is hydrogen or $C_{1-3}$alkyl. Representative $R^{15}$ groups include, but are not limited to, hydrogen, methyl, ethyl, and 2-hydroxyethyl.

In another specific aspect, $R^{15}$ is hydrogen or methyl.

In a specific aspect, $R^{16}$ is —$(CH_2)_r$—$R^{17}$, wherein r is 0, 1, or 2 and $R^{17}$ is selected from hydroxy, $C_{1-2}$alkoxy, —$C(O)NR^aR^b$, —$C(O)$-morpholinyl, pyridinyl, morpholinyl, and tetrahydrofuranyl, wherein $C_{1-2}$alkoxy is optionally substituted at the terminal position with hydroxy and $R^a$ and $R^b$ are independently hydrogen or methyl.

In a specific aspect, n is 1, 2, or 3.
In another specific aspect, n is 2, 3, or 4.
In another specific aspect, n is 2 or 3.
In yet another specific aspect, n is 2
In one aspect, the invention provides a compound of formula (II):

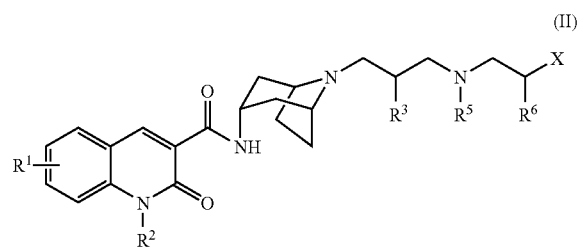

wherein:
$R^1$ is hydrogen, halo, or $C_{1-3}$alkyl;
$R^2$ is $C_{3-4}$alkyl;
$R^3$ is hydroxy, $C_{1-3}$alkoxy, hydroxy-substituted $C_{1-2}$alkyl, or —$OC(O)NR^aR^b$;
$R^5$ is hydrogen, $C_{1-3}$alkyl, or $C_{1-3}$alkyl substituted at the terminal position with hydroxy or cyano;
$R^6$ is hydrogen;
X is selected from —$N(R^8)C(O)R^9$; —$N(R^8)S(O)_2R^{10}$, —$S(R^{11})O_2$, —$N(R^8)C(O)NR^{13}R^{14}$, —$C(O)NR^{13}R^{14}$, —$OC(O)NR^{13}R^{14}$, —$OR^{15}$ and cyano;
$R^8$ is hydrogen or $C_{1-3}$alkyl;
$R^9$ is hydrogen or $C_{1-3}$alkyl;
$R^{10}$ is hydrogen or $C_{1-3}$alkyl, wherein $C_{1-3}$alkyl is optionally substituted with —$SO_2R^c$ wherein $R^c$ is $C_{1-3}$alkyl;
$R^{13}R^{14}$, and $R^{15}$ are independently hydrogen or $C_{1-3}$alkyl;
or $R^5$ and $R^8$, $R^5$ and $R^6$, or $R^5$ and $R^{11}$ taken together form $C_2$alkylenyl; or
a pharmaceutically-acceptable salt or solvate or stereoisomer thereof.

In another aspect, the invention provides a compound of formula (II) wherein:
$R^1$ is hydrogen;
$R^2$ is $C_{3-4}$alkyl;
$R^3$ is hydroxy, methoxy, hydroxymethyl, —$OC(O)N(H)CH_3$, or —$OC(O)N(CH_3)_2$;
$R^6$ is hydrogen;
X is selected from —$N(R^8)C(O)R^9$; —$N(R^8)S(O)_2R^{10}$, —$S(R^{11})O_2$, and —$N(R^8)C(O)NR^{13}R^{14}$;
$R^5$ and $R^8$ taken together form $C_2$alkylenyl;
$R^9$ is hydrogen or $C_{1-3}$alkyl;
$R^{10}$ is hydrogen, $C_{1-3}$alkyl, or methanesulfonylmethyl;
$R^5$ and $R^{11}$ taken together form $C_2$alkylenyl; and
$R^{13}$ and $R^{14}$ are independently hydrogen or $C_{1-3}$alkyl.

In separate aspects, the invention further provides compounds of formula (III):

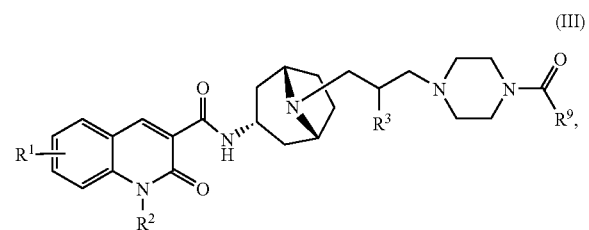

wherein $R^1$, $R^2$, $R^3$, and $R^9$ take any of the values defined above; compounds of formula (IV):

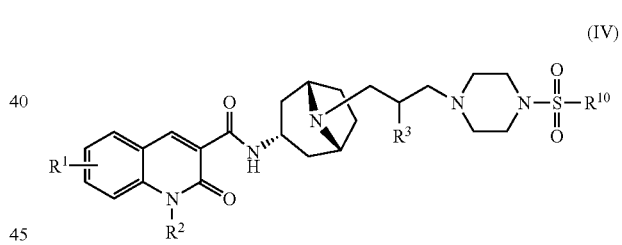

wherein $R^1$, $R^2$, $R^3$, and $R^{10}$ take any of the values defined above;
and compounds of formula (V):

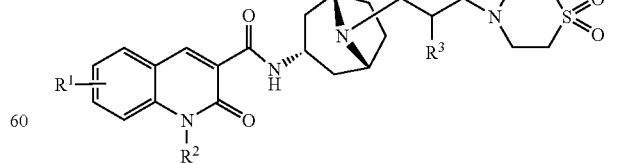

wherein $R^1$, $R^2$, and $R^3$ take any of the values defined above.

In still other specific aspects, the invention provides the compounds listed in Tables I to XXVIII below.

The chemical naming conventions used herein are illustrated for the compound of Example 1:

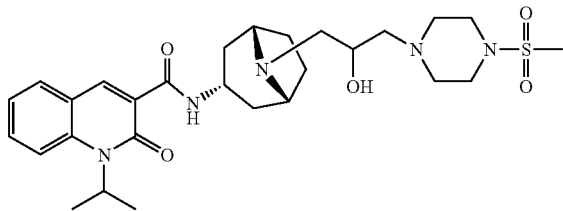

which is designated 1-isopropyl-2-oxo-1,2-dihydroquinoline-3-carboxylic acid {(1S,3R,5R)-8-[2-hydroxy-3-(4-methanesulfonylpiperazin-1-yl)propyl]-8-aza-bicyclo[3.2.1]oct-3-yl}-amide, according to the AutoNom software, provided by MDL Information Systems, GmbH (Frankfurt, Germany). The designation (1S,3R,5R) describes the relative orientation of the bonds associated with the bicyclic ring system that are depicted as solid and dashed wedges. The compound is alternatively denoted as N-[(3-endo)-8-[2-hydroxy-3-(4-methanesulfonylpiperazin-1-yl)propyl]-8-azabicyclo[3.2.1]oct-3-yl]-1-(1-methylethyl)-2-oxo-1,2-dihydro-3-quinolinecarboxamide. In all of the compounds of the invention listed explicitly below, the quinolinone-carboxamide group is endo to the azabicyclooctane group.

Particular mention may be made of the following compounds:

1-isopropyl-2-oxo-1,2-dihydroquinoline-3-carboxylic acid {(1S,3R,5R)-8-[2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid ((1S,3R,5R)-8-{2-hydroxy-3-[4-(propane-2-sulfonyl)piperazin-1-yl]propyl}-8-azabicyclo[3.2.1]oct-3-yl)-amide;

1-isopropyl-2-oxo-1,2-dihydroquinoline-3-carboxylic acid {(1S,3R,5R)-8-[3-(1,1-dioxo-1$\lambda^6$-thiomorpholin-4-yl)-2-hydroxypropyl]-8-azabicyclo[3.2.1]oct-3-yl}amide;

1-isopropyl-2-oxo-1,2-dihydroquinoline-3-carboxylic acid {(1S,3R,5R)-8-[(S)-2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid {(1S,3R,5R)-8-[(R)-2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid {(1S,3R,5R)-8-[3-(4-methanesulfonylmethanesulfonylpiperazin-1-yl)-2-methoxypropyl]-8-azabicyclo[3.2.1]-oct-3-yl}amide;

1-isopropyl-2-oxo-1,2-dihydroquinoline-3-carboxylic acid {(1S,3R,5R)-8-[3-(4-acetylpiperazin-1-yl)-2-methoxypropyl]-8-azabicyclo[3.2.1]oct-3-yl}amide;

1-isopropyl-2-oxo-1,2-dihydroquinoline-3-carboxylic acid {(1S,3R,5R)-8-[3-(1,1-dioxo-1$\lambda^6$-thiomorpholin-4-yl)-2-methoxypropyl]-8-azabicyclo[3.2.1]oct-3-yl}amide;

methylcarbamic acid 2-{(1S,3R,5R)-3-[(1-isopropyl-2-oxo-1,2-dihydroquinoline-3-carbonyl)amino]-8-azabicyclo[3.2.1]oct-8-yl}-1-(4-methanesulfonylpiperazin-1-ylmethyl)ethyl ester;

methylcarbamic acid 1-(4-dimethylcarbamoylpiperazin-1-ylmethyl)-2-{(1S,3R,5R)-3-[(1-isopropyl-2-oxo-1,2-dihydroquinoline-3-carbonyl)amino]-8-aza-bicyclo[3.2.1]oct-8-yl}ethyl ester;

methylcarbamic acid 1-[3-(acetylmethylamino)pyrrolidin-1-ylmethyl]-2-{(1S,3R,5R)-3-[(1-isopropyl-2-oxo-1,2-dihydroquinoline-3-carbonyl)amino]-8-aza-bicyclo[3.2.1]oct-8-yl}ethyl ester;

methylcarbamic acid 1-(4-acetylpiperazin-1-ylmethyl)-2-{(1S,3R,5R)-3-[(1-isopropyl-2-oxo-1,2-dihydroquinoline-3-carbonyl)amino]-8-azabicyclo[3.2.1]oct-8-yl}-ethyl ester;

methylcarbamic acid (R)-2-{(1S,3R,5R)-3-[(1-isopropyl-2-oxo-1,2-dihydro-quinoline-3-carbonyl)amino]-8-azabicyclo[3.2.1]oct-8-yl}-1-(4-methanesulfonyl-piperazin-1-ylmethyl)ethyl ester; and 1-isopropyl-2-oxo-1,2-dihydroquinoline-3-carboxylic acid {(1S,3R,5R)-8-[3-hydroxy-2-(4-methanesulfonylpiperazin-1-ylmethyl)propyl]-8-azabicyclo[3.2.1]oct-3-yl}-amide.

As exemplified by particular compounds listed above, the compounds of the invention may contain one or more chiral centers, in particular, the compounds may contain a chiral center at the carbon atom in formulas (I) to (IV) bearing the substituent $R^3$. Accordingly, the invention includes racemic mixtures, pure stereoisomers, and stereoisomer-enriched mixtures of such isomers, unless otherwise indicated. When a particular stereoisomer is shown, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, n-heptyl, n-octyl, n-nonyl, n-decyl and the like.

The term "alkylenyl" means a divalent saturated hydrocarbon group which may be linear or branched or combinations thereof. Unless otherwise defined, such alkylenyl groups typically contain from 1 to 10 carbon atoms. Representative alkylenyl groups include, by way of example, methylene, ethylene, n-propylene, n-butylene, propane-1,2-diyl (1-methylethylene), 2-methylpropane-1,2-diyl (1,1-dimethylethylene) and the like.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, cycloheptyl, cyclooctyl, and the like.

The term "halo" means fluoro, chloro, bromo or iodo.

The term "compound" means a compound that was synthetically prepared or prepared in any other way, such as by metabolism.

The term "therapeutically effective amount" refers to an amount sufficient to effect treatment when administered to a patient in need of treatment.

The term "treatment" as used herein refers to the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" refers to a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), napthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of formula (I) in which $R^3$ is defined as hydroxy or hydroxy-substituted $C_{1-4}$alkyl are prepared as illustrated in Scheme A. (The substituents and variables shown in the following schemes have the definitions provided herein unless otherwise indicated).

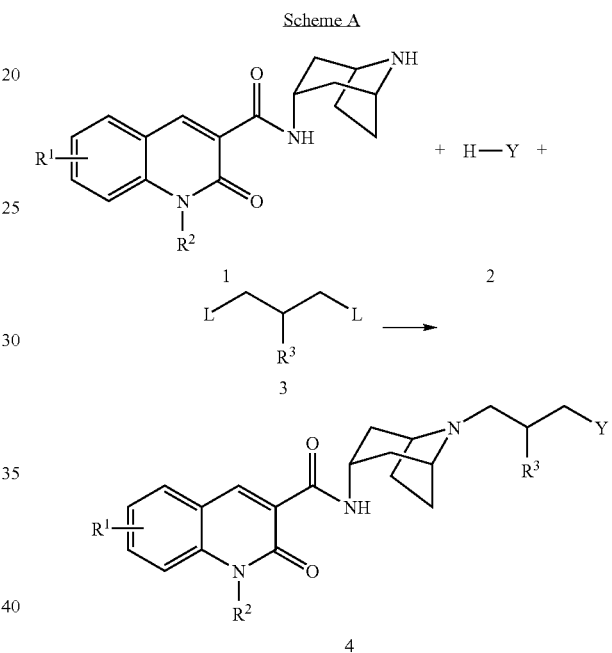

In Scheme A, intermediate 2 is a secondary amine, and L represents a leaving group such as chloro, bromo, iodo, methanesulfonyl, p-toluenesulfonyl, or trifluoromethanesulfonyl.

For convenience, the moiety:

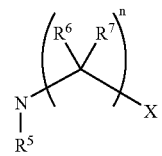

is represented by Y.

The reaction is typically conducted by contacting intermediate 1 with between about 1 and about 3 equivalents, each, of intermediates 2 and 3 in an inert diluent, such as methanol or ethanol, in the presence of an excess of base, for example between about 3 and about 6 equivalents, of base, such as N,N-diisopropylethylamine. The reaction is typically conducted at a temperature in the range of about 50° C. to about 80° C. for about 12 hours to about 24 hours, or until the reaction is substantially complete. Optionally, equal molar equivalents of intermediates 2 and 3 can be added in portions, as described in Example 1, below.

The product of formula (I) is isolated and purified by conventional procedures. For example, the product can be concentrated to dryness under reduced pressure, taken up in an aqueous weak acid solution and purified by HPLC chromatography.

It will be understood that in the process of Scheme A and in other processes described below using intermediate 1, intermediate 1 can be supplied in the form of the freebase or in a salt form, with appropriate adjustment of reaction conditions, as necessary, as known to those skilled in the art.

In Scheme A, the reaction of intermediate 1 with intermediates 2 and 3 is accomplished in a single step. Alternatively, the reaction can be performed in a stepwise manner. Using similar reaction conditions to those described above, intermediates 1 and 3 can first be coupled to form an intermediate 5:

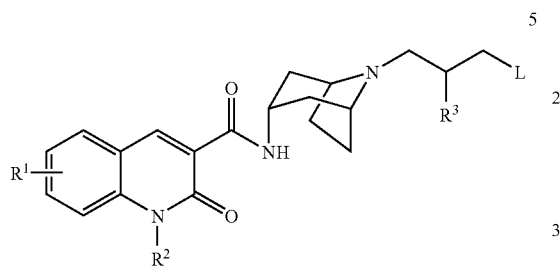

which is then reacted with the amine H—Y to provide a compound of formula (I). Alternatively, the amine can first be coupled to intermediate 3 to form an intermediate 10:

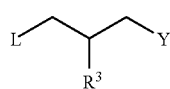

which is subsequently reacted with the quinolinone carboxamide-tropane intermediate 1.

Compounds of formula (I) can also be prepared by N-alkylating a compound of the form of formula (I) in which $R^2$ is defined as hydrogen, which can be prepared according to Scheme A. The N-alkylation reaction is typically conducted by contacting a compound of formula (I) in which $R^2$ is hydrogen with between about 1 and about 4 equivalents of a compound of the formula $L'$-$R^2$ in which $L'$ is a leaving group such as iodo or bromo. This reaction is typically conducted in a polar aprotic solvent such as dimethylformamide in the presence of between about 2 and about 4 equivalents of strong base, such as potassium tert-butoxide or sodium hydride. Typically, the reaction is performed at a temperature of between about 60° C. and about 100° C. for between about 6 and about 24 hours, or until the reaction is substantially complete.

In yet another alternative, compounds of formula (I) in which $R^1$ is other than hydrogen are prepared by conventional processes from compounds of formula (I) in which $R^1$ is hydrogen.

In another method of synthesis, compounds of formula (I) in which $R^3$ is hydroxy, $C_{1-3}$alkoxy, or —OC(O)$NR^aR^b$ and the carbon atom bearing the substituent $R^3$ is not chiral can be prepared from an azetidine intermediate 11, as illustrated in Scheme B:

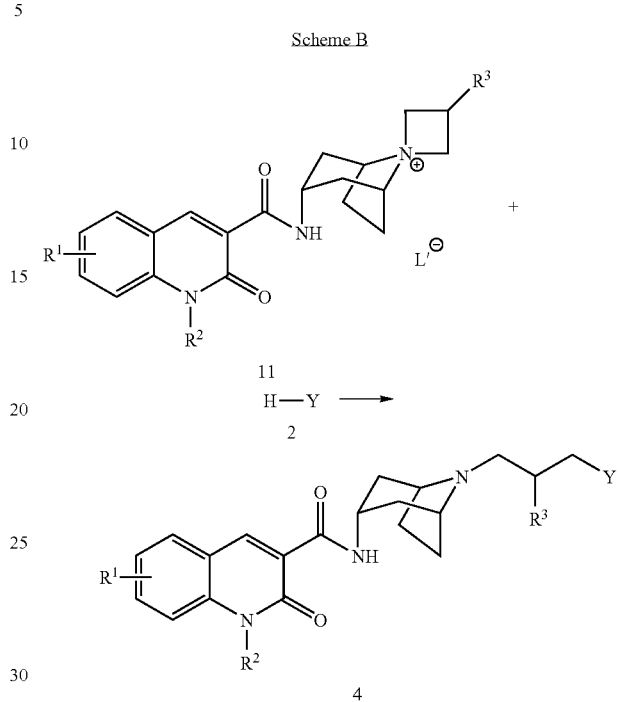

where $L'$ is a halo anion, such as Cl⁻ or Br⁻.

The reaction is typically conducted by contacting intermediate 11 with between about 1 and about 4 equivalents of intermediate 2 in an inert diluent, such as ethanol, methanol, or dimethylformamide, in the presence of an excess of base, for example between about 2 and about 4 equivalents, of base, such as N,N-diisopropylethylamine, 1,8-diazabicylco[5.4.0]undec-7-ene (DBU) or triethylamine. The reaction is typically conducted at a temperature in the range of about 50° C. to about 80° C. for about 1 hour to about 6 hours, or until the reaction is substantially complete. The product is isolated and purified by conventional means.

In yet another method of synthesis, compounds of formula (I) in which $R^3$ is hydroxy can be prepared as illustrated in Scheme C.

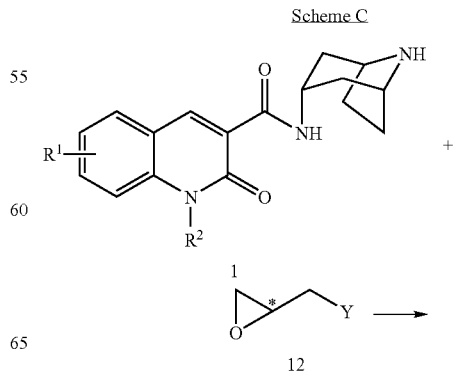

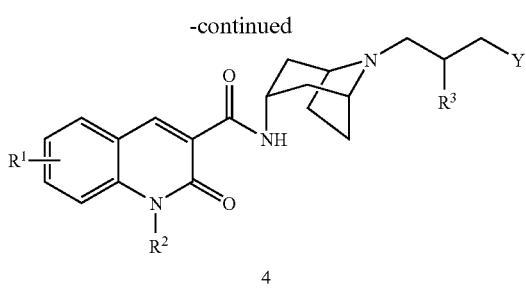

4

When an intermediate of formula 12 in which the carbon indicated by an asterisk is chiral is employed, the reaction of Scheme C is useful to prepare compounds of formula (I) having a chiral center at the carbon bearing the substituent $R^3$. Typically, in the reaction of Scheme C, intermediate 1 is contacted with between about 1 and about 1.2 equivalents of the epoxide 12 in an inert diluent such as ethanol or toluene. The reaction is typically conducted at at temperature in the range of about 50° C. to about 100° C. for about 12 hours to about 24 hours, or until the reaction is substantially complete. The product is isolated and purified by conventional means.

The intermediates employed in Schemes A, B, and C above are prepared from readily available starting materials. For example, when $R^3$ is hydroxy, an azetidine intermediate of formula 13 is prepared by the procedure illustrated in Scheme D:

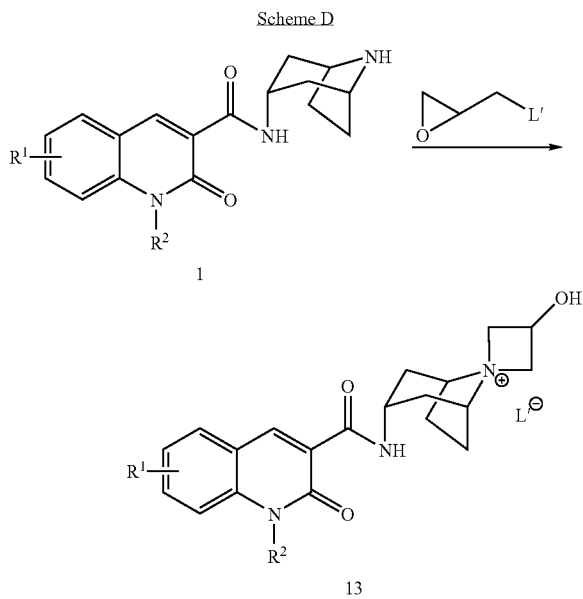

where L' represents a halo leaving group, such as bromo, chloro, or iodo.

An intermediate of formula 1 is reacted with an oxirane compound, preferably 2-bromomethyloxirane (commonly, epibromohydrin) to form the azetidine salt of formula 13. This reaction is typically conducted by contacting 1 with between about 2 and about 4 equivalents of 2-bromomethyloxirane in a polar diluent, such as ethanol. The reaction is typically conducted at ambient temperature for between about 24 and about 48 hours or until the reaction is substantially complete.

To form the azetidine intermediate 11 in which $R^3$ is $C_{1-3}$alkoxy, the intermediate of formula 13 above is contacted with from slightly less than one equivalent to about one equivalent of a $C_{1-3}$alkylhalide in an inert diluent in the presence of between about 1 and about 3 equivalents of a strong base, such as potassium tert-butoxide or sodium hydride. The reaction is typically conducted at ambient temperature for between about a quarter hour to an hour, or until the reaction is substantially complete. Suitable inert diluents include dichloromethane, tetrahydrofuran, toluene, dimethylformamide, and the like.

The azetidine intermediate 11 in which $R^3$ is a carbamic acid moiety of the form —OC(O)NR$^a$R$^b$ can also be prepared from the intermediate of formula 13 in which $R^3$ is hydroxy. For example, to prepare a compound of formula 11 in which $R^3$ is —OC(O)N(H)CH$_3$ or —OC(O)N(CH$_3$)$_2$, intermediate 13 is contacted with between about 1 and about 3 equivalents of methylisocyanate or dimethylisocyanate, respectively, in an inert diluent in the presence of between about 1 and about 3 equivalents of base, such as N,N-diisopropylethylamine, and of a catalytic amount of a strong base such as potassium tert-butoxide or sodium hydride. The reaction is typically conducted at ambient temperature for between about 4 hours and about 24 hours, or until the reaction is substantially complete.

A process for preparing intermediates of formula 1 is shown in Scheme E:

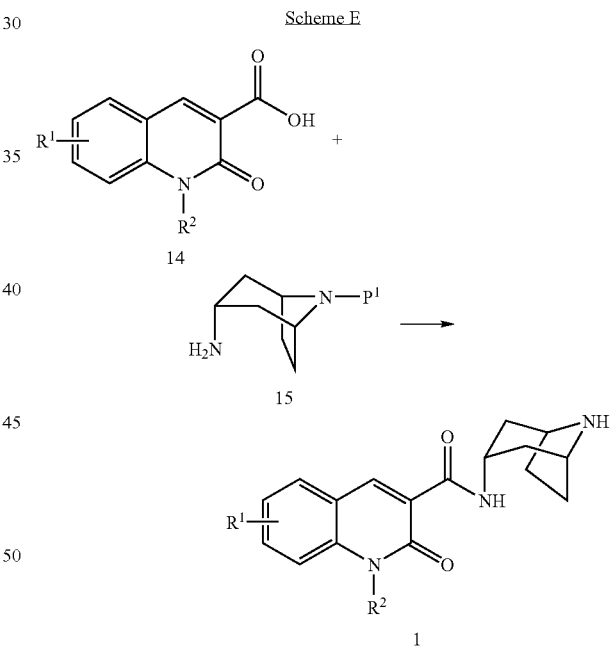

where $P^1$ represents an amino-protecting group. The protected aminoazabicyclooctane, or commonly, aminotropane 15 is first reacted with the substituted quinolinone carboxylic acid 14. Typically, this reaction is conducted by first converting 14 to an acid chloride by contacting 14 with at least one equivalent, preferably between about 1 and about 2 equivalents of an activating agent, such as thionyl chloride or oxalyl chloride in an aromatic diluent, such as toluene, benzene, xylene, or the like. The reaction is typically conducted at a temperature ranging from about 80° C. to about 120° C. for about 15 minutes to about 4 hours, or until the reaction is substantially complete.

The acid chloride solution is typically added to a biphasic mixture of about 1 equivalent of the aminotropane 15 to form a protected intermediate, which is extracted by standard procedures. The biphasic mixture of 15 is generally prepared by dissolving 15 in an aromatic diluent, such as used above, and adding an aqueous solution containing an excess of base, such as sodium hydroxide or potassium hydroxide, preferably about 2 to 5 equivalents of base.

Alternatively, the amide coupling of intermediate 15 with the carboxylic acid 14 can be performed in the presence of a coupling agent such as 1,3 dicyclohexylcarbodiimide (DCC), 1-(3-dimethylaminopropyl)-3-ethylcarbodiimide (EDC), or benzotriazol-1-yloxytripyrrolidino-phosphonium hexafluorophosphate (PyBop), optionally combined with 1-hydroxy-7-azabenzotriazole (HOAt). In yet another alternative, the amide coupling of intermediate 15 with the carboxylic acid 14 can be performed by converting 14 to an activated ester.

The protecting group $P^1$ is removed by standard procedures to provide an intermediate of formula 1. For example when the protecting group is Boc, typically removal is by treatment with an acid, such as trifluoroacetic acid, providing the acid salt of the intermediate. The acid salt of intermediate 1 can be converted to the free base, if desired, by conventional treatment with base. The protecting group Cbz, for another example, is conveniently removed by hydrogenolysis over a suitable metal catalyst such as palladium on carbon.

The protected aminotropane 15 employed in the reactions described in this application is prepared from readily available starting materials. For example, when the protecting group $P^1$ is Boc, the protected aminotropane 16 is prepared by the procedure illustrated in Scheme F.

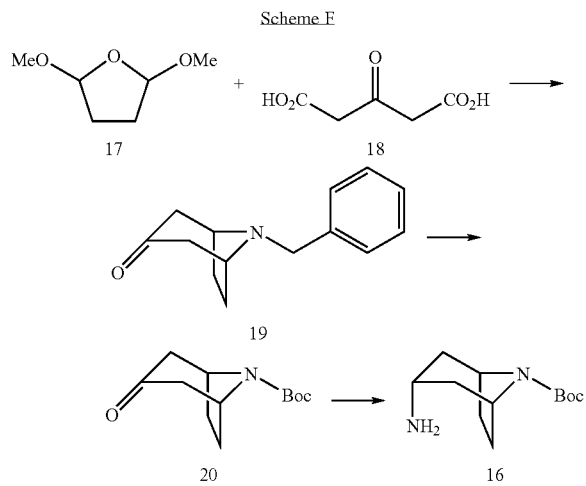

As described in detail in Example 1a below, to prepare the protected intermediate 16, first, 2,5-dimethoxy tetrahydrofuran 17 is contacted with between about 1 and 2 equivalents, preferably about 1.5 equivalents of benzyl amine and a slight excess, for example about 1.1 equivalents, of 1,3-acetonedicarboxylic acid 18 in an acidic aqueous solution in the presence of a buffering agent such as sodium hydrogen phosphate. The reaction mixture is heated to between about 60° C. and about 100° C. to ensure decarboxylation of any carboxylated intermediates in the product, 8-benzyl-8-azabicyclo[3.2.1]octan-3-one 19, commonly N-benzyltropanone.

The intermediate 19 is typically reacted with a slight excess of di-tert-butyl dicarbonate (commonly (Boc)$_2$O), for example, about 1.1 equivalents, under a hydrogen atmosphere in the presence of a transition metal catalyst to provide the Boc protected intermediate 20, 3-oxo-8-azabicyclo[3.2.1]octane-8-carboxylic acid tert-butyl ester. The reaction is typically conducted at ambient temperature for about 12 to about 72 hours. Finally, intermediate 20 is contacted with a large excess, for example at least about 25 equivalents, of ammonium formate in an inert diluent, such as methanol, in the presence of a transition metal catalyst to provide the product 16 in the endo configuration, with high stereospecificity, for example endo to exo ratio of >99:1. The reaction is typically conducted at ambient temperature for about 12 to about 72 hours or until the reaction is substantially complete. It is advantageous to add the ammonium formate reagent in portions. For example, intermediate 20 is contacted with an initial portion of ammonium formate of about 15 to about 25 equivalents. After an interval of about 12 to about 36 hours, an additional portion of about 5 to about 10 equivalents of ammonium formate is added. The subsequent addition can be repeated after a similar interval. The product 16 can be purified by conventional procedures, such as alkaline extraction.

The quinolinone carboxylic acid 14 is readily prepared by procedures similar to those reported in the literature in Suzuki et al, *Heterocycles*, 2000, 53, 2471-2485 and described in the examples below.

The oxirane intermediate 12 used in Scheme C can be prepared by reaction with a halomethyloxirane as shown in Scheme G:

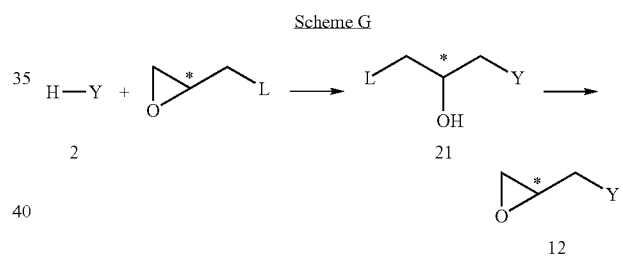

where L is a halo leaving group. This reaction is typically conducted by contacting the amine of formula 2 with between about 1 and about 2 equivalents of a halomethyloxirane in a polar diluent such as ethanol. The reaction is typically conducted at ambient temperature for between about 12 and about 24 hours, or until the reaction is substantially complete. The linear intermediate 21 is typically isolated by conventional procedures as a solid. The solid 21 is typically dissolved in an inert diluent, for example tetrahydrofuran, in the presence of a molar excess of base, for example sodium hydroxide, to produce the cyclized form 12.

The secondary amines H—Y are available commercially or are readily synthesized from common starting materials according to standard protocols described in the literature or in textbooks, such as J. March, *Advanced Organic Chemistry*, Fourth Edition, Wiley, New York, 1992, and as exemplified below.

In yet another alternative method of synthesis, compounds of formula (I) are prepared by coupling the substituted quinolinone carboxylic acid 14 with an intermediate of formula 22 as illustrated in Scheme H.

17

Scheme H

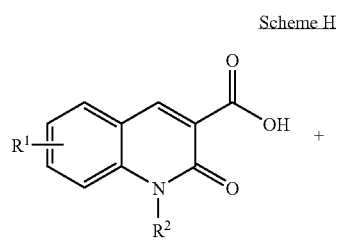

14

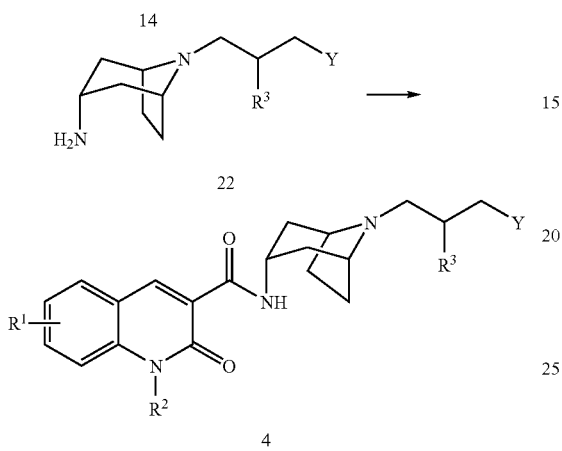

The reaction of Scheme H is typically conducted under the amide coupling conditions described above for the reaction of the carboxylic acid 14 with intermediate 15.

Intermediates of formula 22 can be prepared by deprotecting an intermediate of formula 23:

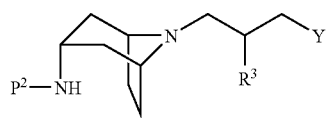

where $P^2$ represents an amino-protecting group.

Intermediates of formula 23 can be prepared from readily available starting materials using procedures analogous to the reactions described above and/or using alternative reactions well known to those skilled in the art. For example, intermediate 23 can be prepared using an intermediate 24

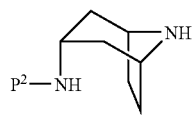

which may be formed by protecting the amino nitrogen of the aminoazobicyclooctane 15 with amino-protecting group $P^2$ and then removing $P^1$ from the nitrogen of the azabicyclooctane group. Protecting groups $P^1$ and $P^2$ are chosen such that they are removed under different conditions. For example when $P^1$ is chosen as Boc, then Cbz can be used as $P^2$. Substituting the protected aminotropane 24 for intermediate 1 in the reactions described in Schemes A, C, and D provides intermediates of formula 23.

18

Further details regarding specific reaction conditions and other procedures for preparing representative compounds of the invention or intermediates thereto are described in the examples below.

Accordingly, in a method aspect, the invention provides a process for preparing a compound of formula (I), wherein $R^1$, $R^2$, $R^3$, $R^4$, $R^5$, $R^6$, $R^7$, n, and X are defined as in formula (I), or a salt or stereoisomer thereof, the process comprising:

(a) reacting a compound of formula (VI):

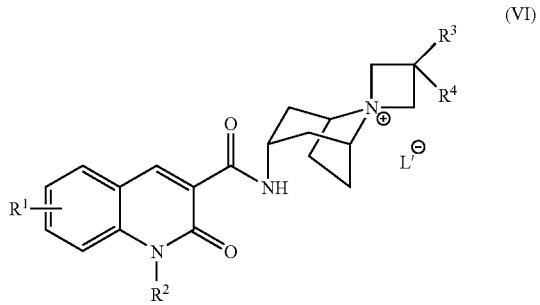

wherein L' is an anion, with a compound of formula (VIE):

or (b) reacting a compound of formula (VIII)

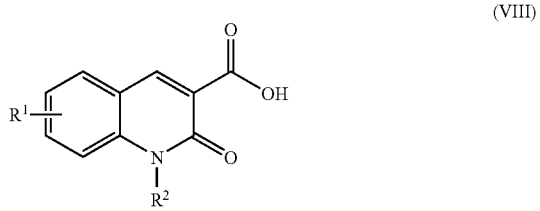

with a compound of formula (IX):

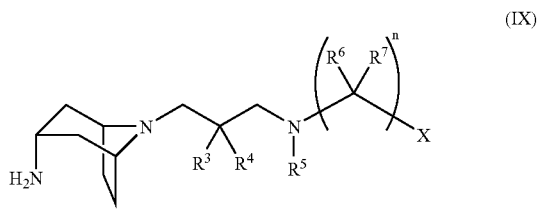

to provide a compound of formula (I), or a salt or stereoisomer thereof.

The invention also provides a process for preparing a compound of formula (I), wherein $R^3$ is hydroxy and $R^1$, $R^2$, $R^4$, $R^5$, $R^6$, $R^7$, n, and X are defined as in formula (I), or a salt or stereoisomer thereof, the process comprising:
  step (a) or step (b) as defined above, or
  (c) reacting a compound of formula (X):

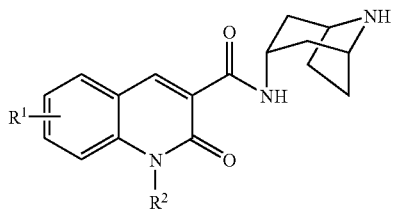

or a salt thereof, with a compound of formula (VII) and a compound of formula (XI):

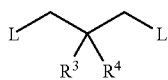

wherein L is a leaving group;
or
  (d) reacting a compound of formula (X) with a compound of formula (XII):

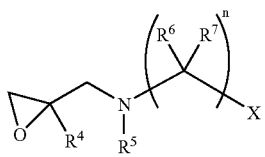

to provide a compound of formula (I), or a salt or stereoisomer thereof.

In still other aspects, this invention is directed to additional processes described herein; and to the products prepared by any of the processes described herein.

Pharmaceutical Compositions

The quinolinone-carboxamide compounds of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

Formulation Example A

Hard gelatin capsules for oral administration are prepared as follows:

| Ingredients | Amount |
| --- | --- |
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

Formulation Example B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

Formulation Example C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

Formulation Example D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

Formulation Example E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

Formulation Example F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

Formulation Example G

A suspension for oral administration is prepared as follows:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

Formulation Example H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

Formulation Example I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example J

An injectable formulation is prepared as follows:

| Ingredients | Amount |
| --- | --- |
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Formulation Example K

Capsules for oral administration are prepared as follows:

| Ingredients | Amount |
| --- | --- |
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

Formulation Example L

Capsules for oral administration are prepared as follows:

| Ingredients | Amount |
| --- | --- |
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that any form of the compounds of the invention, (i.e. free base, pharmaceutical salt, or solvate) that is suitable for the particular mode of administration, can be used in the pharmaceutical compositions discussed above.

Utility

The quinolinone-carboxamide compounds of the invention are 5-$HT_4$ receptor agonists and therefore are expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, diabetic and idiopathic gastropathy, post-operative ileus, intestinal pseudo-obstruction, and drug-induced delayed transit.

In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the compounds of the invention increase motility of the gastrointestinal (GI) tract and thus are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by 5-$HT_4$ receptors, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-$HT_4$ receptors will range from about 0.0007 to about 20 mg/kg/day of active agent, preferably from about 0.0007 to about 1 mg/kg/day. For an average 70 kg human, this would amount to from about 0.05 to about 70 mg per day of active agent.

In one aspect of the invention, the compounds of the invention are used to treat chronic constipation. When used to treat chronic constipation, the compounds of the invention will typically be administered orally in a single daily dose or in multiple doses per day. Preferably, the dose for treating chronic constipation will range from about 0.05 to about 70 mg per day.

In another aspect of the invention, the compounds of the invention are used to treat irritable bowel syndrome. When used to treat constipation-predominant irritable bowel syndrome, the compounds of the invention will typically be administered orally in a single daily dose or in multiple doses per day. Preferably, the dose for treating constipation-predominant irritable bowel syndrome will range from about 0.05 to about 70 mg per day.

In another aspect of the invention, the compounds of the invention are used to treat diabetic gastroparesis. When used to treat diabetic gastroparesis, the compounds of the invention will typically be administered orally in a single daily dose or in multiple doses per day. Preferably, the dose for treating diabetic gastroparesis will range from about 0.05 to about 70 mg per day.

In yet another aspect of the invention, the compounds of the invention are used to treat functional dyspepsia. When used to treat functional dyspepsia, the compounds of the invention will typically be administered orally in a single daily dose or in multiple doses per day. Preferably, the dose for treating functional dyspepsia will range from about 0.05 to about 70 mg per day.

The invention also provides a method of treating a mammal having a disease or condition associated with 5-HT$_4$ receptor activity, the method comprising administering to the mammal a therapeutically effective amount of a compound of the invention or of a pharmaceutical composition comprising a compound of the invention.

As described above, compounds of the invention are 5-HT$_4$ receptor agonists. The invention further provides, therefore, a method of agonizing a 5-HT$_4$ receptor in a mammal, the method comprising administering a compound of the invention to the mammal. In addition, the compounds of the invention are also useful as research tools for investigating or studying biological systems or samples having 5-HT$_4$ receptors, or for discovering new 5-HT$_4$ receptor agonists. Moreover, since compounds of the invention exhibit binding selectivity for 5-HT$_4$ receptors as compared with binding to receptors of other 5-HT subtypes, particularly 5-HT$_3$ receptors, such compounds are particularly useful for studying the effects of selective agonism of 5-HT$_4$ receptors in a biological system or sample. Any suitable biological system or sample having 5-HT$_4$ receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

In this aspect of the invention, a biological system or sample comprising a 5-HT$_4$ receptor is contacted with a 5-HT$_4$ receptor-agonizing amount of a compound of the invention. The effects of agonizing the 5-HT$_4$ receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of analogs of guanosine triphosphate (GTP), such as [$^{35}$S]GTPγS (guanosine 5'-O-(γ-thio) triphosphate) or GTP-Eu, into isolated membranes via receptor catalyzed exchange of GTP analogs for GDP analogs, ligand-mediated changes in free intracellular calcium ions (measured, for example, with a fluorescence-linked imaging plate reader or FLIPR® from Molecular Devices, Inc.), and measurement of mitogen activated protein kinase (MAPK) activation. A compound of the invention may agonize or increase the activation of 5-HT$_4$ receptors in any of the functional assays listed above, or assays of a similar nature. A 5-HT$_4$ receptor-agonizing amount of a compound of the invention will typically range from about 1 nanomolar to about 1000 nanomolar.

Additionally, the compounds of the invention can be used as research tools for discovering new 5-HT$_4$ receptor agonists. In this embodiment, 5-HT$_4$ receptor binding or functional data for a test compound or a group of test compounds is compared to the 5-HT$_4$ receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to be potent agonists of the 5-HT$_4$ receptor and to exhibit substantial selectivity for the 5-HT$_4$ receptor subtype over the 5-HT$_3$ receptor subtype in radioligand binding assays. Further, compounds of the invention of which particular mention was made have demonstrated superior pharmacokinetic properties in a rat model. Such compounds are thus expected to be highly bioavailable upon oral administration. In addition, these compounds have been shown not to exhibit an unacceptable level of inhibition of the potassium ion current in an in vitro voltage-clamp model using isolated whole cells expressing the hERG cardiac potassium channel. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, 1, 947-73, Fermini et al., *Nature Reviews Drug Discovery*, 2003, 2, 439-447) Accordingly, pharmaceutical compositions comprising these compounds of the invention are expected to have an acceptable cardiac profile.

There properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

| | |
|---|---|
| Boc = | tert-butoxycarbonyl |
| (Boc)$_2$O = | di-tert-butyl dicarbonate |
| DCM = | dichloromethane |
| DMF = | N,N-dimethylformamide |
| DMSO = | dimethyl sulfoxide |
| EtOAc = | ethyl acetate |
| mCPBA = | m-chloroperbenzoic acid |
| MeCN = | acetonitrile |
| MTBE = | tert-butyl methyl ether |
| PyBop = | benzotriazol-1-yloxytripyrrolidino-phosphonium hexafluorophosphate |
| R$_f$ = | retention factor |
| RT = | room temperature |
| TFA = | trifluoroacetic acid |
| THF = | tetrahydrofuran |

Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Mass spectrometric identification of compounds was performed by an electrospray ionization method (ESMS) with a Perkin Elmer instrument (PE SCIEX API 150 EX).

General Protocol for Analytical HPLC

Crude compounds were dissolved in 50% MeCN/H$_2$O (with 0.1% TFA) at 0.5-1.0 mg/mL concentration, and analyzed using the following conditions:

| | |
|---|---|
| Column: | Zorbax Bonus-RP (3.5 µm of particle size, 2.1 × 50 mm) |
| Flow rate: | 0.5 mL/min |
| Mobile Phases: | A = 90% MeCN/10% H$_2$O/0.1% TFA<br>B = 98% H$_2$O/2% MeCN/0.1% TFA |
| Gradient: | 10% A/90% B (0-0.5 min);<br>10% A/90% B to 50% A/50% B (linear, 0.5-5 min) |
| Detector wavelength: | 214, 254, and 280 nm. |

Alternative conditions, when used, are indicated explictly.

General Protocol for Preparative HPLC Purification

Crude compounds were dissolved in 50% acetic acid in water at 50-100 mg/mL concentration, filtered, and fractionated using the following procedure:

| | |
|---|---|
| Column: | YMC Pack-Pro C18 (50a × 20 mm; ID = 5 µm) |
| Flow rate: | 40 mL/min |
| Mobile Phases: | A = 90% MeCN/10% H$_2$O/0.1% TFA<br>B = 98% H$_2$O/2% MeCN/0.1% TFA |
| Gradient: | 10% A/90% B to 50% A/50% B over 30 min (linear) |
| Detector wavelength: | 214 nm. |

Preparation of Secondary Amines

Preparation of secondary amines not available commercially is exemplified by the following:

Thiomorpholine-1,1-dioxide was prepared from thiomorpholine by protection of the secondary amine to N-Boc thiomorpholine ((Boc)$_2$O, MeOH), oxidation to sulfone (mCPBA, CH$_2$Cl$_2$, 0° C.), and deprotection of the N-Boc group to provide the free amine (CF$_3$CO$_2$H, CH$_2$Cl$_2$). (m/z): [M+H]$^+$ calcd for C$_4$H$_9$NO$_2$S, 136.04; found, 135.9.

The N-sulfonyl derivatives of piperazine were prepared from N-Boc piperazine by reacting with respective sulfonyl chloride (iPr$_2$NEt, CH$_2$Cl$_2$, 0° C.), and deprotecting the N-Boc group (CF$_3$CO$_2$H, CH$_2$Cl$_2$). 1-Methanesulfonyl-piperazine: $^1$H-NMR (CDCl$_3$; neutral): δ (ppm) 3.1 (t, 4H), 2.9 (t, 4H), 2.7 (s, 3H). 1-(Methylsulfonyl)methanesulfonyl-piperazine: $^1$H-NMR (CD$_3$OD): δ (ppm) 2.90 (s, 3H), 3.02 (m, 4H), 3.38 (m, 4H), 4.61 (s, 2H). Methanesulfonylpiperazine was also prepared by reacting methanesulfonyl chloride with excess piperazine (>2 equivalents) in water.

The racemic or single chiral isomer forms of 3-acetylaminopyrrolidine were prepared by treating N'-Boc-3-aminopyrrolidine (racemate, 3R, or 3S) with acetyl chloride (iPr$_2$NEt, CH$_2$Cl$_2$, 0° C.), and deprotecting the N-Boc group (CF$_3$CO$_2$H, CH$_2$Cl$_2$). 3-(Acetamido)pyrrolidine: $^1$H-NMR (DMSO-d$_6$; TFA salt): δ (ppm) 4.2 (quin, 1H), 3.3-3.1 (m, 3H), 2.9 (m, 1H), 2.0 (m, 1H), 1.8 (br s, 4H).

3-((R)-2-Hydroxypropionamido)pyrrolidine was prepared after amidation of N$^1$-Boc-3-aminopyrrolidine (L-lactic acid, PyBOP, DMF, RT), and deprotection of N-Boc group (CF$_3$CO$_2$H, CH$_2$Cl$_2$). (m/z): [M+H]$^+$ calcd for C$_7$H$_{14}$N$_2$O$_2$, 159.11; found, 159.0. $^1$H-NMR (CD$_3$OD; TFA salt): δ (ppm) 4.4 (quin, 1H), 4.1 (q, 1H), 3.5-3.4 (m, 2H), 3.3-3.2 (m, 2H), 2.3 (m, 1H), 2.0 (m, 1H), 1.3 (d, 3H).

The N$^3$-alkanesulfonyl derivatives of (3R)-aminopyrrolidine were obtained by treating N$^1$-Boc-(3R)-aminopyrrolidine with propionylsulfonyl chloride or cyclohexylmethylsulfonyl chloride (i-Pr$_2$NEt, CH$_2$Cl$_2$, 0° C.), and deprotecting N-Boc group (CF$_3$CO$_2$H, CH$_2$Cl$_2$).

3-(N-Acetyl-N-methylamido)piperidine was prepared from N$^3$-Cbz protected 3-amino-piperidine-1-carboxylic acid t-butyl ester (De Costa, B., et al. *J. Med. Chem.* 1992, 35, 4334-43) after four synthetic steps: i) MeI, n-BuLi, THF, −78° C. to rt; ii) H$_2$ (1 atm), 10% Pd/C, EtOH; iii) AcCl, i-Pr$_2$NEt, CH$_2$Cl$_2$; iv) CF$_3$CO$_2$H, CH$_2$Cl$_2$. m/z: [M+H]$^+$ calcd for C$_8$H$_{16}$N$_2$O: 157.13; found, 157.2. $^1$H-NMR (CD$_3$OD; TFA salt): δ (ppm) 4.6 (m, 1H), 3.3 (m, 1H), 3.2 (m, 1H), 3.0 (m, 1H), 2.9 (s, 3H), 2.8 (m, 1H), 2.0 (s, 3H), 1.9-1.7 (m, 4H).

3-(N-Acetyl-amido)piperidine was prepared from 3-amino-piperidine-1-carboxylic acid tert-butyl ester after N-acetylation and deprotection of the N-Boc group: i) AcCl, i-Pr$_2$NEt, CH$_2$Cl$_2$; ii) CF$_3$CO$_2$H, CH$_2$Cl$_2$. $^1$H-NMR (CD$_3$OD; TFA salt): δ (ppm) 3.9 (m, 1H), 3.3 (dd, 1H), 3.2 (m, 1H), 2.9 (dt, 1H), 2.75 (dt, 1H), 2.0-1.9 (m, 2H), 1.9 (s, 3H), 1.8-1.4 (m, 2H).

The N$^3$-alkanesulfonyl derivatives of 3-aminopiperidine were synthesized by reacting the chiral or racemic forms of 3-amino-piperidine-1-carboxylxic acid tert-butyl ester with the respective alkanesulfonyl chloride (i-Pr$_2$NEt, CH$_2$Cl$_2$) and deprotecting the N-Boc group (CF$_3$CO$_2$H, CH$_2$Cl$_2$). (3S)-3-(ethanesulfonylamido)piperidine: $^1$H-NMR (CD$_3$OD): δ (ppm) 1.29(t, 3H, J$_1$=7.4 Hz), 1.50-1.80 (m, 2H), 1.90-2.10 (m, 2H), 2.89 (m, 2H), 3.05 (q, 2H, J$_1$=7.4 Hz), 3.27 (m, 2H), 3.40 (d of d(br), 1H), 3.52 (m, 1H). 3S-Methylsulfonylmethanesulfonylamido-piperidine: $^1$H-NMR (CD$_3$OD): δ (ppm) 2.13-2.30 (m, 2H), 2.40-2.57 (m, 2H), 2.98 (m, 2H), 3.15 (s, 3H), 3.21 (m, 2H), 3.30 (br d, 1H), 3.74 (m, 1H).

3-(Methylamino)-1-acetylpyrrolidine was prepared from 3-(methylamino)-1-benzylpyrrolidine (TCI America) after four steps: i) (Boc)$_2$O, MeOH, rt; ii) H$_2$ (1 atm), 10% Pd/C, EtOH; iii) AcCl, i-Pr$_2$NEt, CH$_2$Cl$_2$; iv) CF$_3$CO$_2$H, CH$_2$Cl$_2$. (m/z): [M+H]$^+$ calcd for C$_7$H$_{14}$N$_2$O: 143.12; found, 143.0.

3-(Methylamino)-1-(methanesulfonyl)pyrrolidine was prepared from 3-(methylamino)-1-benzylpyrrolidine after four steps: i) (Boc)$_2$O, MeOH, rt; ii) H$_2$ (1 atm), 10% Pd/C, EtOH; iii) CH$_3$SO$_2$Cl, i-Pr$_2$NEt, CH$_2$Cl$_2$; iv) CF$_3$CO$_2$H, CH$_2$Cl$_2$. (m/z): [M+H]$^+$ calcd for C$_6$H$_{14}$N$_2$O$_2$S: 179.08; found, 179.2. 3R-Methylamino-1-(methanesulfonyl)pyrrolidine was prepared in a similar manner from (3R)-(methylamino)-1-benzylpyrrolidine.

Derivatives of tetrahydro-3-thiophenamine-1,1-dioxide were prepared following the protocol of Loev, B. *J. Org. Chem.* 1961, 26, 4394-9 by reacting 3-sulfolene with a requisite primary amine in methanol (cat. KOH, rt). N-Methyl-3-tetrahydrothiopheneamine-1,1-dioxide (TFA salt): $^1$H-NMR (DMSO-d$_6$): δ (ppm) 9.4 (br s, 2H), 4.0-3.8 (quin, 1H), 3.6-3.5 (dd, 1H), 3.4-3.3 (m, 1H), 3.2-3.1 (m, 2H), 2.5 (s, 3H), 2.4 (m, 1H), 2.1 (m, 1H). N-2-(1-hydroxy)ethyl-3-tetrahydrothiopheneamine-1,1-dioxide: (m/z): [M+H]$^+$ calcd for C$_6$H$_{13}$NO$_3$S: 180.07; found, 180.2.

N-Methyl-tetrahydro-2H-thiopyran-4-amine-1,1-dioxide was prepared from tetrahydro-4H-thiopyran-4-one: i) MeNH$_2$, NaBH$_4$; ii) (Boc)$_2$O, MeOH; iii) mCPBA, CH$_2$Cl$_2$, 0° C.; iv) CF$_3$CO$_2$H, CH$_2$Cl$_2$. (m/z): [M+H]$^+$ calcd for C$_6$H$_{13}$NO$_2$S 164.07; found, 164.9. $^1$H-NMR (CD$_3$OD; TFA salt): δ (ppm) 3.4-3.1 (m, 5H), 2.7 (s, 3H), 2.4 (br d, 2H), 2.1 (br m, 2H).

1-Acetyl-3-(methylamino)piperidine was prepared from N³-Cbz protected 3-methylamino-piperidine: i) AcCl, i-Pr₂NEt, CH₂Cl₂; ii) H₂ (1 atm), 10% Pd/C, EtOH. ¹H-NMR (CD₃OD): δ (ppm) 4.0 (m, 1H), 3.6 (m, 1H), 3.4-3.2 (m, 2H), 3.0 (m, 1H), 2.6 (s, 3H), 2.1 (s, 3H), 1.8-1.6 (m, 4H).

1-(Methanesulfonyl)-3-(methylamino)piperidine was prepared from N³-Cbz protected 3-methylamino-piperidine: i) CH₃SO₂Cl, i-Pr₂NEt, CH₂Cl₂; ii) H₂ (1 atm), 10% Pd/C, EtOH. (m/z): [M+H]⁺ calcd for C₇H₁₆N₂O₂S 193.10; found, 193.0. ¹H-NMR (DMSO-d₆; TFA salt): δ (ppm) 3.4 (dd, 1H), 3.2 (m, 2H), 3.10 (s, 3H), 3.0-2.9 (m, 2H), 2.8 (s, 3H), 1.85-1.75 (m, 2H), 1.6-1.4 (m, 2H).

The N-derivatives of piperazine such as 1-(methoxycarbonyl)piperazine, 1-(dimethylaminocarbonyl)piperazine, and 1-(dimethylaminosulfonyl)piperazine were prepared by reacting piperazine with methylchloroformate, dimethylaminochoroformate, or dimethylaminosulfamoyl chloride, respectively.

1-Methylamino-2-methylsulfonylethane was obtained by reacting methylamine with methyl vinyl sulfone in methanol.

N-[2-(2-methoxyethylamino)ethyl], N-methyl-methanesulfonamide was synthesized starting from partially N-Boc protected ethanediamine by the following four step reaction sequence: i) methylsulfonyl chloride, triethylamine; ii) MeI, Cs₂CO₃; iii) NaH, 1-bromo-2-methoxyethane; iv) CF₃CO₂H.

Methyl 4-piperidinylcarbamate was prepared from the reaction of N'-Boc protected 4-aminopiperidine with methylchloroformate followed by the deprotection of the N-Boc group.

4-Piperidinol-dimethylcarbamate, and N-dimethyl-N'-(3-piperidinyl)urea were prepared by reacting dimethylcarbamoyl chloride with N-Boc protected 4-piperidinol or N'-Boc-3-aminopiperidine, respectively.

3-(Methylamino)-1-(dimethylaminosulfonyl)pyrrolidine was obtained by reacting 3-(N-methyl-N-Boc-amino)pyrrolidine with dimethylsulfamoyl chloride.

2-(3-Pyrrolidinyl)isothiazolidine-1,1-dioxide was synthesized by treating N'-Boc protected 3-aminopyrrolidine with 3-chloropropylsulfonyl chloride in the presence of triethylamine, and followed by deprotection of the Boc group by treatment with trifluoroacetic acid.

Preparation 1

(1S,3R,5R)-3-amino-8-azabicyclo[3.2.1]octane-8-carboxylic acid tert-butyl ester a. Preparation of 8-benzyl-8-azabicyclo[3.2.1]octan-3-one Concentrated hydrochloric acid (30 mL) was added to a heterogeneous solution of 2,5-dimethoxy tetrahydrofuran (82.2 g, 0.622 mol) in water (170 mL) while stirring. In a separate flask cooled to 0° C. (ice bath), concentrated hydrochloric acid (92 mL) was added slowly to a solution of benzyl amine (100 g, 0.933 mol) in water (350 mL). The 2,5-dimethoxytetrahydrofuran solution was stirred for approximately 20 min, diluted with water (250 mL), and then the benzyl amine solution was added, followed by the addition of a solution of 1,3-acetonedicarboxylic acid (100 g, 0.684 mol) in water (400 mL) and then the addition of sodium hydrogen phosphate (44 g, 0.31 mol) in water (200 mL). The pH was adjusted from pH 1 to pH~4.5 using 40% NaOH. The resulting cloudy and pale yellow solution was stirred overnight. The solution was then acidified to pH 3 from pH 7.5 using 50% hydrochloric acid, heated to 85° C. and stirred for 2 hours. The solution was cooled to room temperature, basified to pH 12 using 40% NaOH, and extracted with DCM (3×500 mL). The combined organic layers were washed with brine, dried (MgSO₄), filtered and concentrated under reduced pressure to produce the crude title intermediate as a viscous brown oil (52 g).

To a solution of the crude intermediate in methanol (1000 mL) was added di-tert-butyl dicarbonate (74.6 g, 0.342 mol) at 0° C. The solution was allowed to warm to room temperature and stirred overnight. The methanol was removed under reduced pressure and the resulting oil was dissolved in dichloromethane (1000 mL). The intermediate was extracted into 1 M H₃PO₄ (1000 mL) and washed with dichloromethane (3×250 mL) The aqueous layer was basified to pH 12 using aqueous NaOH, and extracted with dichloromethane (3×500 mL). The combined organic layers were dried (MgSO₄), filtered and concentrated under reduced pressure to produce the title intermediate as a viscous, light brown oil. ¹H-NMR (CDCl₃) δ (ppm) 7.5-7.2 (m, 5H, C₆H₅), 3.7 (s, 2H, CH₂Ph), 3.45 (broad s, 2H, CH-NBn), 2.7-2.6 (dd, 2H, CH₂CO), 2.2-2.1 (dd, 2H, CH₂CO), 2.1-2.0 (m, 2H, CH₂CH₂), 1.6 (m, 2H, CH₂CH₂). (m/z): [M+H]⁺ calcd for C₁₄H₁₇NO 216.14; found, 216.0.

b. Preparation of 3-oxo-8-azabicyclo[3.2.1]octane-8-carboxylic acid tert-butyl ester To a solution of 8-benzyl-8-azabicyclo[3.2.1]octan-3-one (75 g, 0.348 mol) in EtOAc (300 mL) was added a solution of di-tert-butyl dicarbonate (83.6 g, 0.383 mol, 1.1 eq) in EtOAc (300 mL). The resulting solution and rinse (100 mL EtOAc) was added to a 1 L Parr hydrogenation vessel containing 23 g of palladium hydroxide (20 wt. % Pd, dry basis, on carbon, ~50% wet with water; e.g. Pearlman's catalyst) under a stream of nitrogen. The reaction vessel was degassed (alternating vacuum and N₂ five times) and pressurized to 60 psi of H₂ gas. The reaction solution was agitated for two days and recharged with H₂ as needed to keep the H₂ pressure at 60 psi until the reaction was complete as monitored by silica thin layer chromatography. The black solution was then filtered through a pad of Celite® and concentrated under reduced pressure to yield the title intermediate quantitatively as a viscous, yellow to orange oil. It was used in the next step without further treatment. ¹H NMR (CDCl₃) δ(ppm) 4.5 (broad, 2H, CH-NBoc), 2.7 (broad, 2H, CH₂CO), 2.4-2.3 (dd, 2H, CH₂CH₂), 2.1 (broad m, 2H, CH₂CO), 1.7-1.6 (dd, 2H, CH₂CH₂), 1.5 (s, 9H, (CH₃)₃COCON)).

c. Preparation of (1S,3R,5R)-3-amino-8-azabicyclo [3.2.1]octane-8-carboxylic acid tert-butyl ester To a solution of the product of the previous step (75.4 g, 0.335 mol) in methanol (1 L) was added ammonium formate (422.5 g, 6.7 mol), water (115 mL) and 65 g of palladium on activated carbon (10% on dry basis, ~50% wet with water; Degussa type E101NE/W) under a stream of N₂ while stirring via mechanical stirrer. After 24 and 48 hours, additional portions of ammonium formate (132 g, 2.1 mol) were added each time. Once reaction progression ceased, as monitored by anal. HPLC, Celite® (>500 g) was added and the resulting thick suspension was filtered and then the collected solid was rinsed with methanol (~500 mL). The filtrates were combined and concentrated under reduced pressure until all methanol had been removed. The resulting cloudy, biphasic solution was then diluted with 1M phosphoric acid to a final volume of ~1.5 to 2.0 L at pH 2 and washed with dichloromethane (3×700 mL). The aqueous layer was basified to pH 12 using 40% aq. NaOH, and extracted with dichloromethane (3×700 mL). The combined organic layers were dried over MgSO$_4$, filtered, and concentrated by rotary evaporation, then high-vacuum leaving 52 g (70%) of the title intermediate, commonly N-Boc-endo-3-aminotropane, as a white to pale yellow solid. The isomer ratio of endo to exo amine of the product was >99 based on $^1$H-NMR analysis (>96% purity by analytical HPLC). $^1$H NMR (CDCl$_3$) δ (ppm) 4.2-4.0 (broad d, 2H, CHNBoc), 3.25 (t, 1H, CHNH$_2$), 2.1-2.05 (m, 4H), 1.9 (m, 2H), 1.4 (s, 9H, (CH$_3$)$_3$OCON), 1.2-1.1 (broad, 2H). (m/z): [M+H]$^+$ calcd for C$_{12}$H$_{22}$N$_2$O$_2$) 227.18; found, 227.2. Analytical HPLC (isocratic method; 2:98 (A:B) to 90:10 (A:B) over 5 min): retention time=3.68 min.

Preparation 2

1-isopropyl-2-oxo-1,2-dihydroquinoline-3-carboxylic acid

First, acetone (228.2 mL, 3.11 mol) was added to a stirred suspension of 2-aminophenylmethanol (255.2 g, 2.07 mol) and acetic acid (3.56 mL, 62 mmol) in water (2 L) at room temperature. After 4 h, the suspension was cooled to 0° C. and stirred for an additional 2.5 h and then filtered. The solid was collected and washed with water and the wet solid cooled and dried by lyophilisation to yield 2,2,-dimethyl-1,4-dihydro-2H-benzo[1,3]oxazine (332.2 g, 98%) as an off-white solid. $^1$H NMR (CDCl$_3$; 300 MHz): 1.48 (s, 6H, C(CH$_3$)$_2$), 4.00 (bs, 1H, NH), 4.86 (s, 2H, CH$_2$), 6.66 (d, 1H, ArH), 6.81 (t, 1H, ArH), 6.96 (d, 1H, ArH), 7.10 (t, 1H, ArH).

A solution of 2,2,-dimethyl-1,4-dihydro-2H-benzo[1,3]oxazine (125 g, 0.77 mol) in THF (1 L) was filtered through a scintillation funnel and then added dropwise via an addition funnel, over a period of 2.5 h, to a stirred solution of 1.0 M LiAlH$_4$ in THF (800 mL) at 0° C. The reaction was quenched by slow portionwise addition of Na$_2$SO$_4$.10H$_2$O (110 g), over a period of 1.5 h, at 0° C. The reaction mixture was stirred overnight, filtered and the solid salts were washed thoroughly with THF. The filtrate was concentrated under reduced pressure to yield 2-isopropylaminophenylmethanol (120 g, 95%) as a yellow oil. $^1$H NMR (CDCl$_3$; 300 MHz): 1.24 (d, 6H, CH(CH$_3$)$_2$), 3.15 (bs, 1H, OH), 3.61 (sept, 1H, CH(CH$_3$)$_2$), 4.57 (s, 2H, CH$_2$), 6.59 (t, 1H, ArH), 6.65 (d, 1H, ArH), 6.99 (d, 1H, ArH), 7.15 (t, 1H, ArH).

Manganese dioxide (85% 182.6 g, 1.79 mol) was added to a stirred solution of 2-isopropylaminophenylmethanol (118 g, 0.71 mol) in toluene (800 mL) and the reaction mixture was heated to 117° C. for 4 h. The reaction mixture was allowed to cool to room temperature overnight and then filtered through a pad of Celite which was eluted with toluene. The filtrate was concentrated under reduced pressure to yield 2-isopropylaminobenzaldehyde (105 g, 90%) as an orange oil. $^1$H NMR (CDCl$_3$; 300 MHz): 1.28 (d, 6H, CH(CH$_3$)$_2$), 3.76 (sept, 1H, CH(CH$_3$)$_2$), 6.65 (t, 1H, ArH), 6.69 (d, 1H, ArH), 7.37 (d, 1H, ArH), 7.44 (t, 1H, ArH), 9.79 (s, 1H, CHO).

2,2-Dimethyl-[1,3]dioxane-4,6-dione, commonly Meldrum's acid, (166.9 g, 1.16 mol) was added to a stirred solution of 2-isopropylaminobenzaldehyde (105 g, 0.64 mol), acetic acid (73.6 mL, 1.29 mol) and ethylenediamine (43.0 mL, 0.64 mol) in methanol (1 L) at 0° C. The reaction mixture was stirred for 1 h at 0° C. and then at room temperature overnight. The resulting suspension was filtered and the solid washed with methanol and collected to yield the title intermediate, 1-isopropyl-2-oxo-1,2-dihydroquinoline-3-carboxylic acid (146 g, 98%) as an off-white solid. $^1$H NMR (CDCl$_3$; 300 MHz): 1.72 (d, 6H, CH(CH$_3$)$_2$), 5.50 (bs, 1H, CH(CH$_3$)$_2$), 7.44 (t, 1H, ArH), 7.75-7.77 (m, 2H, ArH), 7.82 (d, 1H, ArH), 8.89 (s, 1H, CH).

Preparation 3

1-isopropyl-2-oxo-1,2-dihydroquinoline-3-carboxylic acid {(1S,3R,5R)-8-azabicyclo[3.2.1]oct-3-yl}amide a. Preparation of (1S,3R,5R)-3-[1-isopropyl-2-oxo-1,2-dihydroquinoline-3-carbonyl)amino]-8-azabicyclo[3.2.1]octane-8-carboxylic acid tert-butyl ester Thionyl chloride (36.6 mL, 0.52 mol) was added to a stirred suspension of 1-isopropyl-2-oxo-1,2-dihydroquinoline-3-carboxylic acid (80 g, 0.35 mol) in toluene (600 mL) at 85° C. and the reaction mixture then heated to 95° C. for 2 h. The reaction mixture was cooled to room temperature and then added over 25 min to a vigorously stirred biphasic solution of (1S,3R,5R)-3-amino-8-azabicyclo[3.2.1]octane-8-carboxylic acid tert-butyl ester (78.2 g, 0.35 mol) and sodium hydroxide (69.2 g, 1.73 mol) in toluene/water (1:1) (1L) at ° C. After 1 h, the layers were allowed to separate and the organic phase concentrated under reduced pressure. The aqueous phase was washed with EtOAc (1 L) and then (500 mL) and the combined organic extracts used to dissolve the concentrated organic residue. This solution was washed with 1M H$_3$PO$_4$ (500 mL), sat. aq. NaHCO$_3$ (500 mL) and brine (500 mL), dried over MgSO$_4$, filtered and concentrated under reduced pressure to yield the title intermediate (127.9 g, approx. 84%) as a yellow solid. $^1$H NMR (CDCl$_3$): 1.47 (s, 9H), 1.67 (d, 6H), 1.78-1.84 (m, 2H), 2.04-2.18 (m, 6H), 4.20-4.39 (m, 3H), 5.65 (bs, 1H), 7.26 (dd. 1H), 7.63 (m, 2H), 7.75 (dd, 1H), 8.83 (s, 1H), 10.63 (d, 1H).

b. Preparation of 1-isopropyl-2-oxo-1,2-dihydroquinoline-3-carboxylic acid {(1S,3R,5R)-8-azabicyclo[3.2.1]oct-3-yl}amide TFA (300 mL) was added to a stirred solution of the product of the previous step (127.9 g) in CH$_2$Cl$_2$ (600 mL) at 0° C. The reaction mixture was warmed to room temperature and stirred for 1 h and then concentrated under reduced pressure. The oily brown residue was then poured into a vigorously stirred solution of ether (3 L) and a solid precipitate formed immediately. The suspension was stirred overnight and then the solid collected by filtration and washed with ether to yield the title intermediate as its trifluoroacetic acid salt (131.7 g, 86% over two steps) as a light yellow solid. $^1$H NMR (CDCl$_3$): 1.68 (d, 6H), 2.10 (d, 2H), 2.33-2.39 (m, 4H), 2.44-2.61 (m, 2H), 4.08 (bs, 2H), 4.41 (m, 1H), 5.57 (bs, 1H), 7.31 (m. 1H), 7.66 (m, 2H), 7.77 (d, 1H), 8.83 (s, 1H), 9.38 (bd, 2H), 10.78 (d, 1H).

Preparation 4

3-hydroxy-3'-{[1-isopropyl-2-oxo-1,2-dihydroquinolin-3-yl)carbonyl]amino}spiro[azetidine-1,8'-(1S,3R,5R)-8-azabicyclo[3.2.1]octane 2-Bromomethyloxirane (10.72 mL, 129.5 mmol) was added to a stirred solution of 1-isopropyl-2-oxo-1,2-dihydroquinoline-3-carboxylic acid {(1S,3R,5R)-8-aza-bicyclo [3.2.1]oct-3-yl}amide trifluoroacetic acid salt (14.65 g, 43.2 mmol) in ethanol (150 mL) at room temperature. The reaction mixture was stirred for 36 h, at which time a solid precipitate formed. The solid was collected by filtration and washed with ethanol (70 mL) to yield the title intermediate as the bromide salt (8.4 g). (m/z): [M]⁺ calcd for $C_{23}H_{30}N_3O_3$ 396.23; found, 396.5. Retention time (anal. HPLC: 2-50% MeCN/H₂O over 5 min)=4.13 min.

Preparation 5

3-methoxy-31'-{[1-isopropyl-2-oxo-1,2-dihydro-quinolin-3-yl)carbonyl]amino}spiro[azetidine-1,8'-(1S,3R,5R)-8-azabicyclo[3.2.1]octane Potassium-tert-butoxide (1.63 g, 14.5 mmol) was added to a stirred suspension of 3-hydroxy-3'-{[1-isopropyl-2-oxo-1,2-dihydroquinolin-3-yl)carbonyl]amino}spiro-[azetidine-1,8'-(1S,3R,5R)-8-azabicyclo[3.2.1]octane bromide (3.45 g, 7.25 mmol) in dichloromethane (100 mL) at room temperature. After 2 min, methyl iodide (0.477 mL, 7.61 mmol) was added to the reaction mixture. After 30 min, water (2 mL) was added to quench the reaction and the reaction mixture concentrated under reduced pressure. The residue was dissolved in a minimal volume of acetic acid/water (1:1) and purified by preparative HPLC to yield the title intermediate as a trifluoroacetic acid salt (2.1 g). (m/z): [M]⁺ calcd for $C_{24}H_{32}N_3O_3$, 410.24; found 410.5. Retention time (anal. HPLC: 2-50% MeCN/H₂O over 5 min)=4.36 min.

Preparation 6

3-(methylaminocarbonyloxy)-3'-{[1-isopropyl-2-oxo-1,2-dihydroquinolin-3-yl-carbonyl]amino}spiro [azetidine-1,8'-(1S,3R,5R)-8-azabicyclo[3.2.1]octane]

Methyl isocyanate dissolved in 2.0 mL of DMF (125 mg/mL, 4.2 mmol) was added to a solution of 3-hydroxy-3'-{[1-isopropyl-2-oxo-1,2-dihydroquinolin-3-yl-carbonyl]amino}spiro[azetidine-1,8'-(1S,3R,5R)-8-aza-bicyclo[3.2.1]octane] (2.0 g, 4.2 mmol) and N,N-diisopropylethylamine (0.73 mL, 4.2 mmol) in DMF (40 mL). A catalytic amount of potassium tert-butoxide (1% by weight) was added and the mixture was stirred at room temperature for 5 h. An additional 4.2 mmol of methyl isocyanate and N,N-diisopropylethylamine were added and the reaction went to completion after stirring for an additional 16 h. The reaction mixture was concentrated under vacuum and the resultant solid was used as a crude product (2.1 g). (m/z): [M+H]⁺ calcd for $C_{25}H_{33}N_4O_4$, 453.25; found 453.2. Retention time (anal. HPLC: 10-70% MeCN/H₂O over 6 min)=2.38 min. ¹H NMR (CD₃OD): δ (ppm) 1.62 (d, 6H), 2.16 (m, 2H), 2.00(br d, 3H), 2.40-2.57 (m, 6H), 4.09 (br s, 1H), 4.17 (br s, 1H), 4.26 (q, 1H), 4.53 (br s, 1H), 5.22 (br s, 1H), 7.00 (br m, 1H), 7.25 (t, 1H), 7.69 (m, 1H), 7.80 (m, 2H), 8.69 (s, 1H), 10.90 (d, 1H).

Example 1

Synthesis of 1-isopropyl-2-oxo-1,2-dihydroquino-line-3-carboxylic acid {(1S,3R,5R)-8-[2-hydroxy-3-(4-methanesulfonylpiperazin-1-yl)propyl]-8-azabicyclo[3.2.1]oct-3-yl}amide Piperazine N-methylsulfonamide/trifluoroacetic acid salt (1.23 g, 4.41 mmol) was added to a stirred solution of 1-isopropyl-2-oxo-1,2-dihydroquinoline-3-carboxylic acid {(1S,3R, 5R)-8-azabicyclo[3.2.1]oct-3-yl}amide/trifluoroacetic acid salt (2.00 g, 4.41 mmol) and N,N-diisopropylethylamine (3.46 mL, 19.85 mmol) in methanol (50 mL). 1,3-Dibromopropanol (0.45 mL, 4.41 mmol) was subsequently added and the reaction mixture was heated to 75° C. for 16 h, at which point a further amount of piperazine sulfonamide/TFA (798 mg, 2.87 mmol) and 1,3-dibromopropanol (0.29 mL, 2.87 mmol) were added and the reaction mixture heated at 75° C. for a further 2 h. The reaction mixture was concentrated in vacuo, diluted with 50% aqueous acetic acid (8 mL) and purified by preparative HPLC (5-32% gradient) to afford the title compound (770 mg) as a white solid. (m/z): [M+H]⁺ calcd for $C_{28}H_{41}N_5O_5S$ 560.29; found, 560.2. Retention time (anal. HPLC: 2-40% MeCN/H₂O over 6 min)=4.05 min. ¹H-NMR (CD₃OD): δ (ppm) 1.62 (d, 6H), 2.16 (m, 2H), 2.40-2.57 (m, 6H), 2.89 (s, 3H), 3.16 (m, 4H), 3.38 (br s, 4H), 3.51 (br s, 4H), 4.09 (br s, 1H), 4.17 (br s, 1H), 4.26 (q, 1H), 4.53 (br s, 1H), 5.45 (br s, 1H), 7.31 (t, 1H), 7.69 (m, 1H), 7.80 (m, 2H), 8.74 (s, 1H), 11.00 (d, 1H).

Example 2

Synthesis of 1-isopropyl-2-oxo-1,2-dihydroquino-line-3-carboxylic acid ((1S,3R,5R)-8-{2-hydroxy-3-[4-(propane-2-sulfonyl)piperazin-1-yl]-propyl}-8-azabicyclo[3.2.1]oct-3-yl)amide Following the procedure of Example 1 with the substitution of piperazine N-isopropylsulfonamide for piperazine N-methylsulfonamide, the title compound was prepared. (m/z): [M+H]⁺ calcd for $C_{30}H_{45}N_5O_5S$, 588.32; found 588.4. Retention time (anal. HPLC: 5-75% MeCN/H₂O over 6 min)= 2.16 min. ¹H NMR (CD₃OD): δ (ppm) 1.22 (d, 6H), 1.62 (d, 6H), 2.16 (m, 2H), 2.40-2.57 (m, 6H), 3.08 (m, 2H), 3.38 (br s, 4H), 3.51 (br s, 4H), 4.09 (br s, 1H), 4.17 (br s, 1H), 4.26 (q, 1H), 4.41 (br s, 1H), 7.31 (t, 1H), 7.69 (m, 1H), 7.80 (m, 2H).

Example 3

Alternative synthesis of 1-isopropyl-2-oxo-1,2-dihy-droquinoline-3-carboxylic acid ((1S,3R,5R)-8-{2-hydroxy-3-[4-(propane-2-sulfonyl)-piperazin-1-yl] propyl}-8-azabicyclo[3.2.1]oct-3-yl)amide Piperazine N-isopropylsulfonamide trifluoroacetic acid salt (128 mg, 0.42 mmol) was dissolved in a solution of 3-hydroxy-3'-{[1-isopropyl-2-oxo-1,2-dihydroquinolin-3-yl-carbonyl]amino}spiro[azetidine-1,8'-(1S,3R,5R)-8-aza-bicyclo[3.2.1]octane] (100 mg, 0.21 mmol) and N,N-diisopropylethylamine (0.11 mL, 0.63 mmol) in ethanol (10 mL). The reaction mixture was shaken in a heating block at 1000C for 3 h. It was then concentrated under vacuum, diluted with 50% aqueous acetic acid (7.5 mL) and purified by preparative HPLC (2-40% gradient) to afford the title compound (93 mg) as a white solid.

Example 4

Synthesis of 1-isopropyl-2-oxo-1,2-dihydroquino-line-3-carboxylic acid {(1S,3R,5R)-8-[3-(1,1-dioxo-1λ⁶,-thiomorpholin-4-yl)-2-hydroxypropyl]-8-azabi-cyclo[3.2.1]oct-3-yl}amide Following the procedure of Example 3 with the substitution of thiomorpholine-1,1-dioxide for piperazine N-isopropylsulfonamide, the title compound was prepared. (m/z): [M+H]⁺ calcd for $C_{27}H_{38}N_4O_5S$, 531.27; found 531.3. Retention time (anal. HPLC: 2-50% MeCN/H₂O over 6 min)= 3.60 min.

Example 5

Synthesis of 1-isopropyl-2-oxo-1,2-dihydroquinoline-3-carboxylic acid {(1S,3R,5R)-8-[3-(4-acetylpiperazin-1-yl)-2-methoxypropyl]-8-azabicyclo[3.2.1]oct-3-yl}amide N-Acetylpiperazine (0.16 mmol) was dissolved in a solution of 3-methoxy-3'-{[1-isopropyl-2-oxo-1,2-dihydroquinolin-3-yl-carbonyl]amino}spiro[azetidine-1,8'-(1S,3R,5R)-8-azabicyclo[3.2.1]octane] (42 mg, 0.08 mmol) and N,N-diisopropylethyl-amine (0.056 mL, 0.32 mmol) in ethanol (1 mL). The reaction mixture was shaken in a heating block at 80° C. for 16 h. The reaction mixture was concentrated under vacuum, diluted with 50% aqueous acetic acid (1.5 mL) and purified by preparative HPLC (5-32% gradient) to afford the title compound. (m/z): [M+H]$^+$ calcd for $C_{30}H_{43}N_5O_4$, 538.34; found, 538.4. Retention time (anal. HPLC: 5-65% MeCN/H$_2$O over 4 min)=2.12 min.

Example 6

Synthesis of 1-isopropyl-2-oxo-1,2-dihydroquinoline-3-carboxylic acid {(1S,3R,5R)-8-[3-(4-methanesulfonylmethanesulfonylpiperazin-1-yl)-2-methoxypropyl]-8-azabicyclo[3.2.1]oct-3-yl}amide Following the procedure of Example 5 with the substitution of piperazine N-(1-methylsulfonyl)methanesulfonamide for N-acetylpiperazine, the title compound was prepared. (m/z): [M+H]$^+$ calcd for $C_{30}H_{45}N_5O_7S_2$, 652.29; found, 652.2. Retention time (anal. HPLC: 5-65% MeCN/H$_2$O over 4 min)=2.31 min.

Example 7

Synthesis of 1-isopropyl-2-oxo-1,2-dihydroquinoline-3-carboxylic acid {(1S,3R,5R)-8-[3-(1,1-dioxo-1λ$^6$-thiomorpholin-4-yl)-2-methoxypropyl]-8-azabicyclo[3.2.1]oct-3-yl}amide Following the procedure of Example 5 with the substitution of thiomorpholine-1,1-dioxide for N-acetylpiperazine, the title compound was prepared. (m/z): [M+H]$^+$ calcd for $C_{28}H_{40}N_4O_5S$, 545.28; found 545.2. Retention time (anal. HPLC: 5-65% MeCN/H$_2$O over 4 min)=2.53 min.

Example 8

Synthesis of 1-isopropyl-2-oxo-1,2-dihydroquinoline-3-carboxylic acid {(1S,3R,5R)-8-[(S)-2-hydroxy-3-(4-methanesulfonylpiperazin-1-yl)-propyl]-8-azabicyclo[3.2.1]oct-3-yl}amide a. Preparation of (S)-1-chloro-3-(4-methylsulfonyl-1-piperazinyl)-2-propanol (S)-Epichlorohydrin (48.0 mL, 0.612 mol) was added to a stirred solution of piperazine N-methylsulfonamide (87.3 g, 0.532 mol) in ethanol (1.33 L) at room temperature. The reaction mixture was stirred for 18 h and the white solid precipitate which formed was collected by filtration and washed with ethanol to afford (S)-1-chloro-3-(4-methylsulfonyl-1-piperazinyl)-2-propanol (107.76 g) as a white solid which was used without further purification. (m/z): [M+H]$^+$ calcd for $C_8H_{17}ClN_2O_3S$, 257.07; found, 257.2. $^1$H-NMR (DMSO): δ (ppm) 2.37 (dd, 1H), 2.45 (dd, 1H), 2.50-2.58 (m, 4H), 2.86 (s, 3H), 3.09 (m, 4H), 3.55 (dd, 1H), 3.65 (dd, 1H), 3.84 (m, 1H), 5.09 (d, 1H).

b. Preparation of (S)-1-methylsulfonyl-4-(oxiranylmethyl)piperazine

Sodium hydroxide (22.15 g, 0.534 mol) was added to a vigorously stirred solution of the product of the previous step (118.13 g, 0.461 mol) in 80% THF in water (1500 mL) at 0° C. The reaction mixture was stirred for 90 min and the layers were separated. The organic layer was concentrated under vacuum and diluted with dichloromethane (1500 mL) and washed with a mixture of the previously separated aqueous layer and 1M NaOH (500 mL). The organic layer was further washed with 1M NaOH (500 mL) and brine (500 mL), dried (MgSO$_4$), filtered and concentrated under vacuum to yield the title intermediate (90.8 g) as a white crystalline solid. The product was recrystallised from hot 1:1 mixture of EtOAc and hexane (800 mL) to yield 43.33 g of pure epoxide. (m/z): [M+H]$^+$ calcd for $C_8H_{16}N_2O_3S$, 221.10; found 221.3. $^1$H-NMR (DMSO-d$_6$): δ (ppm) 2.22 (dd, 1H), 2.45-2.60 (m, 5H), 2.69-2.75 (m, 2H), 2.87 (s, 3H), 3.02 (m, 1H), 3.11 (m, 4H).

c. Synthesis of 1-isopropyl-2-oxo-1,2-dihydroquinoline-3-carboxylic acid {(1S,3R,5R)-8-[(S)-2-hydroxy-3-(4-methanesulfonylpiperazin-1-yl)propyl]-8-azabicyclo[3.2.1]oct-3-yl}amide A suspension of (S)-1-methylsulfonyl-4-(oxiranylmethyl)piperazine (69.4 g, 0.316 mol) in ethanol (980 mL) was added to 1-isopropyl-2-oxo-1,2-dihydroquinoline-3-carboxylic acid {(1S, 3R, 5R)-8-azabicyclo[3.2.1]oct-3-yl}amide (100 g, 0.295 mol) and the reaction mixture heated at 80° C. for 18.5 h. The reaction mixture was cooled to room temperature, and concentrated under vacuum. The foamy solid was suspended in a mixture of acetonitrile and water (860 mL/940 mL), heated, and sonicated until it became homogenous. The solution was filtered while hot and the filtrate was allowed to cool to 5° C. Crystals were formed and collected by filtration to yield the title compound (122 g) as a white crystalline solid. (m/z): [M+H]$^+$ calcd for $C_{28}H_{41}N_5O_5S$, 560.29; found 560.5. Retention time (anal. HPLC: 2-40% MeCN/H$_2$O over 6 min)=4.05 min. $^1$H-NMR (CD$_3$OD, 400 MHz): δ (ppm) 1.68 (d, 6H, CH(C$\underline{H}_3$)$_2$), 1.73-1.76 (br d, 2H), 2.10 (br s, 4H, 2×CHC$\underline{H}_2$), 2.28 (m, 2H), 2.36 (dd, 1H), 2.42 (dd, 1H), 2.47-2.53 (m, 2H), 2.65 (m, 4H), 2.85 (s, 3H, SO$_2$C$\underline{H}_3$), 3.24 (t, 4H, 2×C$\underline{H}_2$SO$_2$CH$_3$), 3.29 (br s, 1H, C$\underline{H}$N), 3.36 (br s, 1H, C$\underline{H}$N), 3.86 (m, 1H, C$\underline{H}$NH), 4.19 (t, 1H, C$\underline{H}$OH), 5.50 (br s, 1H, C$\underline{H}$(CH$_3$)$_2$), 7.34 (t, 1H, Ar$\underline{H}$), 7.72 (m, 1H, Ar$\underline{H}$), 7.83 (m, 2H, 2×Ar$\underline{H}$), 8.76 (s, 1H, C=C$\underline{H}$). $^{13}$C-NMR (CD$_3$OD, 100 MHz): δ (ppm) 19.8 (q, CH(C$\underline{H}_3$)$_2$), 26.7, 26.8 (two t), 34.3 (q, SO$_2$C$\underline{H}_3$), 37.2 (t), 42.5 (d), 46.9 (t), 54.3 (t), 58.3 (t), 60.2, 60.9 (two d), 63.6 (t), 68.5 (d), 116.5 (d, CH(C$\underline{H}_3$)$_2$), 121.7, 122.4 (two s), 124.1, 132.4, 133.9 (three d), 141.4 (s), 144.7 (d), 164.0, 164.4 (two s, 2×C=O).

Example 9

Synthesis of 1-isopropyl-2-oxo-1,2-dihydroquinoline-3-carboxylic acid {(1S,3R,5R)-8-[(R)-2-hydroxy-3-(4-methanesulfonylpiperazin-1-yl)-propyl]-8-azabicyclo[3.2.1]oct-3-yl}amide a. Preparation of (R)-1-chloro-3-(4-methylsulfonyl-1-piperazinyl)-2-propanol (R)-Epichlorohydrin (3.10 mL, 39.5 mmol) was added to a stirred solution of piperazine sulfonamide trifluoroacetic acid (10.0 g, 35.9 mmol) and NN-diisopropyl-ethylamine (6.26 mL, 35.9 mmol) in ethanol (150 mL) at room temperature. The reaction mixture was stirred for 18 h and a further amount of (R)-epichlorohydrin was added (0.28 mL, 3.6 mmol) and stirred for an additional 3 h. The reaction mixture was concentrated under vacuum and the white solid was suspended in ethanol (150 mL) and stirred for 2 days. The solid was collected by filtration and washed with cold ethanol to yield (R)-1-chloro-3-(4-methylsulfonyl-1-piperazinyl)-2-propanol (5.69 g) as a white solid which was used without further purification. (m/z): [M+H]+ calcd for $C_8H_{17}ClN_2O_3S$, 257.07; found 257.2. $^1$H-NMR (DMSO-$d_6$): δ (ppm) 2.37 (dd, 1H), 2.45 (dd, 1H), 2.50-2.58 (m, 4H), 2.86 (s, 3H), 3.09 (m, 4H), 3.55 (dd, 1H), 3.65 (dd, 1H), 3.84 (m, 1H), 5.09 (d, 1H).

b. Preparation of (R)-1-methylsulfonyl-4-(oxiranylmethyl)piperazine

Sodium hydroxide (1.07 g, 26.7 mmol) was added to a vigorously stirred solution of the product of the previous step (5.69 g, 22.2 mmol) in a mixture of 80% THF in water (180 mL). The reaction mixture was stirred for 35 min, concentrated under vacuum to approximately 50 mL by volume and diluted with chloroform (200 mL) and washed with 1M NaOH (2×70 mL) and brine (70 mL). The organic layer was dried (MgSO$_4$), filtered and concentrated under vacuum to yield the title intermediate (4.35 g) as a white crystalline solid. The product was recrystallised from hot EtOAc/hexane (1:1; 800 mL) to yield pure epoxide (2.62 g). (m/z): [M+H]+ calcd for $C_8H_{16}N_2O_3S$, 221.10; found, 221.3. $^1$H-NMR (DMSO-$d_6$): δ (ppm) 2.22 (dd, 1H), 2.45-2.60 (m, 5H), 2.69-2.75 (m, 2H), 2.87 (s, 3H), 3.02 (m, 1H), 3.11 (m, 4H).

c. Synthesis of 1-isopropyl-2-oxo-1,2-dihydroquinoline-3-carboxylic acid {(1S,3R,5R)-8-[(R)-2-hydroxy-3-(4-methanesulfonylpiperazin-1-yl)propyl]-8-azabicyclo[3.2.1]oct-3-yl}amide 1-isopropyl-2-oxo-1,2-dihydroquinoline-3-carboxylic acid {(1S, 3R, 5R)-8-azabicyclo[3.2.1]oct-3-yl}amide (1.49 g, 4.38 mmol) was added to a stirred solution of (R)-1-methylsulfonyl-4-(oxiranylmethyl)piperazine (964 mg, 4.38 mmol) in toluene (20 mL) and the reaction mixture heated at 98° C. for 15 h. The reaction mixture was cooled to room temperature, concentrated under vacuum, diluted with 50% aqueous acetic acid (12 mL) and purified by preparative HPLC (5-30% gradient) to afford the title compound (492 mg) as a white solid. (m/z): [M+H]+ calcd for $C_{28}H_{41}N_5O_5S$, 560.29; found, 560.2. Retention time (anal. HPLC: 2-40% MeCN/H$_2$O over 6 min)=4.05 min. $^1$H-NMR (CD$_3$OD): δ (ppm) 1.62 (d, 6H), 2.16 (m, 2H), 2.40-2.57 (m, 6H), 2.89 (s, 3H), 3.16 (m, 4H), 3.38 (br s, 4H), 3.51 (br s, 4H), 4.09 (br s, 1H), 4.17 (br s, 1H), 4.26 (q, 1H), 4.53 (br s, 1H), 5.45 (br s, 1H), 7.31 (t, 1H), 7.69 (m, 1H), 7.80 (m, 2H), 8.74 (s, 1H), 11.00 (d, 1H).

Example 10

Synthesis of methyl-carbamic acid 2-{(1S,3R,5R)-3-[(1-isopropyl-2-oxo-1,2-dihydroquinoline-3-carbonyl)amino]-8-azabicyclo-[3.2.1]oct-8-yl}-1-(4-methanesulfonylpiperazin-1-ylmethyl)ethyl ester Piperazine N-methylsulfonamide trifluoroacetic acid salt (0.20 mmol) was added to a solution of 3-(methylaminocarbonyloxy)-3'-{[1-isopropyl-2-oxo-1,2-dihydro-quinolin-3-yl-carbonyl]amino}spiro[azetidine-1,8'-(1S,3R,5R)-8-azabicyclo[3.2.1]octane] (45.4 mg, 0.10 mmol) and N,N-diisopropylethylamine (0.087 mL, 0.50 mmol) in DMF (1 mL). The reaction mixture was shaken in a heating block at 850C for 16 h. The reaction mixture was concentrated under vacuum, diluted with 50% aqueous acetic acid (7.5 mL) and purified by preparative HPLC (2-50% gradient) to afford the title compound (24 mg) as a white solid. (m/z): [M+H]+ calcd for $C_{30}H_{44}N_6O_6S$, 617.31; found 617.2. Retention time (anal. HPLC: 2-50% MeCN/H$_2$O over 6 min)=3.82 min.

Example 11

Synthesis of methyl-carbamic acid 1-(4-dimethylcarbamoyl-piperazin-1-ylmethyl)-2-{(1S,3R,5R)-3-[(1-isopropyl-2-oxo-1,2-dihydro-quinoline-3-carbonyl)amino]-8-azabicyclo[3.2.1]oct-8-yl}ethyl ester Following the procedure of Example 10 with the substitution of 1-(dimethylcarbamoyl)piperazine for piperazine N-methylsulfonamide, the title compound was prepared. (m/z): [M+H]+ calcd for $C_{32}H_{47}N_7O_5$, 610.37; found 610.4. Retention time (anal. HPLC: 2-65% MeCN/H$_2$O over 4 min)= 2.67 min.

Example 12

Synthesis of methyl-carbamic acid 1-[3-(acetylmethylamino)-pyrrolidin-1-ylmethyl]-2-{(1S,3R,5R)-3-[(1-isopropyl-2-oxo-1,2-dihydro-quinoline-3-carbonyl)amino]-8-azabicyclo[3.2.1]oct-8-yl}ethyl ester Following the procedure of Example 10 with the substitution of 3-(N-acetyl-N-methylamino)pyrrolidine for piperazine N-methylsulfonamide, the title compound was prepared. (m/z): [M+H]+ calcd for $C_{32}H_{46}N_6O_5$, 595.36; found 595.4. Retention time (anal. HPLC: 5-65% MeCN/H$_2$O over 4 min)= 2.63 min.

Example 13

Synthesis of methyl-carbamic acid 1-(4-acetylpiperazin-1-ylmethyl)-2-{(1S,3R,5R))-3-[(1-isopropyl-2-oxo-1,2-dihydroquinoline-3-carbonyl)amino]-8-azabicyclo[3.2.1]oct-8-yl}ethyl ester Following the procedure of Example 10 with the substitution of N-acetylpiperazine for piperazine N-methylsulfonamide, the title compound was prepared. (m/z): [M+H]+ calcd for $C_{31}H_{44}N_6O_5$, 581.35; found 581.2. Retention time (anal. HPLC: 5-65% MeCN/H$_2$O over 4 min)=2.20 min.

Example 14

Synthesis of methyl-carbamic acid (R)-2-{(1S,3R,5R)-3-[(1-isopropyl-2-oxo-1,2-dihydroquinoline-3-carbonyl)amino]-8-azabicyclo-[3.2.1]oct-8-yl}-1-(4-methanesulfonylpiperazin-1-ylmethyl)ethyl ester Methyl isocyanate (41 mg, 7.1 mmol) was added to a solution of 1-isopropyl-2-oxo-1,2-dihydroquinoline-3-carboxylic acid {(1S,3R,5R)-8-[(R)-2-hydroxy-3-(4-methane-sulfonylpiperazin-1-yl)propyl]-8-azabicyclo[3.2.1]oct-3-yl}amide (Example 9) (400 mg, 0.71 mmol) in toluene (10 mL). The reaction mixture was capped and shaken in a heating block at 110° C. for 16 h. The reaction mixture was concentrated under vacuum, diluted with 50% aqueous acetic acid (7.5 mL) and purified by preparative HPLC (5-10-40% gradient) to afford the title compound (110 mg) as a white solid. (m/z): [M+H]$^+$ calcd for $C_{30}H_{44}N_6O_6S$, 617.31; found 617.4. Retention time (anal. HPLC: 10-70% MeCN/H$_2$O over 6 min)=2.40 min.

Example 15

Compounds of the Invention

Using the procedures of Examples 1-14 and variations thereof, the compounds of Tables I to XXVIII were prepared and characterized by mass spectrometry. In tables containing compounds prepared as pure stereoisomers, the chirality at the carbon atom marked with an asterisk is indicated in the column headed by an asterisk. In the compounds of Tables I to XXVIII, the quinolinone-carboxamide group is in the endo configuration with respect to the azabicyclooctane group.

TABLE I

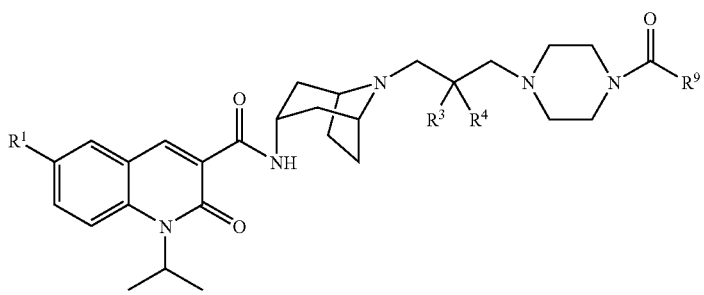

| No. | $R^1$ | $R^3$ | $R^4$ | $R^9$ | Molecular Formula | [M + H]$^+$ calcd | [M + H]$^+$ found |
|---|---|---|---|---|---|---|---|
| 1 | H | OH | H | 2-furanyl | $C_{32}H_{45}N_5O_5$ | 580.35 | 580.3 |
| 2 | H | OH | H | CH$_3$ | $C_{29}H_{41}N_5O_4$ | 524.33 | 524.4 |
| 3 | H | OH | CH$_3$ | CH$_3$ | $C_{30}H_{43}N_5O_4$ | 538.34 | 538.4 |
| 4 | H | OCH$_3$ | H | CH$_3$ | $C_{30}H_{43}N_5O_4$ | 538.34 | 538.4 |
| 5 | H | OC(O)N(CH$_3$)$_2$ | H | 2-furanyl | $C_{35}H_{50}N_6O_6$ | 651.39 | 651.4 |
| 6 | H | OC(O)N(CH$_3$)$_2$ | H | CH$_3$ | $C_{32}H_{46}N_6O_5$ | 595.36 | 595.4 |
| 7 | H | OC(O)N(CH$_3$)$_2$ | H | CH$_3$ | $C_{31}H_{44}N_6O_5$ | 581.35 | 581.2 |
| 8 | CH$_3$ | OH | H | 2-furanyl | $C_{33}H_{47}N_5O_5$ | 594.37 | 594.4 |
| 9 | CH$_3$ | OH | H | CH$_3$ | $C_{30}H_{43}N_5O_4$ | 538.34 | 538.4 |
| 10 | F | OH | H | CH$_3$ | $C_{29}H_4FN_5O_4$ | 542.32 | 542.2 |
| 11 | F | OH | H | 2-furanyl | $C_{32}H_{44}FN_5O_5$ | 598.34 | 598.4 |

TABLE II

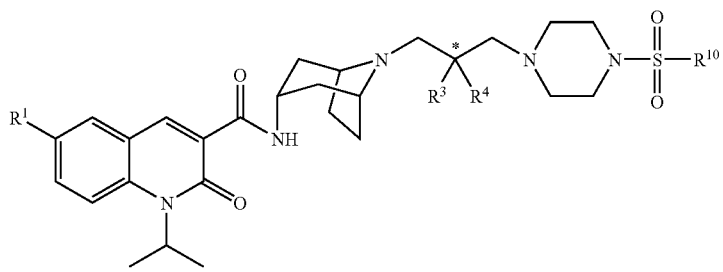

| No. | $R^1$ | $R^3$ | $R^4$ | $R^{10}$ | * | Molecular Formula | [M + H]$^+$ calcd | [M + H]$^+$ found |
|---|---|---|---|---|---|---|---|---|
| 1 | H | OH | H | CH$_3$ | | $C_{28}H_{41}N_5O_5S$ | 560.29 | 560.2 |
| 2 | H | OH | H | C$_2$H$_5$ | | $C_{29}H_{43}N_5O_5S$ | 574.31 | 574.2 |
| 3 | H | OH | H | CH$_2$cyclohexyl | | $C_{34}H_{51}N_5O_5S$ | 642.37 | 642.4 |
| 4 | H | OH | H | CH(CH$_3$)$_2$ | | $C_{30}H_{45}N_5O_5S$ | 588.32 | 588.4 |
| 5 | H | OCH$_3$ | H | CH$_3$ | | $C_{29}H_{43}N_5O_5S$ | 574.31 | 574.5 |
| 6 | H | OH | H | CH$_2$SO$_2$CH$_3$ | | $C_{29}H_{43}N_5O_7S_2$ | 638.27 | 638.2 |
| 7 | H | OH | H | CH$_3$ | R | $C_{28}H_{41}N_5O_5S$ | 560.29 | 560.5 |
| 8 | H | OH | H | CH$_3$ | S | $C_{28}H_{41}N_5O_5S$ | 560.29 | 560.5 |
| 9 | Br | OH | H | CH$_3$ | S | $C_{28}H_{40}BrN_5O_5S$ | 638.20 | 638.0 |
| 10 | H | OC(O)N(CH$_3$)$_2$ | CH$_3$ | CH$_3$ | | $C_{31}H_{46}N_6O_6S$ | 631.33 | 631.2 |
| 11 | H | OCH$_3$ | H | CH$_2$SO$_2$CH$_3$ | | $C_{30}H_{45}N_5O_7S_2$ | 652.29 | 652.2 |
| 12 | H | OH | H | CH$_2$CF$_3$ | | $C_{29}H_{40}F_3N_5O_5S$ | 628.28 | 628.2 |
| 13 | H | OC(O)NHCH$_3$ | H | CH$_3$ | | $C_{30}H_{44}N_6O_6S$ | 617.31 | 617.2 |

TABLE II-continued

| No. | R¹ | R³ | R⁴ | R¹⁰ | * | Molecular Formula | [M + H]⁺ calcd | [M + H]⁺ found |
|---|---|---|---|---|---|---|---|---|
| 14 | H | OC(O)NHCH₃ | H | CH₃ | S | $C_{30}H_{44}N_6O_6S$ | 617.31 | 617.4 |
| 15 | H | OC(O)NHCH₃ | H | CH₃ | R | $C_{30}H_{44}N_6O_6S$ | 617.31 | 617.4 |
| 16 | CH₃ | OH | H | CH₃ | | $C_{29}H_{43}N_5O_5S$ | 574.31 | 574.4 |
| 17 | F | OH | H | CH₃ | | $C_{28}H_{40}FN_5O_5S$ | 578.28 | 578.2 |
| 18 | H | CH₂OH | H | CH₃ | | $C_{29}H_{43}N_5O_5S$ | 574.31 | 574.5 |

TABLE III

| No. | R¹ | R³ | R⁴ | Molecular Formula | [M + H]⁺ calcd | [M + H]⁺ found |
|---|---|---|---|---|---|---|
| 1 | H | OH | H | $C_{27}H_{38}N_4O_5S$ | 531.27 | 531.3 |
| 2 | H | OCH₃ | H | $C_{28}H_{40}N_4O_5S$ | 545.28 | 545.2 |
| 3 | H | OC(O)N(CH₃)₂ | H | $C_{30}H_{43}N_5O_6S$ | 602.30 | 602.2 |
| 4 | H | OC(O)NHCH₃ | H | $C_{32}H_{46}N_6O_5$ | 595.36 | 595.4 |
| 5 | CH₃ | OH | H | $C_{28}H_{40}N_4O_5S$ | 545.28 | 545.2 |
| 6 | F | OCH₃ | H | $C_{27}H_{37}FN_4O_5S$ | 549.26 | 549.2 |
| 7 | H | CH₂OH | H | $C_{28}H_{40}N_4O_5S$ | 545.28 | 545.3 |

TABLE IV

| No. | R¹ | R³ | R⁴ | R¹² | Molecular Formula | [M + H]⁺ calcd | [M + H]⁺ found |
|---|---|---|---|---|---|---|---|
| 1 | H | OH | H | C₂H₅ | $C_{30}H_{43}N_5O_5$ | 554.34 | 554.3 |
| 2 | H | OH | H | CH₃ | $C_{29}H_{41}N_5O_5$ | 540.32 | 540.4 |
| 3 | H | OH | CH₃ | CH₃ | $C_{30}H_{43}N_5O_5$ | 554.34 | 554.2 |
| 4 | H | OCH₃ | H | CH₃ | $C_{30}H_{43}N_5O_5$ | 554.34 | 554.2 |
| 5 | H | OC(O)N(CH₃)₂ | H | CH₃ | $C_{32}H_{46}N_6O_6$ | 611.36 | 611.4 |
| 6 | H | OC(O)NHCH₃ | H | CH₃ | $C_{31}H_{44}N_6O_6$ | 597.34 | 597.2 |

TABLE V

| No. | R¹ | R³ | R⁴ | R¹³ | R¹⁴ | Molecular Formula | [M + H]⁺ calcd | [M + H]⁺ found |
|---|---|---|---|---|---|---|---|---|
| 1 | H | OH | H | CH₃ | CH₃ | $C_{30}H_{44}N_6O_4$ | 553.35 | 553.2 |
| 2 | H | OCH₃ | H | CH₃ | CH₃ | $C_{31}H_{46}N_6O_4$ | 567.37 | 567.4 |
| 3 | H | OC(O)N(CH₃)₂ | H | CH₃ | CH₃ | $C_{33}H_{49}N_7O_5$ | 624.39 | 624.4 |
| 4 | H | OC(O)NHCH₃ | H | CH₃ | CH₃ | $C_{32}H_{47}N_7O_5$ | 610.37 | 610.4 |
| 5 | H | OC(O)NHCH₃ | H | CH₃ | H | $C_{31}H_{45}N_7O_5$ | 596.36 | 596.2 |

TABLE V-continued

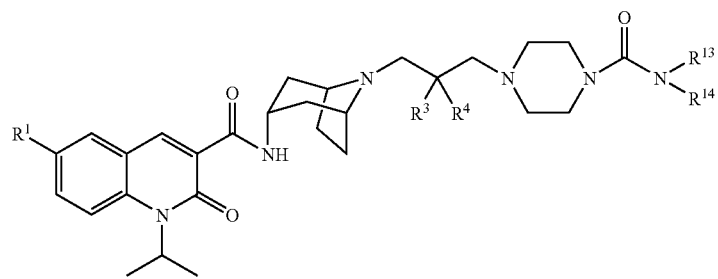

| No. | R¹ | R³ | R⁴ | R¹³ | R¹⁴ | Molecular Formula | [M + H]⁺ calcd | [M + H]⁺ found |
|---|---|---|---|---|---|---|---|---|
| 6 | H | OH | H | H | H | $C_{28}H_{40}N_6O_4$ | 525.32 | 525.2 |
| 7 | H | OH | H | CH₃ | H | $C_{29}H_{42}N_6O_4$ | 539.34 | 539.2 |
| 8 | CH₃ | OH | H | CH₃ | CH₃ | $C_{31}H_{46}N_6O_4$ | 567.37 | 567.4 |
| 9 | F | OH | H | CH₃ | CH₃ | $C_{30}H_{43}FN_6O_4$ | 571.34 | 571.4 |
| 10 | F | OH | H | CH₃ | H | $C_{29}H_{41}FN_6O_4$ | 557.31 | 557.2 |

TABLE VI

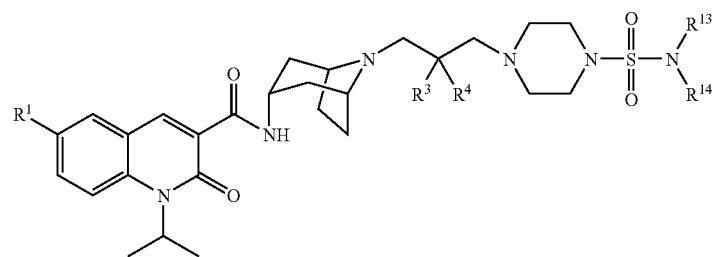

| No. | R¹ | R³ | R⁴ | R¹³ | R¹⁴ | Molecular Formula | [M + H]⁺ calcd | [M + H]⁺ found |
|---|---|---|---|---|---|---|---|---|
| 1 | H | OH | H | CH₃ | CH₃ | $C_{29}H_{44}N_6O_5S$ | 589.32 | 589.4 |
| 2 | H | OCH₃ | H | CH₃ | CH₃ | $C_{30}H_{46}N_6O_5S$ | 603.34 | 603.4 |
| 3 | H | OC(O)N(CH₃)₂ | H | CH₃ | CH₃ | $C_{32}H_{49}N_7O_6S$ | 660.36 | 660.2 |
| 4 | H | OC(O)NHCH₃ | H | CH₃ | CH₃ | $C_{31}H_{47}N_7O_6S$ | 646.34 | 646.4 |
| 5 | CH₃ | OH | H | CH₃ | CH₃ | $C_{30}H_{46}N_6O_5S$ | 603.34 | 603.4 |
| 6 | F | OCH₃ | H | CH₃ | CH₃ | $C_{29}H_{43}FN_6O_5S$ | 607.31 | 607.2 |

TABLE VII

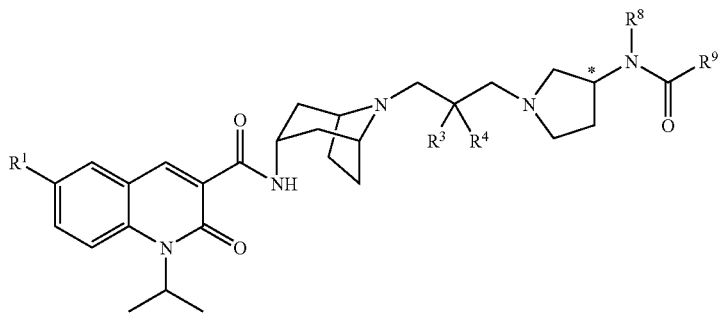

| No. | R¹ | R³ | R⁴ | R⁸ | R⁹ | * | Molecular Formula | [M + H]⁺ calcd | [M + H]⁺ found |
|---|---|---|---|---|---|---|---|---|---|
| 1 | H | OH | H | CH₃ | CH₃ | | $C_{30}H_{43}N_5O_4$ | 538.34 | 538.3 |
| 2 | H | OH | H | H | CH₃ | R | $C_{29}H_{40}N_5O_4$ | 524.33 | 524.4 |
| 3 | H | OH | H | C₂H₅ | CH₃ | | $C_{31}H_{45}N_5O_4$ | 552.36 | 552.4 |
| 4 | H | OCH₃ | H | CH₃ | CH₃ | | $C_{31}H_{45}N_5O_4$ | 552.36 | 552.3 |
| 5 | H | OH | H | H | CF₃ | R | $C_{29}H_{38}F_3N_5O_4$ | 578.30 | 578.2 |
| 6 | H | OH | H | H | CF₃ | | $C_{29}H_{38}F_3N_5O_4$ | 578.30 | 578.2 |

TABLE VII-continued

[Structure: quinolinone with R¹ substituent, carboxamide linker, azabicyclic, propyl bridge with R³ R⁴, pyrrolidine with N-R⁸ and C(O)R⁹]

| No. | R¹ | R³ | R⁴ | R⁸ | R⁹ | * | Molecular Formula | $[M+H]^+$ calcd | $[M+H]^+$ found |
|---|---|---|---|---|---|---|---|---|---|
| 7 | H | OH | H | H | CH₃ | | $C_{29}H_{41}N_5O_4$ | 524.33 | 524.4 |
| 8 | H | OH | CH₃ | C₂H₅ | CH₃ | | $C_{32}H_{47}N_5O_4$ | 566.37 | 566.4 |
| 9 | H | OH | H | H | CH(OH)CH₃ | | $C_{30}H_{43}N_5O_5$ | 554.34 | 554.4 |
| 10 | H | OCH₃ | H | H | CF₃ | S | $C_{30}H_{40}F_3N_5O_4$ | 592.31 | 592.2 |
| 11 | H | OC(O)N(CH₃)₂ | H | C₂H₅ | CH₃ | | $C_{34}H_{50}N_6O_5$ | 623.39 | 623.4 |
| 12 | H | OC(O)NHCH₃ | H | CH₃ | CH₃ | | $C_{32}H_{46}N_6O_5$ | 595.36 | 595.4 |
| 13 | CH₃ | OH | H | CH₃ | CH₃ | | $C_{31}H_{45}N_5O_4$ | 552.36 | 552.4 |
| 14 | CH₃ | OH | H | H | CH₃ | | $C_{30}H_{43}N_5O_4$ | 538.34 | 538.4 |
| 15 | F | OH | H | CH₃ | CH₃ | | $C_{30}H_{42}FN_5O_4$ | 556.33 | 556.2 |

TABLE VIII

[Structure: quinolinone with R¹ substituent, carboxamide linker, azabicyclic, propyl bridge with R³ R⁴, pyrrolidine with R⁶ₐ and N(R⁸)SO₂R¹⁰]

| No. | R¹ | R³ | R⁴ | R⁶ₐ | R⁸ | R¹⁰ | * | Molecular Formula | $[M+H]^+$ calcd | $[M+H]^+$ found |
|---|---|---|---|---|---|---|---|---|---|---|
| 1 | H | OH | H | H | H | CH₃ | R | $C_{28}H_{41}N_5O_5S$ | 560.29 | 560.2 |
| 2 | H | OH | H | H | H | C₂H₅ | R | $C_{29}H_{43}N_5O_5S$ | 574.31 | 574.3 |
| 3 | H | OH | H | H | H | CH(CH₃)₂ | R | $C_{30}H_{45}N_5O_5S$ | 588.32 | 588.2 |
| 4 | H | OH | H | H | H | CH₂SO₂CH₃ | R | $C_{29}H_{43}N_5O_7S_2$ | 638.27 | 638.2 |
| 5 | H | OH | H | H | H | CH₂cyclohexyl | R | $C_{34}H_{51}N_5O_5S$ | 642.37 | 642.3 |
| 6 | H | OH | H | H | CH₃ | CH₃ | | $C_{29}H_{43}N_5O_5S$ | 574.31 | 574.2 |
| 7 | H | OH | H | H | H | CH₃ | | $C_{28}H_{41}N_5O_5S$ | 560.29 | 560.2 |
| 8 | H | OCH₃ | H | H | CH₃ | CH₃ | | $C_{30}H_{45}N_5O_5S$ | 588.32 | 588.4 |
| 9 | H | OC(O)N(CH₃)₂ | H | H | CH₃ | CH₃ | | $C_{32}H_{48}N_6O_6S$ | 645.35 | 645.4 |
| 10 | H | OH | H | (S)-OH | CH₃ | CH₃ | S | $C_{29}H_{43}N_5O_6S$ | 590.30 | 590.2 |

TABLE IX

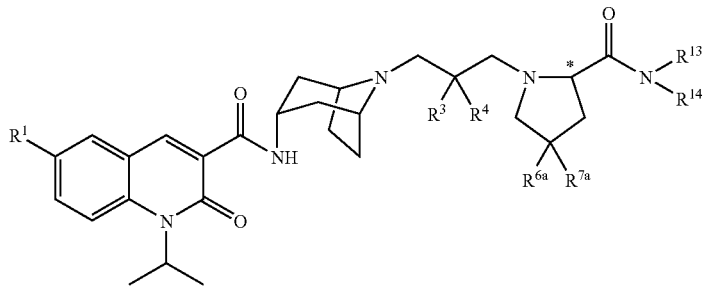

| No. | R¹ | R³ | R⁴ | R⁶ᵃ, R⁷ᵃ | R¹³ | R¹⁴ | * | Molecular Formula | [M + H]⁺ calcd | [M + H]⁺ found |
|---|---|---|---|---|---|---|---|---|---|---|
| 1 | H | OH | H | H, H | H | H | R | $C_{28}H_{39}N_5O_4$ | 510.31 | 510.3 |
| 2 | H | OH | H | H, H | $CH_3$ | $CH_3$ | S | $C_{30}H_{43}N_5O_4$ | 538.34 | 538.3 |
| 3 | H | OH | H | F, F | $C_2H_5$ | $C_2H_5$ | S | $C_{32}H_{45}F_2N_5O_4$ | 602.35 | 602.4 |
| 4 | H | OH | H | H, H | H | H | S | $C_{28}H_{39}N_5O_4$ | 510.31 | 510.4 |
| 5 | H | $OCH_3$ | H | H, H | H | H | R | $C_{29}H_{41}N_5O_4$ | 524.33 | 524.5 |
| 6 | H | OH | $CH_3$ | H, H | H | H | R | $C_{29}H_{41}N_5O_4$ | 524.33 | 524.4 |
| 7 | H | OH | $CH_3$ | H, H | $CH_3$ | $CH_3$ | R | $C_{31}H_{45}N_5O_4$ | 552.36 | 552.4 |
| 8 | H | $OC(O)N(CH_3)_2$ | H | H, H | H | H | R | $C_{31}H_{44}N_6O_5$ | 581.35 | 581.4 |
| 9 | H | $OC(O)N(CH_3)_2$ | H | H, H | $CH_3$ | $CH_3$ | S | $C_{33}H_{48}N_6O_5$ | 609.38 | 609.4 |
| 10 | H | $OC(O)NHCH_3$ | H | H, H | $CH_3$ | $CH_3$ | R | $C_{32}H_{46}N_6O_5$ | 595.36 | 595.4 |
| 11 | $CH_3$ | OH | H | H, H | H | H | S | $C_{29}H_{41}N_5O_4$ | 524.33 | 524.4 |
| 12 | $CH_3$ | OH | H | H, H | H | H | R | $C_{29}H_{41}N_5O_4$ | 524.33 | 524.4 |
| 13 | F | OH | H | H, H | H | H | R | $C_{28}H_{38}FN_5O_4$ | 528.30 | 528.2 |
| 14 | F | OH | H | H, H | H | H | S | $C_{28}H_{38}FN_5O_4$ | 528.30 | 528.2 |

TABLE X

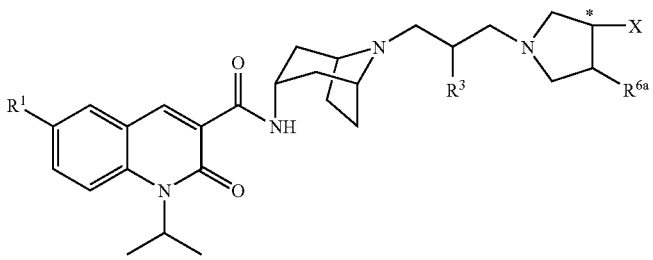

| No. | R¹ | R³ | R⁶ᵃ | X | * | Molecular Formula | [M + H]⁺ calcd | [M + H]⁺ found |
|---|---|---|---|---|---|---|---|---|
| 1 | H | OH | H | $NHC(O)OCH_3$ | | $C_{29}H_{41}N_5O_5$ | 540.32 | 540.4 |
| 2 | H | OH | H | $N(CH_3)C(O)OCH_3$ | | $C_{30}H_{43}N_5O_5$ | 554.34 | 554.2 |
| 3 | H | OH | (S) OH | $N(CH_3)C(O)OCH_3$ | S | $C_{30}H_{43}N_5O_6$ | 570.33 | 570.4 |
| 4 | H | OH | H | $OC(O)N(CH_3)_2$ | | $C_{30}H_{43}N_5O_5$ | 554.34 | 554.2 |
| 5 | F | OH | H | $OC(O)N(CH_3)_2$ | | $C_{30}H_{42}FN_5O_5$ | 572.33 | 572.2 |
| 6 | H | OH | H | $NHSO_2N(CH_3)_2$ | R | $C_{29}H_{44}N_6O_5S$ | 589.32 | 589.3 |
| 7 | H | OH | H | $N(CH_3)SO_2N(CH_3)_2$ | | $C_{30}H_{46}N_6O_5S$ | 603.34 | 603.2 |
| 8 | H | OH | H | $NHSO_2N(CH_3)_2$ | | $C_{29}H_{44}N_6O_5S$ | 589.32 | 589.2 |
| 9 | H | OH | H | $NHC(O)N(CH_3)_2$ | | $C_{30}H_{44}N_6O_4$ | 553.35 | 553.4 |
| 10 | H | OH | H | $N(CH_3)C(O)N(CH_3)_2$ | | $C_{30}H_{44}N_6O_4$ | 553.35 | 553.4 |
| 11 | H | $OCH_3$ | H | $N(CH_3)C(O)N(CH_3)_2$ | | $C_{32}H_{48}N_6O_4$ | 581.38 | 581.4 |
| 12 | H | OH | (S) OH | $N(CH_3)C(O)N(CH_3)_2$ | S | $C_{31}H_{46}N_6O_5$ | 583.36 | 583.4 |
| 13 | $CH_3$ | OH | H | $N(CH_3)C(O)N(CH_3)_2$ | | $C_{32}H_{48}N_6O_4$ | 581.38 | 581.4 |
| 14 | F | OH | H | $N(CH_3)C(O)N(CH_3)_2$ | | $C_{31}H_{45}FN_6O_4$ | 585.36 | 585.4 |
| 15 | H | OH | H | $NH_2$ | S | $C_{29}H_{43}N_5O_3$ | 510.35 | 510.3 |
| 16 | H | OH | H | $NH_2$ | R | $C_{29}H_{43}N_5O_3$ | 510.35 | 510.3 |
| 17 | H | OH | H | 2-pyridinyl | | $C_{32}H_{41}N_5O_3$ | 544.33 | 544.4 |
| 18 | H | OH | H | 1,1-dioxo-isothiazolidin-2-yl | | $C_{30}H_{43}N_5O_5S$ | 586.31 | 586.3 |

TABLE XI

| No. | R¹ | R³ | R⁴ | R¹⁵ | * | Molecular Formula | [M + H]⁺ calcd | [M + H]⁺ found |
|---|---|---|---|---|---|---|---|---|
| 1 | H | OH | H | H | S | $C_{28}H_{40}N_4O_4$ | 497.31 | 497.3 |
| 2 | H | OH | H | CH₃ | S | $C_{29}H_{42}N_4O_4$ | 511.33 | 511.3 |
| 3 | H | OC(O)N(CH₃)₂ | H | H | S | $C_{31}H_{45}N_5O_5$ | 568.35 | 568.4 |
| 4 | H | OC(O)N(CH₃)₂ | H | CH₃ | S | $C_{32}H_{47}N_5O_5$ | 582.37 | 582.4 |

TABLE XII

| No. | R¹ | R³ | R⁴ | X | Molecular Formula | [M + H]⁺ calcd | [M + H]⁺ found |
|---|---|---|---|---|---|---|---|
| 1 | H | OH | H | NHSO₂CH₃ | $C_{29}H_{43}N_5O_5S$ | 574.31 | 574.3 |
| 2 | H | OH | H | NHSO₂C₂H₅ | $C_{30}H_{45}N_5O_5S$ | 588.32 | 588.3 |
| 3 | H | OH | H | NHSO₂CH₂SO₂CH₃ | $C_{30}H_{45}N_5O_7S_2$ | 652.29 | 652.2 |
| 4 | H | OH | H | NHC(O)OCH₃ | $C_{30}H_{43}N_5O_5$ | 554.34 | 554.4 |
| 5 | F | OH | H | NHSO₂N(CH₃)₂ | $C_{30}H_{46}N_6O_5S$ | 603.34 | 603.3 |
| 6 | H | OH | H | NHC(O)N(CH₃)₂ | $C_{31}H_{46}N_6O_4$ | 567.37 | 567.4 |
| 7 | H | OH | H | NHSO₂N(CH₃)₂ | $C_{31}H_{48}N_6O_5S$ | 617.35 | 617.4 |

TABLE XIII

| No. | R¹ | R³ | R⁴ | R⁶ᵃ, R⁷ᵃ | R¹³ | R¹⁴ | Molecular Formula | [M + H]⁺ calcd | [M + H]⁺ found |
|---|---|---|---|---|---|---|---|---|---|
| 1 | H | OH | H | F, F | C₂H₅ | C₂H₅ | $C_{33}H_{47}F_2N_5O_4$ | 616.37 | 616.4 |
| 2 | H | OH | H | H, H | H | H | $C_{29}H_{41}N_5O_4$ | 524.33 | 524.2 |
| 3 | H | OCH₃ | H | H, H | H | H | $C_{30}H_{43}N_5O_4$ | 538.34 | 538.4 |
| 4 | H | OC(O)N(CH₃)₂ | H | H, H | C₂H₅ | C₂H₅ | $C_{36}H_{54}N_6O_5$ | 651.43 | 651.4 |
| 5 | H | OC(O)N(CH₃)₂ | H | H, H | H | H | $C_{32}H_{46}N_6O_5$ | 595.36 | 595.4 |

TABLE XIII-continued

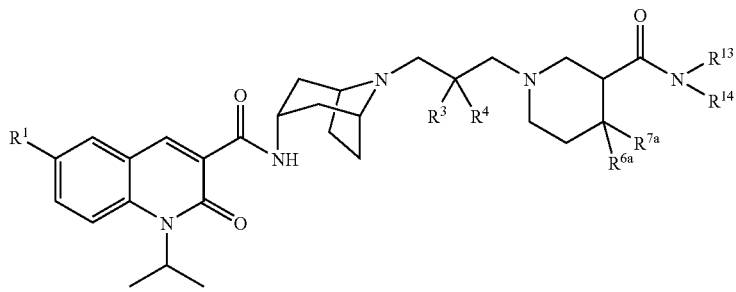

| No. | R¹ | R³ | R⁴ | R⁶ᵃ, R⁷ᵃ | R¹³ | R¹⁴ | Molecular Formula | [M + H]⁺ calcd | [M + H]⁺ found |
|---|---|---|---|---|---|---|---|---|---|
| 6 | CH₃ | OH | H | H, H | H | H | $C_{30}H_{43}N_5O_4$ | 538.34 | 538.4 |
| 7 | F | OH | H | H, H | H | H | $C_{29}H_{40}FN_5O_4$ | 542.32 | 542.2 |
| 8 | H | CH₂OH | H | H, H | H | H | $C_{30}H_{43}N_5O_4$ | | |

TABLE XIV

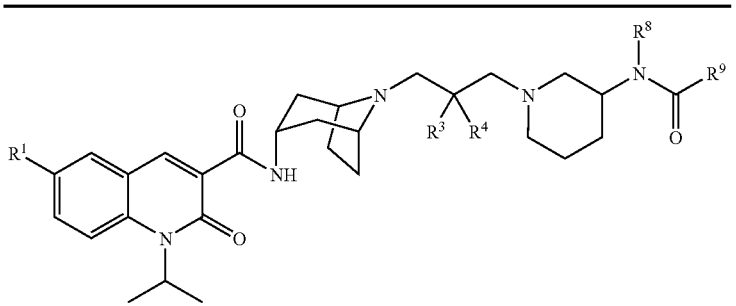

| No. | R¹ | R³ | R⁴ | R⁸ | R⁹ | Molecular Formula | [M + H]⁺ calcd | [M + H]⁺ found |
|---|---|---|---|---|---|---|---|---|
| 1 | H | OH | H | H | CH₃ | $C_{30}H_{43}N_5O_4$ | 538.34 | 538.4 |
| 2 | H | OH | H | CH₃ | CH₃ | $C_{31}H_{45}N_5O_4$ | 552.36 | 552.4 |
| 3 | H | OCH₃ | H | CH₃ | CH₃ | $C_{32}H_{47}N_5O_4$ | 566.37 | 566.4 |
| 4 | H | OC(O)N(CH₃)₂ | H | CH₃ | CH₃ | $C_{34}H_{50}N_6O_5$ | 623.39 | 623.4 |
| 5 | CH₃ | OH | H | CH₃ | CH₃ | $C_{32}H_{47}N_5O_4$ | 566.37 | 566.4 |
| 6 | F | OH | H | CH₃ | CH₃ | $C_{31}H_{44}FN_5O_4$ | 570.35 | 570.4 |

TABLE XV

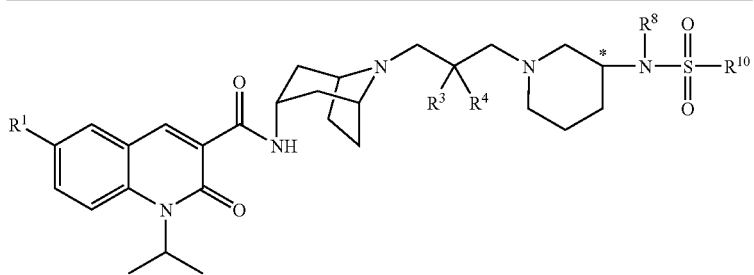

| No. | R¹ | R³ | R⁴ | R⁸ | R¹⁰ | * | Molecular Formula | [M + H]⁺ calcd | [M + H]⁺ found |
|---|---|---|---|---|---|---|---|---|---|
| 1 | H | OH | H | H | CH₃ | S | $C_{29}H_{43}N_5O_5S$ | 574.31 | 574.2 |
| 2 | H | OH | H | H | C₂H₅ | S | $C_{30}H_{45}N_5O_5S$ | 588.32 | 588.3 |
| 3 | H | OH | H | H | CH₂SO₂CH₃ | S | $C_{30}H_{45}N_5O_7S_2$ | 652.29 | 652.2 |
| 4 | H | OH | H | CH₃ | CH₃ | | $C_{30}H_{45}N_5O_5S$ | 588.32 | 588.4 |
| 5 | H | OH | H | H | CH(CH₃)₂ | S | $C_{31}H_{47}N_5O_5S$ | 602.34 | 602.2 |

TABLE XV-continued

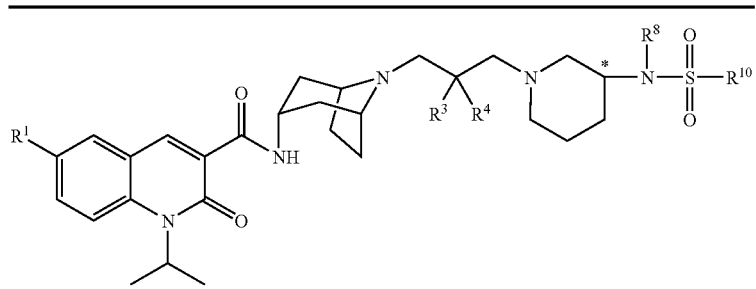

| No. | $R^1$ | $R^3$ | $R^4$ | $R^8$ | $R^{10}$ | * | Molecular Formula | $[M+H]^+$ calcd | $[M+H]^+$ found |
|---|---|---|---|---|---|---|---|---|---|
| 6 | $CH_3$ | OH | H | $CH_3$ | $CH_3$ | | $C_{31}H_{47}N_5O_5S$ | 602.34 | 602.4 |
| 7 | F | OH | H | $CH_3$ | $CH_3$ | | $C_{30}H_{44}FN_5O_5S$ | 606.31 | 606.2 |

TABLE XVI

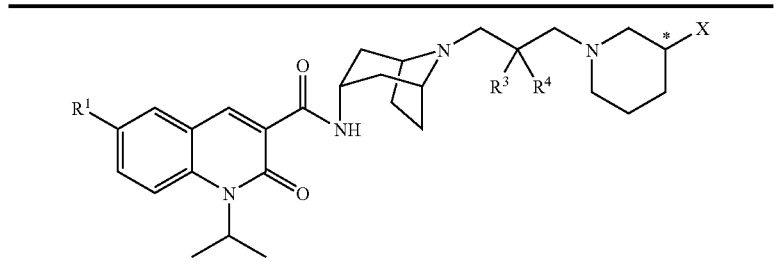

| No. | $R^1$ | $R^3$ | $R^4$ | X | * | Molecular Formula | $[M+H]^+$ calcd | $[M+H]^+$ found |
|---|---|---|---|---|---|---|---|---|
| 1 | H | OH | H | $N(CH_3)SO_2N(CH_3)_2$ | S | $C_{30}H_{46}N_6O_5S$ | 603.34 | 603.3 |
| 2 | H | OH | H | $NHSO_2N(CH_3)_2$ | | $C_{31}H_{48}N_6O_5S$ | 617.35 | 617.4 |
| 3 | H | OH | H | $NHC(O)N(CH_3)_2$ | | $C_{31}H_{46}N_6O_4$ | 567.37 | 567.4 |
| 4 | H | OH | H | $N(CH_3)C(O)N(CH_3)_2$ | | $C_{32}H_{48}N_6O_4$ | 581.38 | 581.4 |
| 5 | H | OH | H | $NHC(O)OCH_3$ | | $C_{30}H_{43}N_5O_5$ | 554.34 | 554.4 |
| 6 | H | OH | H | $N(CH_3)C(O)OCH_3$ | | $C_{31}H_{45}N_5O_5$ | 568.35 | 568.4 |
| 7 | F | OH | H | $N(CH_3)C(O)OCH_3$ | | $C_{31}H_{44}FN_5O_5$ | 586.34 | 586.4 |
| 8 | H | OH | H | $OC(O)N(CH_3)_2$ | | $C_{31}H_{45}N_5O_5$ | 568.35 | 568.4 |
| 9 | H | $OCH_3$ | H | $OC(O)N(CH_3)_2$ | | $C_{32}H_{47}N_5O_4$ | 566.37 | 566.4 |
| 10 | $CH_3$ | OH | H | $OC(O)N(CH_3)_2$ | | $C_{32}H_{47}N_5O_5$ | 582.37 | 582.4 |

TABLE XVII

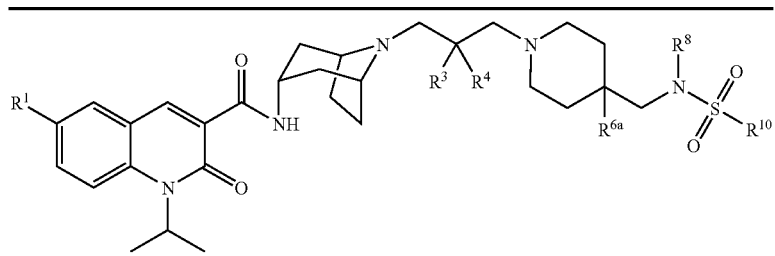

| No. | $R^1$ | $R^3$ | $R^4$ | $R^{6a}$ | $R^8$ | $R^{10}$ | Molecular Formula | $[M+H]^+$ calcd | $[M+H]^+$ found |
|---|---|---|---|---|---|---|---|---|---|
| 1 | H | OH | H | H | H | $CH_3$ | $C_{30}H_{45}N_5O_5S$ | 588.78 | 588.3 |
| 2 | H | OH | H | OH | H | $CH_3$ | $C_{30}H_{45}N_5O_6S$ | 604.32 | 604.2 |
| 3 | H | OH | H | H | $CH_3$ | $CH_3$ | $C_{31}H_{47}N_5O_5S$ | 602.34 | 602.3 |
| 4 | H | $OC(O)N(CH_3)_2$ | H | H | H | $CH_3$ | $C_{33}H_{50}N_6O_6S$ | 659.36 | 659.4 |
| 5 | H | $OC(O)NHCH_3$ | H | H | H | $CH_3$ | $C_{32}H_{48}N_6O_6S$ | 645.35 | 645.4 |
| 6 | $CH_3$ | OH | H | H | H | $CH_3$ | $C_{31}H_{47}N_5O_5S$ | 602.34 | 602.4 |
| 7 | F | OH | H | H | H | $CH_3$ | $C_{30}H_{44}FN_5O_5S$ | 606.31 | 606.2 |

TABLE XVIII

| No. | R¹ | R³ | R⁴ | X | Molecular Formula | [M + H]⁺ calcd | [M + H]⁺ found |
|---|---|---|---|---|---|---|---|
| 1 | H | OH | H | OH | $C_{28}H_{40}N_4O_4$ | 497.31 | 497.3 |
| 2 | H | OH | H | pyrrolidin-1-yl-2-one | $C_{32}H_{45}N_5O_4$ | 564.36 | 564.3 |
| 3 | H | OH | H | C(O)NH₂ | $C_{29}H_{41}N_5O_4$ | 524.33 | 524.3 |
| 4 | H | OH | H | pyrrolidin-1-yl | $C_{32}H_{47}N_5O_3$ | 550.38 | 550.4 |
| 5 | H | OH | H | N(CH₃)SO₂CH₃ | $C_{30}H_{45}N_5O_5S$ | 588.32 | 588.3 |
| 6 | H | OH | H | NHSO₂CH₃ | $C_{28}H_{41}N_5O_5S$ | 560.29 | 560.5 |
| 7 | H | OH | H | (CH₂)₂OH | $C_{30}H_{44}N_4O_4$ | 525.35 | 525.4 |
| 8 | H | OC(O)N(CH₃)₂ | H | OH | $C_{31}H_{45}N_5O_5$ | 568.35 | 568.4 |
| 9 | H | OC(O)N(CH₃)₂ | H | pyrrolidin-1-yl-2-one | $C_{35}H_{50}N_6O_5$ | 635.39 | 635.4 |
| 10 | H | CH₂OH | H | OH | $C_{29}H_{42}N_4O_4$ | 511.33 | 511.5 |
| 11 | H | CH₂OH | H | N(CH₃)SO₂CH₃ | $C_{31}H_{47}N_5O_5S$ | 602.34 | 602.8 |

TABLE XIX

| No. | R¹ | R³ | R⁴ | X' | Molecular Formula | [M + H]⁺ calcd | [M + H]⁺ found |
|---|---|---|---|---|---|---|---|
| 1 | H | OH | H | (CH₂)₂OH | $C_{30}H_{44}N_4O_4$ | 525.35 | 525.4 |
| 2 | H | OH | H | CH₂OH | $C_{29}H_{42}N_4O_4$ | 511.33 | 511.4 |
| 3 | H | OH | H | C(O)NH₂ | $C_{29}H_{41}N_5O_4$ | 524.33 | 525.2 |
| 4 | H | OC(O)NHCH₃ | H | C(O)NH₂ | $C_{31}H_{44}N_6O_5$ | 581.35 | 581.4 |
| 5 | H | OC(O)N(CH₃)₂ | H | CH₂OH | $C_{32}H_{47}N_5O_5$ | 582.37 | 582.4 |

TABLE XX

| No. | R¹ | R³ | R⁴ | R¹⁶ | Molecular Formula | [M + H]⁺ calcd | [M + H]⁺ found |
|---|---|---|---|---|---|---|---|
| 1 | H | OH | H | (CH₂)₂OH | $C_{29}H_{43}N_5O_4$ | 526.34 | 526.3 |
| 2 | H | OH | H | (CH₂)₂O(CH₂)₂OH | $C_{31}H_{47}N_5O_5$ | 570.37 | 570.3 |

TABLE XX-continued

| No. | R¹ | R³ | R⁴ | R¹⁶ | Molecular Formula | [M + H]⁺ calcd | [M + H]⁺ found |
|---|---|---|---|---|---|---|---|
| 3 | H | OH | H | CH₂C(O)-4-morpholinyl | $C_{33}H_{48}N_6O$ | 609.38 | 609.4 |
| 4 | H | OH | H | 4-pyridinyl | $C_{32}H_{42}N_6O_3$ | 559.34 | 559.3 |
| 5 | H | OH | H | CH₂-4-pyridinyl | $C_{33}H_{44}N_6O_3$ | 573.36 | 573.3 |
| 6 | H | OH | H | CH₂-2-tetrahydrofuranyl | $C_{32}H_{47}N_5O_4$ | 566.37 | 566.3 |
| 7 | H | OH | H | (CH₂)₂-4-morpholinyl | $C_{33}H_{50}N_6O_4$ | 595.40 | 595.4 |
| 8 | H | OH | H | CH₂C(O)N(CH₃)₂ | $C_{31}H_{46}N_6O_4$ | 567.37 | 567.3 |
| 9 | H | OH | H | 2-pyridinyl | $C_{32}H_{42}N_6O_3$ | 559.34 | 559.4 |

TABLE XXI

| No. | R¹ | R³ | R⁴ | R⁵ | X' | * | Molecular Formula | [M + H]⁺ calcd | [M + H]⁺ found |
|---|---|---|---|---|---|---|---|---|---|
| 1 | H | OH | H | CH₃ | NSO₂C₂H₅ | | $C_{30}H_{45}N_5O_5S$ | 588.32 | 588.2 |
| 2 | H | OH | H | CH₃ | NSO₂CH₃ | | $C_{29}H_{43}N_5O_5S$ | 574.31 | 574.2 |
| 3 | H | OH | H | CH₃ | NC(O)OCH₃ | | $C_{30}H_{43}N_5O_5$ | 554.34 | 554.4 |
| 4 | H | OH | H | CH₃ | NC(O)N(CH₃)₂ | | $C_{31}H_{46}N_6O_4$ | 567.37 | 567.6 |
| 5 | H | OCH₃ | H | CH₃ | NC(O)N(CH₃)₂ | | $C_{32}H_{48}N_6O_4$ | 581.38 | 581.4 |
| 6 | H | OH | H | CH₃ | NC(O)CH₃ | | $C_{30}H_{43}N_5O_4$ | 538.34 | 538.2 |
| 7 | H | OH | H | CH₃ | NSO₂N(CH₃)₂ | | $C_{30}H_{46}N_6O_5S$ | 603.34 | 603.2 |
| 8 | H | OC(O)NHCH₃ | H | CH₃ | NC(O)CH₃ | | $C_{32}H_{46}N_6O_6$ | 611.36 | 611.4 |
| 9 | CH₃ | OH | H | CH₃ | NSO₂N(CH₃)₂ | | $C_{31}H_{45}N_5O_4$ | 552.36 | 552.4 |
| 10 | CH₃ | OH | H | CH₃ | NSO₂CH₃ | R | $C_{30}H_{45}N_5O_5S$ | 588.32 | 588.4 |
| 11 | CH₃ | OH | H | CH₃ | NSO₂CH₃ | | $C_{30}H_{45}N_5O_5S$ | 588.32 | 588.4 |

TABLE XXII

| No. | R¹ | R³ | R⁴ | R⁵ | * | Molecular Formula | [M + H]⁺ calcd | [M + H]⁺ found |
|---|---|---|---|---|---|---|---|---|
| 1 | H | OH | H | CH₃ | | $C_{28}H_{40}N_4O_5S$ | 545.28 | 545.2 |
| 2 | H | OCH₃ | H | CH₃ | | $C_{29}H_{42}N_4O_5S$ | 559.30 | 559.2 |
| 3 | H | OC(O)N(CH₃)₂ | H | CH₃ | | $C_{31}H_{45}N_5O_6S$ | 616.32 | 616.2 |

TABLE XXII-continued

| No. | R¹ | R³ | R⁴ | R⁵ | * | Molecular Formula | [M + H]⁺ calcd | [M + H]⁺ found |
|---|---|---|---|---|---|---|---|---|
| 4 | H | OH | H | CH₂CH₂OH | | $C_{29}H_{42}N_4O_6S$ | 575.29 | 575.2 |
| 5 | H | OH | H | CH₃ | R | $C_{29}H_{43}N_5O_5S$ | 574.31 | 574.2 |
| 6 | CH₃ | OH | H | CH₃ | | $C_{29}H_{42}N_4O_5S$ | 559.30 | 559.2 |
| 7 | F | OH | H | CH₃ | | $C_{28}H_{39}FN_4O_5S$ | 563.27 | 563.2 |

TABLE XXIII

| No. | R¹ | R³ | R⁴ | R⁵ | V | Molecular Formula | [M + H]⁺ calcd | [M + H]⁺ found |
|---|---|---|---|---|---|---|---|---|
| 1 | H | OH | H | CH₃ | C(O)CH₃ | $C_{31}H_{45}N_5O_4$ | 552.36 | 552.4 |
| 2 | H | OH | H | CH₃ | C(O)OCH₃ | $C_{31}H_{45}N_5O_5$ | 568.35 | 568.4 |
| 3 | H | OH | H | CH₃ | SO₂CH₃ | $C_{30}H_{45}N_5O_5S$ | 588.32 | 588.4 |
| 4 | H | OH | H | CH₃ | C(O)N(CH₃)₂ | $C_{32}H_{48}N_6O_4$ | 581.38 | 581.4 |
| 5 | H | OH | H | CH₃ | SO₂N(CH₃)₂ | $C_{31}H_{48}N_6O_5S$ | 617.35 | 617.4 |

TABLE XXIV

| No. | R¹ | R³ | R⁴ | R⁵ | Molecular Formula | [M + H]⁺ calcd | [M + H]⁺ found |
|---|---|---|---|---|---|---|---|
| 1 | H | OH | H | CH₃ | $C_{29}H_{42}N_4O_5S$ | 559.30 | 559.2 |
| 2 | CH₃ | OH | H | CH₃ | $C_{30}H_{44}N_4O_5S$ | 573.31 | 573.4 |
| 3 | F | OH | H | CH₃ | $C_{29}H_{41}FN_4O_5S$ | 577.29 | 577.2 |

TABLE XXV

| No. | R¹ | R³ | X' | Molecular Formula | [M + H]⁺ calcd | [M + H]⁺ found |
|---|---|---|---|---|---|---|
| 1 | H | OH | NSO₂CH₃ | $C_{29}H_{43}N_5O_5S$ | 574.31 | 574.7 |
| 2 | H | OH | NC(O)CH₃ | $C_{30}H_{43}N_5O_4$ | 538.34 | 538.2 |
| 3 | CH₃ | OH | NC(O)CH₃ | $C_{31}H_{45}N_5O_4$ | 552.36 | 552.4 |
| 4 | CH₃ | OH | NSO₂CH₃ | $C_{30}H_{45}N_5O_5S$ | 588.32 | 588.4 |
| 5 | F | OH | NC(O)CH₃ | $C_{30}H_{42}FN_5O_4$ | 556.33 | 556.4 |
| 6 | F | OH | NSO₂CH₃ | $C_{29}H_{42}FN_5O_5S$ | 592.30 | 592.2 |

TABLE XXVI

| No | R¹ | R³ | R⁴ | R⁵ | Z | Molecular Formula | $[M+H]^+$ calcd | $[M+H]^+$ found |
|---|---|---|---|---|---|---|---|---|
| 1 | H | OH | H | CH₃ | (CH₂)₃NHSO₂CH₃ | $C_{28}H_{43}N_5O_5S$ | 562.31 | 562.3 |
| 2 | H | OH | H | CH₃ | CH₂CH₂OH | $C_{26}H_{38}N_4O_4$ | 471.30 | 471.3 |
| 3 | H | OH | H | CH₃ | (CH₂)₂N(CH₃)₂ | $C_{28}H_{43}N_5O_3$ | 498.35 | 498.3 |
| 4 | H | OH | H | CH₃ | CH₂C(O)N(CH₃)₂ | $C_{28}H_{41}N_5O_4$ | 512.33 | 512.3 |
| 5 | H | OH | H | CH₃ | (CH₂)₂-2-pyridinyl | $C_{31}H_{41}N_5O_3$ | 532.33 | 532.3 |
| 6 | H | OH | H | CH₃ | (CH₂)₂CN | $C_{27}H_{37}N_5O_3$ | 480.30 | 480.2 |
| 7 | H | OH | H | CH₃ | CH₂C(O)NH₂ | $C_{26}H_{37}N_5O_4$ | 484.29 | 484.2 |
| 8 | H | OH | H | CH₂CH₂OH | CH₂CH₂OH | $C_{27}H_{40}N_4O_5$ | 501.34 | 501.4 |
| 9 | H | OH | H | CH₂CH₂OCH₃ | CH₂CH₂OCH₃ | $C_{29}H_{44}N_4O_5$ | 529.34 | 529.4 |
| 10 | H | OH | H | CH₂CH₃ | CH₂-4-pyridinyl | $C_{31}H_{41}N_5O_3$ | 532.33 | 532.4 |
| 11 | H | OH | H | CH₃ | (CH₂)₂-3-indolyl | $C_{34}H_{43}N_5O_3$ | 570.35 | 570.4 |
| 12 | H | OH | H | CH₃ | (CH₂)₂SO₂CH₃ | $C_{27}H_{40}N_4O_5S$ | 533.28 | 533.2 |
| 13 | H | OH | H | CH₃ | CH₂CN | $C_{27}H_{36}N_4O_3$ | 465.29 | 465.2 |
| 14 | H | OH | H | CH₃ | (CH₂)₂OCH₃ | $C_{27}H_{40}N_4O_4$ | 485.31 | 485.2 |
| 15 | H | OH | H | CH₃ | CH₂CN | $C_{25}H_{33}N_5O_3$ | 452.27 | 452.0 |
| 16 | H | OH | H | CH₂CN | CH₂CN | $C_{27}H_{34}N_6O_3$ | 491.28 | 491.4 |
| 17 | H | OH | H | CH₃ | (CH₂)₂CN | $C_{28}H_{39}N_5O_3$ | 494.32 | 494.3 |
| 18 | H | OH | H | CH₃ | (CH₂)₂N(CH₃)C(O)N(CH₃)₂ | $C_{30}H_{46}N_6O_4$ | 555.37 | 555.4 |
| 19 | H | OH | H | CH₃ | (CH₂)₂N(CH₃)C(O)OCH₃ | $C_{29}H_{41}N_5O_5$ | 542.34 | 542.4 |
| 20 | H | OH | H | CH₂CH₂OH | (CH₂)₂N(CH₃)SO₂CH₃ | $C_{29}H_{44}N_5O_6S$ | 592.32 | 592.4 |
| 21 | H | OH | H | CH₂CH₂OCH₃ | (CH₂)₂N(CH₃)SO₂CH₃ | $C_{30}H_{47}N_5O_6S$ | 606.33 | 606.4 |
| 22 | H | OH | H | CH₃ | (CH₂)₂NHSO₂CH₃ | $C_{27}H_{41}N_5O_5S$ | 548.29 | 548.4 |
| 23 | H | OH | H | H | (CH₂)₂NHSO₂CH₃ | $C_{26}H_{39}N_5O_5S$ | 534.28 | 534.2 |
| 24 | H | OH | H | CH₃ | (CH₂)₂N(CH₃)SO₂CH₃ | $C_{28}H_{43}N_5O_5S$ | 562.31 | 562.2 |
| 25 | H | OH | H | H | (S)-CH₂-2-tetrahydrofuranyl | $C_{28}H_{40}N_4O_4$ | 497.31 | 497.2 |
| 26 | H | OH | H | H | (CH₂)₂OCH₃ | $C_{26}H_{38}N_4O_4$ | 471.30 | 471.2 |
| 27 | H | OH | H | H | CH₂CF₃ | $C_{25}H_{33}F_3N_4O_3$ | 495.26 | 495.2 |
| 28 | H | OH | H | H | (CH₂)₃-1-imidazolyl | $C_{29}H_{40}N_6O_3$ | 521.33 | 521.2 |
| 29 | H | OH | H | H | (CH₂)₂SCH₂CH₃ | $C_{27}H_{40}N_4O_3S$ | 501.29 | 501.2 |
| 30 | H | OH | H | H | CH₂CN | $C_{26}H_{34}N_4O_3$ | 451.27 | 451.2 |
| 31 | H | OH | H | H | (CH₂)₂-3-indolyl | $C_{33}H_{41}N_5O_3$ | 556.33 | 556.2 |
| 32 | H | OH | H | H | (CH₂)₂OCH₂CH₂OH | $C_{27}H_{40}N_4O_5$ | 501.31 | 501.2 |
| 33 | H | OH | H | H | CH₂CH(OH)CH₂OH | $C_{26}H_{38}N_4O_5$ | 487.29 | 487.2 |
| 34 | H | OH | H | H | (S)-CH[(CH₂)₂OH]C(O)OH | $C_{27}H_{38}N_4O_6$ | 515.29 | 515.2 |
| 35 | H | OH | H | H | (S)-CH[CH₂OH]C(O)OH | $C_{26}H_{36}N_4O_6$ | 501.27 | 501.2 |
| 36 | H | OH | H | H | (CH₂)₃-pyrrolidin-1-yl-2-one | $C_{30}H_{43}N_5O_4$ | 538.34 | 538.2 |
| 37 | H | OH | H | H | C(CH₃)(CH₂OH)CH₂OH | $C_{27}H_{40}N_4O_5$ | 501.31 | 501.2 |
| 38 | H | OH | H | H | (R)-CH₂-2-tetrahydrofuranyl | $C_{28}H_{40}N_4O_4$ | 497.31 | 497.2 |
| 39 | H | OH | H | H | (R)-CH[(CH₂)₂OH]COOH | $C_{27}H_{38}N_4O_6$ | 515.29 | 515.2 |

TABLE XXVI-continued

| No | $R^1$ | $R^3$ | $R^4$ | $R^5$ | Z | Molecular Formula | $[M + H]^+$ calcd | $[M + H]^+$ found |
|---|---|---|---|---|---|---|---|---|
| 40 | H | OH | H | $CH_3$ | $(CH_2)_2N(CH_3)SO_2N(CH_3)_2$ | $C_{29}H_{46}N_6O_5S$ | 591.34 | 591.2 |
| 41 | H | OH | $CH_3$ | $CH_3$ | $CH_2CH_2OCH_3$ | $C_{28}H_{42}N_4O_4$ | 499.33 | 499.4 |
| 42 | H | OH | $CH_3$ | $CH_3$ | $(CH_2)_2NHSO_2CH_3$ | $C_{28}H_{43}N_5O_5S$ | 562.31 | 562.2 |
| 43 | H | $OCH_3$ | H | $CH_2CH_2OH$ | $(CH_2)_2N(CH_3)SO_2CH_3$ | $C_{30}H_{47}N_5O_6S$ | 606.33 | 606.2 |
| 44 | H | $OCH_3$ | H | $CH_3$ | $CH_2C(O)N(CH_3)_2$ | $C_{29}H_{43}N_5O_4$ | 526.34 | 526.4 |
| 45 | H | $OCH_3$ | H | $CH_2CH_2OCH_3$ | $CH_2CH_2OCH_3$ | $C_{30}H_{46}N_4O_5$ | 543.36 | 543.4 |
| 46 | H | (a) | H | $CH_3$ | $CH_2C(O)N(CH_3)_2$ | $C_{31}H_{46}N_6O_5$ | 583.36 | 583.4 |
| 47 | H | (a) | H | $CH_2CH_2OCH_3$ | $CH_2CH_2OCH_3$ | $C_{32}H_{49}N_5O_6$ | 600.38 | 600.4 |
| 48 | H | (a) | H | $CH_3$ | $CH_2CH_2OH$ | $C_{29}H_{43}N_5O_5$ | 542.34 | 542.2 |
| 49 | H | (a) | H | $CH_3$ | $CH_2CH_2OCH_3$ | $C_{30}H_{45}N_5O_5$ | 556.35 | 556.4 |
| 50 | H | OH | H | $CH_2CH_2OH$ | $(CH_2)_2SO_2CH_3$ | $C_{28}H_{42}N_4O_6S$ | 563.29 | 563.2 |
| 51 | H | OH | H | $CH_2CH_2OCH_3$ | $(CH_2)_2SO_2CH_3$ | $C_{29}H_{44}N_4O_6S$ | 577.31 | 577.2 |
| 52 | H | (b) | H | $CH_2CH_2OCH_3$ | $(CH_2)_2SO_2CH_3$ | $C_{31}H_{47}N_5O_7S$ | 634.33 | 634.4 |
| 53 | H | (b) | H | $CH_3$ | $(CH_2)_2SO_2CH_3$ | $C_{29}H_{43}N_5O_6S$ | 590.30 | 590.2 |
| 54 | H | (S)-OH | H | $CH_2CN$ | $CH_2CN$ | $C_{31}H_{44}N_6O_5$ | 581.35 | 581.2 |
| 55 | H | OH | H | $CH_3$ | $(CH_2)_2$-1,1-dioxo-isothiazolidin-2-yl | $C_{29}H_{43}N_5O_5S$ | 574.31 | 574.3 |
| 56 | $CH_3$ | OH | H | $CH_3$ | $(CH_2)_2N(CH_3)C(O)OCH_3$ | $C_{30}H_{45}N_5O_5$ | 556.35 | 556.4 |
| 57 | $CH_3$ | OH | H | $CH_3$ | $(CH_2)_2NHSO_2CH_3$ | $C_{28}H_{43}N_5O_5S$ | 562.31 | 562.2 |
| 58 | $CH_3$ | OH | H | $CH_3$ | $(CH_2)_2N(CH_3)SO_2CH_3$ | $C_{29}H_{45}N_5O_5S$ | 576.32 | 576.4 |
| 59 | $CH_3$ | OH | H | $CH_2CH_2OCH_3$ | $(CH_2)_2N(CH_3)SO_2CH_3$ | $C_{31}H_{49}N_5O_6S$ | 620.35 | 620.4 |
| 60 | $CH_3$ | OH | H | $CH_2CH_2OH$ | $(CH_2)_2SO_2CH_3$ | $C_{29}H_{44}N_4O_6S$ | 577.31 | 577.2 |
| 61 | $CH_3$ | OH | H | $CH_3$ | $(CH_2)_2$-1,1-dioxo-isothiazolidin-2-yl | $C_{30}H_{45}N_5O_5S$ | 588.32 | 588.4 |
| 62 | F | OH | H | $CH_3$ | $CH_2C(O)N(CH_3)_2$ | $C_{28}H_{40}FN_5O_4$ | 530.32 | 530.2 |
| 63 | F | OH | H | $CH_3$ | $(CH_2)_2NHSO_2CH_3$ | $C_{27}H_{40}FN_5O_5S$ | 566.28 | 566.2 |
| 64 | F | OH | H | $CH_3$ | $(CH_2)_2N(CH_3)COOCH_3$ | $C_{29}H_{45}FN_5O_5$ | 560.33 | 560.2 |
| 65 | F | OH | H | $CH_3$ | $(CH_2)_2N(CH_3)SO_2CH_3$ | $C_{28}H_{42}FN_5O_5S$ | 580.30 | 580.2 |
| 66 | F | OH | H | $CH_2CH_2OCH_3$ | $(CH_2)_2N(CH_3)SO_2CH_3$ | $C_{30}H_{46}FN_5O_6S$ | 624.33 | 624.2 |
| 67 | F | OH | H | $CH_2CH_2OH$ | $(CH_2)_2SO_2CH_3$ | $C_{28}H_{41}FN_4O_6S$ | 581.28 | 581.2 |

(a) $OC(O)N(CH_3)_2$
(b) $OC(O)NHCH_3$

TABLE XXVII

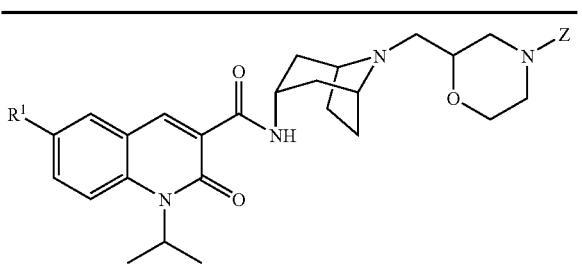

| No. | R¹ | Z | Molecular Formula | [M + H]⁺ calcd | [M + H]⁺ found |
|---|---|---|---|---|---|
| 1 | H | (CH$_2$)$_2$CH$_2$OH | C$_{27}$H$_{38}$N$_4$O$_4$ | 483.30 | 483.2 |
| 2 | H | (CH$_2$)$_2$OCH$_3$ | C$_{28}$H$_{40}$N$_4$O$_4$ | 497.31 | 497.3 |
| 3 | H | (CH$_2$)$_2$-2-pyrrolyl | C$_{31}$H$_{41}$N$_5$O$_3$ | 532.33 | 532.3 |
| 4 | H | CH$_2$-3-pyridinyl | C$_{31}$H$_{39}$N$_5$O$_3$ | 530.32 | 530.3 |
| 5 | H | (CH$_2$)$_2$NHC(O)OCH$_3$ | C$_{29}$H$_{41}$N$_5$O$_5$ | 540.32 | 540.3 |
| 6 | H | (CH$_2$)$_2$OC(O)N(CH$_3$)$_2$ | C$_{30}$H$_{43}$N$_5$O$_5$ | 554.34 | 554.3 |
| 7 | H | (CH$_2$)$_2$C(O)NHC$_2$H$_5$ | C$_{30}$H$_{43}$N$_5$O$_4$ | 538.34 | 538.3 |
| 8 | H | (CH$_2$)$_3$C(O)N(CH$_3$)$_2$ | C$_{31}$H$_{45}$N$_5$O$_4$ | 552.36 | 552.3 |
| 9 | H | (CH$_2$)$_2$NHSO$_2$CH$_3$ | C$_{28}$H$_{41}$N$_5$O$_5$S | 560.29 | 560.3 |
| 10 | H | (CH$_2$)$_2$N(CH$_3$)SO$_2$CH$_3$ | C$_{29}$H$_{43}$N$_5$O$_5$S | 574.31 | 574.3 |
| 11 | H | (CH$_2$)$_3$SO$_2$N(CH$_3$)$_2$ | C$_{30}$H$_{45}$N$_5$O$_5$S | 588.32 | 588.3 |
| 12 | H | CH$_2$CF$_3$ | C$_{27}$H$_{35}$F$_3$N$_4$O$_3$ | 521.28 | 521.2 |
| 13 | H | (CH$_2$)$_2$C(O)NH$_2$ | C$_{28}$H$_{39}$N$_5$O$_4$ | 510.31 | 510.2 |
| 14 | H | CH$_2$CN | C$_{27}$H$_{35}$N$_5$O$_3$ | 478.28 | 478.2 |
| 15 | H | CH$_2$C(O)NH$_2$ | C$_{27}$H$_{37}$N$_5$O$_4$ | 496.29 | 496.2 |
| 16 | H | CH$_2$C(O)N(CH$_3$)$_2$ | C$_{29}$H$_{41}$N$_5$O$_4$ | 524.33 | 524.2 |

TABLE XXVIII

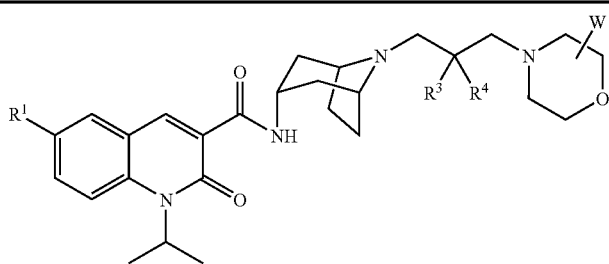

| No. | R¹ | R³ | R⁴ | W | Molecular Formula | [M + H]⁺ calcd | [M + H]⁺ found |
|---|---|---|---|---|---|---|---|
| 1 | H | OH | H | 2-CH$_2$NHSO$_2$CH$_3$ | C$_{29}$H$_{43}$N$_5$O$_6$S | 590.30 | 590.2 |
| 2 | H | OH | H | 3-CH$_2$N(CH$_3$)SO$_2$CH$_3$ | C$_{30}$H$_{45}$N$_5$O$_6$S | 604.32 | 604.2 |
| 3 | H | OH | CH$_3$ | 2-CH$_2$NHSO$_2$CH$_3$ | C$_{30}$H$_{45}$N$_5$O$_6$S | 604.32 | 604.2 |
| 4 | H | OH | H | 3-CH$_2$OH | C$_{28}$H$_{40}$N$_4$O$_5$ | 513.31 | 513.2 |
| 5 | H | OCH$_3$ | H | 3-CH$_2$OH | C$_{29}$H$_{42}$N$_4$O$_5$ | 527.33 | 527.2 |
| 6 | H | OC(O)N(CH$_3$)$_2$ | H | 3-CH$_2$N(CH$_3$)SO$_2$CH$_3$ | C$_{33}$H$_{50}$N$_6$O$_7$S | 675.36 | 675.4 |
| 7 | H | OC(O)N(CH$_3$)$_2$ | H | 3-CH$_2$OH | C$_{31}$H$_{45}$N$_5$O$_6$ | 584.35 | 584.2 |

Example 16

Radioligand Binding Assay on 5-HT$_{4(c)}$ Human Receptors a. Membrane Preparation 5-HT$_{4(c)}$ HEK-293 (human embryonic kidney) cells stably-transfected with human 5-HT$_{4(c)}$receptor cDNA (Bmax=~6.0 pmol/mg protein, as determined using [³H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GIBCO-Invitrogen Corp.: Cat #10437), 2 mM L-glutamine and (100 units) penicillin-(100 µg) streptomycin/ml (GIBCO-Invitrogen Corp.: Cat #15140) in a 5% CO$_2$, humidified incubator at 37° C. Cells were grown under continuous selection pressure by the addition of 800 µg/mL geneticin (GIBCO-Invitrogen Corp.: Cat #10131) to the medium.

Cells were grown to roughly 60-80% confluency (<35 sub-culture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −800C.

b. Radioligand Binding Assays

Radioligand binding assays were performed in 1.1 mL 96-deep well polypropylene assay plates (Axygen) in a total assay volume of 400 µL containing 2 µg membrane protein in 50 mM HEPES pH 7.4, containing 0.025% bovine serum albumin (BSA). Saturation binding studies for determination of K$_d$ values of the radioligand were performed using [³H]-

GR113808 (Amersham Inc., Bucks, UK: Cat #TRK944; specific activity ~82 Ci/mmol) at 8-12 different concentrations ranging from 0.001 nM-5.0 nM. Displacement assays for determination of $pK_i$ values of compounds were performed with [$^3$H]-GR113808 at 0.15 nM and eleven different concentrations of compound ranging from 10 pM-100 µM.

Test compounds were received as 10 mM stock solutions in DMSO and diluted to 400 µM into 50 mM HEPES pH 7.4 at 25° C., containing 0.1% BSA, and serial dilutions (1:5) then made in the same buffer. Non-specific binding was determined in the presence of 1 µM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 µM GR113808. $K_i$ values for test compounds were calculated, in Prism, from the best-fit $IC_{50}$ values, and the $K_d$ value of the radioligand, using the Cheng-Prusoff equation (Cheng and Prusoff, *Biochemical Pharmacology*, 1973, 22, 3099-108): $K_i=IC_{50}/(1+[L]/K_d)$ where [L]=concentration [$^3$H]-GR113808. Results are expressed as the negative decadic logarithm of the $K_i$ values, $pK_i$.

Test compounds having a higher $pK_i$ value in this assay have a higher binding affinity for the 5-HT$_4$ receptor. The compounds of the invention which were tested in this assay had a $pK_i$ value ranging from about 6 to about 9.

Example 17

Radioligand Binding Assay on 5-HT$_{3A}$ Human Receptors: Determination of Receptor Subtype Selectivity a. Membrane Preparation 5-HT A HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 µg) streptomycin/ml (GIBCO-Invitrogen Corp.: Cat #15140) in a 5% CO$_2$, humidified incubator at 37° C.

Cells were grown to roughly 70-80% confluency (<35 subculture passages). All steps of the membrane preparation were performed on ice. To harvest the cells, the media was aspirated and cells were rinsed with Ca$^{2+}$, Mg$^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 µL containing 1.5-2 µg membrane protein in 50 mM HEPES pH 7.4, containing 0.025% BSA assay buffer. Saturation binding studies for determination of $K_d$ values of the radioligand were performed using [$^3$H]-GR65630 (PerkinElmer Life Sciences Inc., Boston, Mass.: Cat #NET1101, specific activity 85 Ci/mmol) at twelve different concentrations ranging from 0.005 nM to 20 nM. Displacement assays for determination of $pK_i$ values of compounds were performed with [$^3$H]-GR65630 at 0.50 nM and eleven different concentrations of compound ranging from 10 pM to 100 µM. Compounds were received as 10 mM stock solutions in DMSO (see section 3.1), diluted to 400 µM into 50 mM HEPES pH 7.4 at 25° C., containing 0.1% BSA, and serial (1:5) dilutions then made in the same buffer. Non-specific binding was determined in the presence of 10 µM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for non-specific binding, as determined in the presence of 10 µM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio $K_i$(5-HT$_{3A}$)/$K_i$(5-HT$_{4(c)}$). The compounds of the invention which were tested in this assay had a 5-HT$_4$/5-HT$_3$ receptor subtype selectivity ranging from about 10 to about 8000.

Example 18

Whole-Cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [$^3$H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 μg) streptomycin/ml (GIBCO-Invitrogen Corp.: Cat #15140) in a 5% $CO_2$, humidified incubator at 37° C. Cells were grown under continuous selection pressure by the addition of geneticin (800 μg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 μm, flask yield was $1-2 \times 10^7$ cells/flask). Cells were resuspended at a concentration of $5 \times 10^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were $25 \times 10^3$ cells/well and the final assay volume was 100 μL. Test compounds were received as 10 mM stock solutions in DMSO, diluted to 400 μM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 μM (final assay concentrations). A 5-HT concentration-response curve (10 pM to 100 μM) was included on every plate. The cells were incubated, with shaking, at 37° C. for 15 min and the reaction terminated by addition of 100 μl of ice-cold detection buffer (as provided in the flashplate kit) to each well. The plates were sealed and incubated at 4° C. overnight. Bound radioactivity was quantified by scintillation proximity spectroscopy using the Topcount (Packard Bio-Science Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as $pEC_{50}$ values, the negative decadic logarithm of the $EC_{50}$ value, where $EC_{50}$ is the effective concentration for a 50% maximal response.

Test compounds exhibiting a higher $pEC_{50}$ value in this assay have a higher potency for agonizing the $5-HT_4$ receptor. The compounds of the invention which were tested in this assay, for example, in the cell line (1) having a density of about 0.5-0.6 pmol/mg protein, had a $pEC_{50}$ value ranging from about 6 to about 9.

Example 19

In vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 μg/mL geneticin. Cells were seeded onto poly-D-lysine (100 μg/mL) coated glass coverslips, in 35 mm² dishes (containing 2 mL medium) at a density that enabled isolated cells to be selected for whole cell voltage-clamp studies. The dishes were maintained in a humidified, 5% $CO_2$ environment at 37° C.

Extracellular solution was prepared at least every 7 days and stored at 4° C. when not in use. The extracellular solution contained (mM): NaCl (137), KCl (4), $CaCl_2$ (1.8), $MgCl_2$ (1), Glucose (10), 4-(2-hydroxyethyl)-1-piperazineethane-sulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), $MgCl_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 sec and then return to the original holding potential (−80 mV). This voltage protocol was run once every 15 sec (0.067 Hz). Peak current amplitudes during the repolarization phase were determined using pClamp software. Test compounds at a concentration of 3 μM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed $K^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at p<0.05.

The smaller the percentage inhibition of the potassium ion current in this assay, the smaller the potential for test compounds to change the pattern of cardiac repolarization when used as therapeutic agents. For example, the compounds of Examples 1-14, which were tested in this assay at a concentration of 3 μM, exhibited an inhibition of the potassium ion current of less than about 25%, typically, less than about 15%.

Example 20

Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min. and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC (0-t)) was calculated by the linear trapezoidal rule. Oral bioavailability (F(%)), i.e. the dose-normalized ratio of AUC(0-t) for PO administration to AUC(O-t) for IV administration, was calculated as:

$$F(\%) = AUC_{PO}/AUC_{IV} \times Dose_{IV}/Dose_{PO} \times 100\%$$

Test compounds which exhibit larger values of the parameters $C_{max}$, AUC(O-t), and F(%) in this assay are expected to have greater bioavailability when administered orally. For example, the compounds of Examples 1-14 were tested in this assay and had $C_{max}$ values typically ranging from about 0.05 to about 0.4 μg/mL and AUC(O-t) values typically ranging from about 0.15 to about 0.9 μg·hr/mL.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:
1. A compound of formula (I):

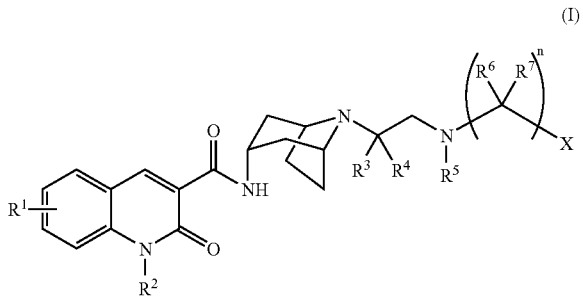

wherein:
$R^1$ is hydrogen, halo, hydroxy, $C_{1-4}$alkyl, or $C_{1-4}$alkoxy;
$R^2$ is $C_{3-4}$alkyl or $C_{3-6}$cycloalkyl;
$R^3$ is hydroxy, $C_{1-3}$alkoxy, hydroxy-substituted $C_{1-4}$alkyl, or —OC(O)NR$^a$R$^b$;
$R^4$ is hydrogen or $C_{1-4}$alkyl;
X is selected from —N(R$^8$)C(O)R$^9$, —N(R$^8$)S(O)$_2$R$^{10}$, —S(R$^{11}$)O$_2$, —N(R$^8$)C(O)OR$^{12}$, —N(R$^8$)C(O)NR$^{13}$R$^{14}$, —N(R$^8$)SO$_2$NR$^{13}$R$^{14}$, —C(O)NR$^{13}$R$^{14}$, —OC(O)NR$^{13}$R$^{14}$, —C(O)OR$^{12}$, —OR$^{15}$, and cyano;
$R^5$ is hydrogen or $C_{1-4}$alkyl, wherein $C_{1-4}$alkyl is optionally substituted with hydroxy, $C_{1-3}$alkoxy, or cyano;
$R^6$ and $R^7$ are independently selected from hydrogen, hydroxy, halo, and $C_{1-4}$alkyl, wherein $C_{1-4}$alkyl is optionally substituted with hydroxy or $C_{1-3}$alkoxy;
$R^8$ is hydrogen or $C_{1-4}$alkyl;
or $R^5$ and $R^8$, $R^5$ and $R^6$, or $R^6$ and $R^8$ taken together form $C_{2-5}$alkylenyl, wherein $C_{2-5}$alkylenyl is optionally substituted with hydroxy, halo, hydroxy-substituted $C_{1-3}$alkyl, or $C_{1-3}$alkoxy;
or $R^3$ and $R^5$ taken together form —OCH$_2$CH$_2$—;
or $R^5$ and $R^6$ taken together form —(CH$_2$)$_q$—Q—(CH$_2$)$_q$, wherein Q is oxygen or sulfur and q is independently 0, 1, or 2;
$R^9$ is hydrogen, furanyl, or $C_{1-4}$alkyl, wherein $C_{1-4}$alkyl is optionally substituted with hydroxy or with from 1 to 3 halo;
$R^{10}$ is hydrogen or $C_{1-4}$alkyl, wherein $C_{1-4}$alkyl is optionally substituted with —SO$_2$R$^c$, $C_{3-6}$cycloalkyl or with from 1 to 3 halo;
or $R^8$ and $R^{10}$ taken together form $C_3$alkylenyl;
$R^{11}$ is hydrogen, $C_{1-4}$alkyl, or —NR$^b$R$^c$;
or $R^5$ and $R^{11}$ or $R^6$ and $R^{11}$ taken together form $C_{2-5}$alkylenyl;
$R^{12}$, $R^{13}$, and $R^{14}$ are independently hydrogen or $C_{1-4}$alkyl;
$R^{15}$ is hydrogen or $C_{1-4}$alkyl, wherein $C_{1-4}$alkyl is optionally substituted with hydroxy;
$R^a$, $R^b$, and $R^c$ are independently hydrogen or $C_{1-3}$alkyl; and
n is 1, 2, 3, or 4;
provided that when n is 1, X forms a carbon-carbon bond with the carbon atom bearing the substituents $R^6$ and $R^7$;
or a pharmaceutically-acceptable salt or stereoisomer thereof.

2. The compound of claim 1 wherein:
$R^5$ is hydrogen or $C_{1-4}$alkyl, wherein $C_{1-4}$alkyl is optionally substituted with hydroxy, $C_{1-3}$alkoxy, or cyano;
$R^6$ and $R^7$ are independently selected from hydrogen, hydroxy, halo, and $C_{1-4}$alkyl, wherein $C_{1-4}$alkyl is optionally substituted with hydroxy or $C_{1-3}$alkoxy;

$R^8$ is hydrogen or $C_{1-4}$alkyl;

$R^{10}$ is hydrogen or $C_{1-4}$alkyl, wherein $C_{1-4}$alkyl is optionally substituted with —$SO_2R^c$, $C_{3-6}$cycloalkyl or with from 1 to 3 halo;

$R^{11}$ is hydrogen, $C_{1-4}$alkyl, or —$NR^bR^c$; and $R^{15}$ is hydrogen or $C_{1-4}$alkyl, wherein $C_{1-4}$alkyl is optionally substituted with hydroxy.

3. The compound of claim 1 wherein $R^2$ is $C_{3-4}$alkyl.

4. The compound of claim 3 wherein n is 2 or 3.

5. The compound of claim 3 wherein n is 2.

6. The compound of claim 1 which is a compound of formula (II):

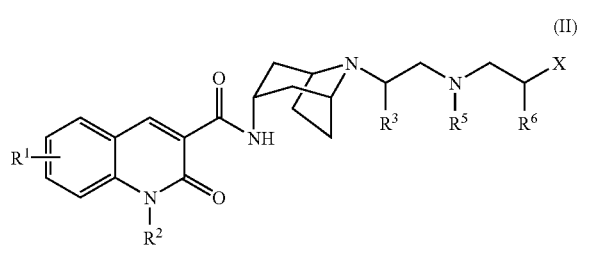

(II)

$R^1$ is hydrogen, halo, or $C_{1-3}$alkyl;

$R^2$ is $C_{3-4}$alkyl;

$R^3$ is hydroxy, $C_{1-3}$alkoxy, hydroxy-substituted $C_{1-2}$alkyl, or —$OC(O)NR^aR^b$;

$R^5$ is hydrogen, $C_{1-3}$alkyl, or $C_{1-3}$alkyl substituted at the terminal position with hydroxy or cyano;

$R^6$ is hydrogen;

X is selected from —$N(R^8)C(O)R^9$; —$N(R^8)S(O)_2R^{10}$, —$S(R^{11})O_2$, —$N(R^8)C(O)NR^{13}R^{14}$, —$C(O)NR^{13}R^{14}$, —$OC(O)NR^{13}R^{14}$, —$OR^{15}$, and cyano;

$R^8$ is hydrogen or $C_{1-3}$alkyl;

$R^9$ is hydrogen or $C_{1-3}$alkyl;

$R^{10}$ is hydrogen or $C_{1-3}$alkyl, wherein $C_{1-3}$alkyl is optionally substituted with —$SO_2R^c$ wherein $R^c$ is $C_{1-3}$alkyl;

$R^{13}$, $R^{14}$, and $R^{15}$ are independently hydrogen or $C_{1-3}$alkyl;

or $R^5$ and $R^8$, $R^5$ and $R^6$, or $R^5$ and $R^{11}$ taken together form $C_2$alkylenyl; or a pharmaceutically-acceptable salt or stereoisomer thereof.

7. The compound of claim 6 wherein:

$R^1$ is hydrogen;

$R^2$ is $C_{3-4}$alkyl;

$R^3$ is hydroxy, methoxy, hydroxymethyl, —$OC(O)N(H)CH_3$, or —$OC(O)N(CH_3)_2$;

$R^6$ is hydrogen;

X is selected from —$N(R^8)C(O)R^9$; —$N(R^8)S(O)_2R^{10}$, —$S(R^{11})O_2$, and —$N(R^8)C(O)NR^{13}R^{14}$;

$R^5$ and $R^8$ taken together form $C_2$alkylenyl;

$R^9$ is hydrogen or $C_{1-3}$alkyl;

$R^{10}$ is hydrogen, $C_{1-3}$alkyl, or methanesulfonylmethyl;

$R^5$ and $R^{11}$ taken together form $C_2$alkylenyl; and $R^{13}$ and $R^{14}$ are independently hydrogen or $C_{1-3}$alkyl.

8. The compound of claim 1 wherein the compound is of formula (III):

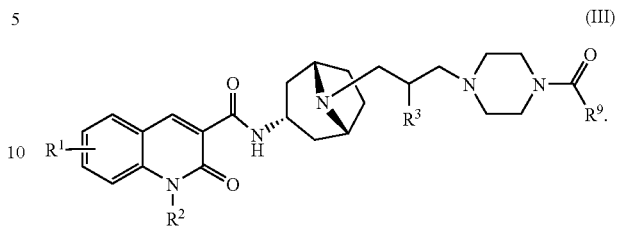

(III)

9. The compound of claim 1 wherein the compound is of formula (IV):

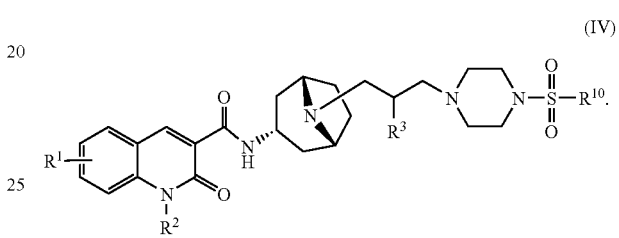

(IV)

10. The compound of claim 1 wherein the compound is of formula (V):

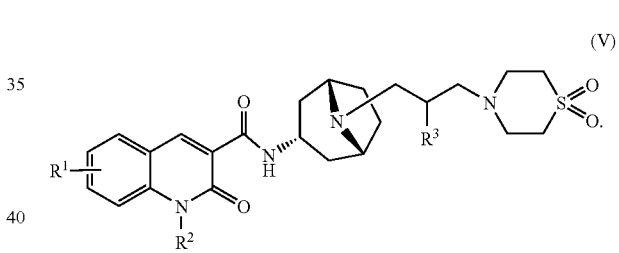

(V)

11. The compound of claim 1 wherein the compound is selected from:

1-isopropyl-2-oxo-1,2-dihydroquinoline-3-carboxylic acid {(1S,3R,5R)-8-[2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid ((1S,3R,5R)-8-{2-hydroxy-3-[4-(propane-2-sulfonyl)piperazin-1-yl]propyl}-8-azabicyclo[3.2.1]oct-3-yl)-amide;

1-isopropyl-2-oxo-1,2-dihydroquinoline-3-carboxylic acid {(1S,3R,5R)-8-[3-(1,1-dioxo-1λ⁶-thiomorpholin-4-yl)-2-hydroxypropyl]-8-azabicyclo[3.2.1]oct-3-yl}amide;

1-isopropyl-2-oxo-1,2-dihydroquinoline-3-carboxylic acid {(1S,3R,5R)-8-[(S)-2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid {(1S,3R,5R)-8-[(R)-2-hydroxy-3-(4-methanesulfonylpiperazin-1-yl)propyl]-8-azabicyclo[3.2.1]oct-3-yl}amide;

1-isopropyl-2-oxo-1,2-dihydroquinoline-3-carboxylic acid {(1S,3R,5R)-8-[3-(4-methanesulfonylmethanesulfonylpiperazin-1-yl)-2-methoxypropyl]-8-azabicyclo[3.2.1]-oct-3-yl}amide;

1-isopropyl-2-oxo-1,2-dihydroquinoline-3-carboxylic acid {(1S,3R,5R)-8-[3-(4-acetylpiperazin-1-yl)-2-methoxypropyl]-8-azabicyclo[3.2.1]oct-3-yl}amide;

1-isopropyl-2-oxo-1,2-dihydroquinoline-3-carboxylic acid {(1S,3R,5R)-8-[3-(1,1-dioxo-1λ⁶-thiomorpholin-4-yl)-2-methoxypropyl]-8-azabicyclo[3.2.1]oct-3-yl}amide;

methylcarbamic acid 2-{(1S,3R,5R)-3-[(1-isopropyl-2-oxo-1,2-dihydroquinoline-3-carbonyl)amino]-8-azabicyclo[3.2.1]oct-8-yl}-1-(4-methanesulfonylpiperazin-1-yl-methyl)ethyl ester;

methylcarbamic acid 1-(4-dimethylcarbamoylpiperazin-1-ylmethyl)-2-{(1S,3R,5R)-3-[(1-isopropyl-2-oxo-1,2-dihydroquinoline-3-carbonyl)amino]-8-aza-bicyclo[3.2.1]oct-8-yl}ethyl ester;

methylcarbamic acid 1-[3-(acetylmethylamino)pyrrolidin-1-ylmethyl]-2-{(1S,3R,5R)-3-[(1-isopropyl-2-oxo-1,2-dihydroquinoline-3-carbonyl)amino]-8-aza-bicyclo[3.2.1]oct-8-yl}ethyl ester;

methylcarbamic acid 1-(4-acetylpiperazin-1-ylmethyl)-2-{(1S,3R,5R)-3-[(1-isopropyl-2-oxo-1,2-dihydroquinoline-3-carbonyl)amino]-8-azabicyclo[3.2.1]oct-8-yl}-ethyl ester;

methylcarbamic acid (R)-2-{(1S,3R,5R)-3-[(1-isopropyl-2-oxo-1,2-dihydro-quinoline-3-carbonyl)amino]-8-azabicyclo[3.2.1]oct-8-yl}-1-(4-methanesulfonyl-piperazin-1-ylmethyl)ethyl ester;

1-isopropyl-2-oxo-1,2-dihydroquinoline-3-carboxylic acid {(1S,3R,5R)-8-[3-hydroxy-2-(4-methanesulfonylpiperazin-1-ylmethyl)propyl]-8-azabicyclo[3.2.1]oct-3-yl}-amide; and pharmaceutically-acceptable salts thereof.

12. A process for preparing a compound of formula (I):

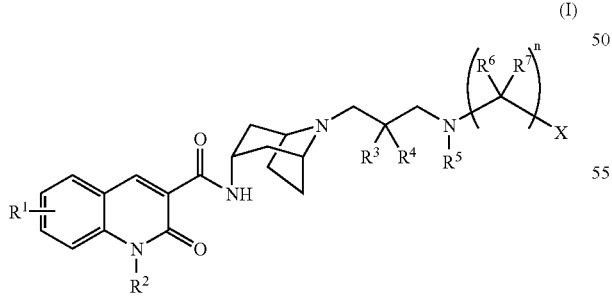

(I)

wherein $R^1$, $R^2$, $R^3$, $R^4$, $R^5$, $R^6$, $R^7$, n, and X are defined as in claim 1, or a salt or stereoisomer thereof, the process comprising:

(a) reacting a compound of formula (VI):

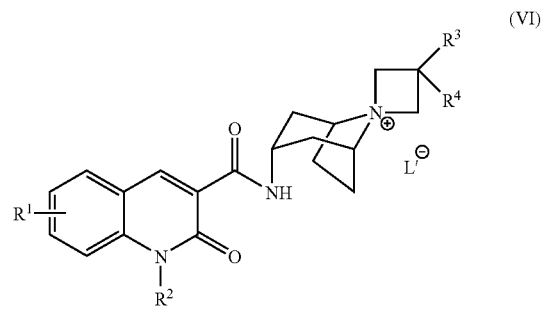

(VI)

wherein L' is an anion, with a compound of formula (VII):

(VII)

or (b) reacting a compound of formula (VIII):

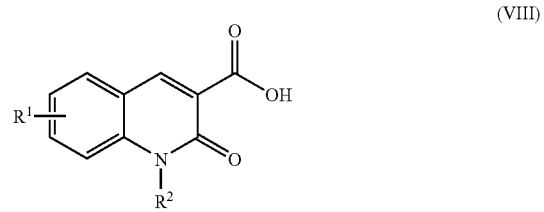

(VIII)

with a compound of formula (IX):

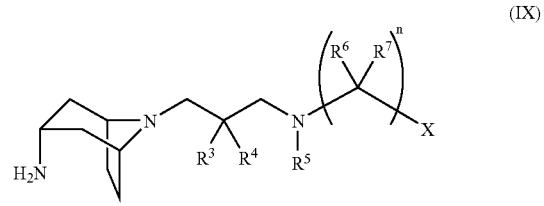

(IX)

to provide a compound of formula (I), or a salt or stereoisomer thereof.

13. A process for preparing a compound of formula (I):

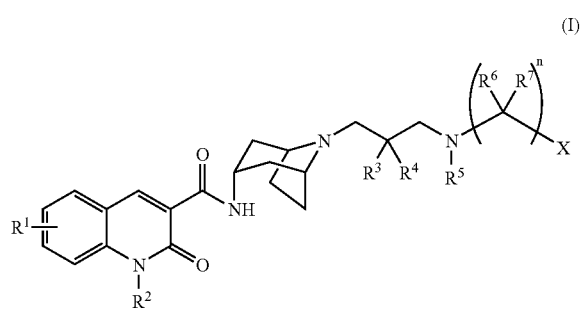

(I)

wherein R³ is hydroxy, and R¹, R², R⁴, R⁵, R⁶, R⁷, n, and X are defined as in claim 1, or a salt or stereoisomer thereof, the process comprising:

step (a) or step (b) as defined in claim 13, or (c) reacting a compound of formula (X):

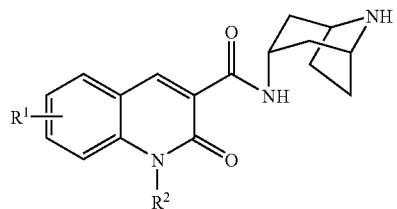

(X)

or a salt thereof, with a compound of formula (VII) and a compound of formula (XI):

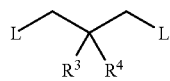

(XI)

wherein L is a leaving group;

or (d) reacting a compound of formula (X) with a compound of formula (XII):

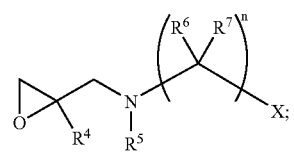

(XII)

to provide a compound of formula (I), or a salt or stereoisomer thereof.

* * * * *

UNITED STATES PATENT AND TRADEMARK OFFICE
CERTIFICATE OF CORRECTION

PATENT NO. : 7,396,933 B2  Page 1 of 1
APPLICATION NO. : 11/267720
DATED : July 8, 2008
INVENTOR(S) : Choi et al.

It is certified that error appears in the above-identified patent and that said Letters Patent is hereby corrected as shown below:

Column 75,
line 28, insert --wherein:--.

Column 79,
line 4, "claim 13" should be --claim 12--.

Signed and Sealed this

Twenty-first Day of October, 2008

JON W. DUDAS
*Director of the United States Patent and Trademark Office*